(12) United States Patent
Carlos et al.

(10) Patent No.: US 9,745,270 B2
(45) Date of Patent: Aug. 29, 2017

(54) PROCESSES USEFUL FOR THE PREPARATION OF 1-[3-(4-BROMO-2-METHYL-2H-PYRAZOL-3-YL)-4-METHOXY-PHENYL]-3-(2,4-DIFLUORO-PHENYL)-UREA AND CRYSTALLINE FORMS RELATED THERETO

(71) Applicant: Arena Pharmaceuticals, Inc., San Diego, CA (US)

(72) Inventors: Marlon Carlos, Chula Vista, CA (US); Weitong Dong, Shanghai (CN); Mark Macias, San Diego, CA (US); Suzanne Michiko Sato, San Diego, CA (US); Lee Alani Selvey, Poway, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 15/144,012

(22) Filed: May 2, 2016

(65) Prior Publication Data

US 2017/0057924 A1    Mar. 2, 2017

Related U.S. Application Data

(63) Continuation of application No. 14/679,421, filed on Apr. 6, 2015, now Pat. No. 9,353,064, which is a
(Continued)

(51) Int. Cl.
| | | |
|---|---|---|
| C07D 231/16 | (2006.01) | |
| A61K 31/415 | (2006.01) | |
| C07D 231/12 | (2006.01) | |

(52) U.S. Cl.
CPC ......... *C07D 231/12* (2013.01); *C07D 231/16* (2013.01)

(58) Field of Classification Search
CPC ........................... A61K 31/415; C07C 231/16
(Continued)

(56) References Cited

U.S. PATENT DOCUMENTS 4,099,012 A   7/1978   Gschwend
4,405,644 A   9/1983   Kabbe et al.
(Continued)

FOREIGN PATENT DOCUMENTS

CA   2135253        5/1996
CA   2169231 A1    8/1996
(Continued)

OTHER PUBLICATIONS

"Arena Pharmaceuticals Announces Preliminary Results of Phase 2b Clinical Trial of APD125 for the Treatment of Insomnia" PRNewswire-FirstCall via COMTEX News Network, Press Release dated Dec. 9, 2008.
(Continued)

*Primary Examiner* — Kamal Saeed
*Assistant Examiner* — Janet L Coppins
(74) *Attorney, Agent, or Firm* — Pepper Hamilton LLP

(57) ABSTRACT

The present invention is directed to processes and intermediates useful for the preparation of 1-[3-(4-bromo-2-methyl-2H-pyrazol-3-yl)-4-methoxy-phenyl]-3-(2,4-difluoro-phenyl)-urea (Compound I), crystalline forms and solvate forms thereof; and compositions comprising 1-[3-(4-bromo-2-methyl-2H-pyrazol-3-yl)-4-methoxy-phenyl]-3-(2,4-difluoro-phenyl)-urea, crystalline forms and solvate forms thereof prepared by processes as described herein.

8 Claims, 31 Drawing Sheets

Related U.S. Application Data continuation of application No. 13/126,563, filed as application No. PCT/US2009/005809 on Oct. 27, 2009, now Pat. No. 9,126,946.

(60) Provisional application No. 61/197,499, filed on Oct. 28, 2008.

(58) Field of Classification Search
USPC .................................. 514/406; 548/377.1
See application file for complete search history.

(56) References Cited

U.S. PATENT DOCUMENTS

| | | |
|---|---|---|
| 4,409,231 A | 10/1983 | Stenzel et al. |
| 4,482,534 A | 11/1984 | Blank |
| 4,555,399 A | 11/1985 | Hsiao |
| 4,985,352 A | 1/1991 | Julius et al. |
| 5,077,409 A | 12/1991 | Wissner |
| 5,128,351 A | 7/1992 | Wissner |
| 5,346,906 A | 9/1994 | Baker et al. |
| 5,523,280 A | 6/1996 | Chene et al. |
| 5,576,338 A | 11/1996 | Friesen et al. |
| 5,596,001 A | 1/1997 | Hamanaka |
| 5,661,024 A | 8/1997 | Kao et al. |
| 5,856,326 A | 1/1999 | Anthony et al. |
| 5,861,431 A | 1/1999 | Hildebrand et al. |
| 5,885,785 A | 3/1999 | Kao et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,083 A | 2/2000 | Carr et al. |
| 6,028,085 A | 2/2000 | Bromidge |
| 6,054,472 A | 4/2000 | Armistead et al. |
| 6,063,808 A | 5/2000 | Fabiano et al. |
| 6,107,324 A | 8/2000 | Behan et al. |
| 6,110,498 A | 8/2000 | Rudnic et al. |
| 6,140,509 A | 10/2000 | Behan et al. |
| 6,150,393 A | 11/2000 | Behan et al. |
| 6,172,084 B1 | 1/2001 | Cuny et al. |
| 6,180,138 B1 | 1/2001 | Engh et al. |
| 6,187,805 B1 | 2/2001 | Pineiro et al. |
| 6,204,285 B1 | 3/2001 | Fabiano et al. |
| 6,207,679 B1 | 3/2001 | Cuny et al. |
| 6,271,261 B1 | 8/2001 | Widdowson |
| 6,284,269 B1 | 9/2001 | Struengmann et al. |
| 6,297,261 B1 | 10/2001 | Christophersen et al. |
| 6,310,212 B1 | 10/2001 | Yuan et al. |
| 6,316,450 B1 | 11/2001 | Bromidge et al. |
| 6,358,698 B1 | 3/2002 | Weiner et al. |
| 6,376,670 B1 | 4/2002 | Cuny et al. |
| 6,380,199 B1 | 4/2002 | Reavill et al. |
| 6,383,762 B1 | 5/2002 | Kao et al. |
| 6,403,808 B1 | 6/2002 | Glennon et al. |
| 6,417,393 B1 | 7/2002 | Christophersen et al. |
| 6,420,541 B1 | 7/2002 | Behan et al. |
| 6,469,006 B1 | 10/2002 | Blair et al. |
| 6,479,480 B1 | 11/2002 | Moyes et al. |
| 6,479,519 B1 | 11/2002 | Astles et al. |
| 6,489,488 B2 | 12/2002 | Glennon et al. |
| 6,518,297 B2 | 2/2003 | Glennon et al. |
| 6,531,291 B1 | 3/2003 | Kabbash et al. |
| 6,541,209 B1 | 4/2003 | Behan et al. |
| 6,541,477 B2 | 4/2003 | Goehring et al. |
| 6,548,504 B1 | 4/2003 | Bromidge et al. |
| 6,608,085 B1 | 8/2003 | Gillespie et al. |
| 6,627,661 B2 | 9/2003 | Reavill et al. |
| 6,696,475 B2 | 2/2004 | Dahl et al. |
| 6,706,749 B2 | 3/2004 | Dahl et al. |
| 6,753,442 B1 | 6/2004 | Benedini et al. |
| 6,784,183 B2 | 8/2004 | Lavielle et al. |
| 6,787,535 B2 | 9/2004 | Beard et al. |
| 6,846,919 B2 | 1/2005 | Behan et al. |
| 6,849,644 B2 | 2/2005 | Bromidge et al. |
| 7,084,169 B2 | 8/2006 | Zhao |
| 7,087,750 B2 | 8/2006 | Caldirola et al. |
| 7,091,236 B1 | 8/2006 | Roberts et al. |
| 7,098,233 B2 | 8/2006 | Di Cesare et al. |
| 7,262,188 B2 | 8/2007 | MacDonald et al. |
| 7,368,539 B2 | 5/2008 | Behan et al. |
| 7,452,888 B2 | 11/2008 | Ahmed et al. |
| 7,601,837 B2 | 10/2009 | Ahmed et al. |
| 7,754,724 B2 | 7/2010 | Lorsbach et al. |
| 7,799,774 B2 | 9/2010 | Ahmed et al. |
| 7,943,639 B2 | 5/2011 | Johansson et al. |
| 7,977,337 B2 | 7/2011 | Ahmed et al. |
| 8,236,947 B2 | 8/2012 | Ahmed et al. |
| 8,404,690 B2 | 3/2013 | Page et al. |
| 8,481,535 B2 | 7/2013 | Gharbaoui et al. |
| 9,029,379 B2 | 5/2015 | Korenberg et al. |
| 9,034,911 B2 | 5/2015 | Selvey et al. |
| 9,084,742 B2 | 7/2015 | Chuang et al. |
| 9,126,946 B2 * | 9/2015 | Carlos ................. C07D 231/16 |
| 9,353,064 B2 * | 5/2016 | Carlos ................. C07D 231/16 |
| 2001/0022963 A1 | 9/2001 | Klaveness et al. |
| 2001/0051719 A1 | 12/2001 | Bromidge et al. |
| 2002/0025965 A1 | 2/2002 | Lavielle et al. |
| 2002/0025967 A1 | 2/2002 | Smith |
| 2002/0098548 A1 | 7/2002 | Kao et al. |
| 2002/0115670 A1 | 8/2002 | Kelly et al. |
| 2003/0037274 A1 | 2/2003 | Shikata et al. |
| 2003/0144505 A1 | 7/2003 | Bromidge et al. |
| 2004/0024210 A1 | 2/2004 | Johansson et al. |
| 2004/0034036 A1 | 2/2004 | Bromidge et al. |
| 2004/0077654 A1 | 4/2004 | Bouillot et al. |
| 2004/0082644 A1 | 4/2004 | Korsten |
| 2004/0092528 A1 | 5/2004 | Kelly et al. |
| 2004/0102636 A1 | 5/2004 | Miller et al. |
| 2004/0122076 A1 | 6/2004 | Bobb et al. |
| 2004/0132742 A1 | 7/2004 | Bromidge et al. |
| 2004/0167030 A1 | 8/2004 | Bernotas et al. |
| 2005/0054691 A1 | 3/2005 | Potter et al. |
| 2005/0080124 A1 | 4/2005 | Teegarden et al. |
| 2005/0090485 A1 | 4/2005 | Bromidge et al. |
| 2005/0090496 A1 | 4/2005 | Ahmed et al. |
| 2005/0124628 A1 | 6/2005 | Ahmend et al. |
| 2005/0176705 A1 | 8/2005 | Bromidge |
| 2005/0176759 A1 | 8/2005 | Ahmed et al. |
| 2005/0215526 A1 | 9/2005 | Hulme et al. |
| 2005/0267097 A1 | 12/2005 | Pinto et al. |
| 2006/0014705 A1 | 1/2006 | Howitz et al. |
| 2006/0018839 A1 | 1/2006 | Ieni et al. |
| 2006/0035888 A1 | 2/2006 | Jonas et al. |
| 2006/0063754 A1 | 3/2006 | Edgar et al. |
| 2006/0142241 A1 | 6/2006 | Yooh |
| 2006/0148818 A1 | 7/2006 | Johansson et al. |
| 2006/0172992 A1 | 8/2006 | Yokoyama et al. |
| 2006/0205792 A1 | 9/2006 | Wong et al. |
| 2006/0229335 A1 | 10/2006 | Teegarden et al. |
| 2006/0287334 A1 | 12/2006 | Johnson et al. |
| 2007/0004750 A1 | 1/2007 | Lorsbach et al. |
| 2007/0027139 A1 | 2/2007 | Johnson et al. |
| 2007/0032504 A1 | 2/2007 | Gladwin |
| 2007/0037827 A1 | 2/2007 | Nunes et al. |
| 2007/0043058 A1 | 2/2007 | Bang-Andersen et al. |
| 2007/0072857 A1 | 3/2007 | Teegarden et al. |
| 2007/0078134 A1 | 4/2007 | Teegarden et al. |
| 2007/0167431 A1 | 7/2007 | Comery et al. |
| 2007/0191345 A1 | 8/2007 | Ahmed et al. |
| 2007/0207994 A1 | 9/2007 | Teegarden et al. |
| 2007/0244086 A1 | 10/2007 | Teegarden et al. |
| 2007/0249603 A1 | 10/2007 | Johnson et al. |
| 2007/0275979 A1 | 11/2007 | MacDonald et al. |
| 2007/0293539 A1 | 12/2007 | Lansbury et al. |
| 2007/0293685 A1 | 12/2007 | Fritch et al. |
| 2008/0015223 A1 | 1/2008 | Strah-Pleynet et al. |
| 2008/0114014 A1 | 5/2008 | Rich |
| 2008/0194836 A1 | 8/2008 | Gharbaoui et al. |
| 2008/0200530 A1 | 8/2008 | Unett et al. |
| 2008/0255359 A1 | 10/2008 | Wade |
| 2009/0036682 A1 | 2/2009 | Ahmed et al. |
| 2009/0053306 A1 | 2/2009 | Agarwal et al. |
| 2009/0076254 A1 | 3/2009 | Behan et al. |

(56) References Cited

U.S. PATENT DOCUMENTS

| | | |
|---|---|---|
| 2009/0186895 A1 | 7/2009 | Teegarden et al. |
| 2009/0197935 A1 | 8/2009 | Teegarden et al. |
| 2009/0298841 A1 | 12/2009 | Ahmed et al. |
| 2010/0004264 A1 | 1/2010 | Xiong et al. |
| 2010/0041672 A1 | 2/2010 | Bruton et al. |
| 2010/0069367 A1 | 3/2010 | Boren et al. |
| 2010/0226855 A1 | 9/2010 | Nangia et al. |
| 2010/0240653 A1 | 9/2010 | Santora et al. |
| 2010/0267691 A1 | 10/2010 | Chuang et al. |
| 2010/0305107 A1 | 12/2010 | Ahmed et al. |
| 2011/0021538 A1 | 1/2011 | Krishnan et al. |
| 2011/0178094 A1 | 7/2011 | Holm et al. |
| 2011/0207790 A1 | 8/2011 | Carlos et al. |
| 2011/0207791 A1 | 8/2011 | Selvey et al. |
| 2011/0237792 A1 | 9/2011 | Ahmed et al. |
| 2011/0263592 A1 | 10/2011 | Xiong et al. |
| 2012/0088785 A1 | 4/2012 | Rich |
| 2013/0172379 A1 | 7/2013 | Rich |
| 2013/0172398 A1 | 7/2013 | Rich |
| 2013/0217700 A1 | 8/2013 | Xiong et al. |
| 2013/0237541 A1 | 9/2013 | Teegarden et al. |
| 2014/0073681 A1 | 3/2014 | Schmidt et al. |
| 2014/0142140 A1 | 5/2014 | Bird |
| 2014/0349976 A1 | 11/2014 | Hacksell et al. |
| 2015/0031897 A1 | 1/2015 | Rich |
| 2015/0045372 A1 | 2/2015 | Krishnan et al. |
| 2015/0073141 A1 | 3/2015 | Teegarden et al. |
| 2015/0210648 A1 | 7/2015 | Carlos et al. |
| 2015/0233698 A1 | 8/2015 | Huang et al. |
| 2015/0320742 A1 | 11/2015 | Chuang et al. |
| 2016/0067216 A1 | 3/2016 | Selvey et al. |
| 2016/0075660 A1 | 3/2016 | Xiong et al. |
| 2016/0324851 A1 | 11/2016 | Friedhoff et al. |
| 2016/0324852 A1 | 11/2016 | Friedhoff et al. |
| 2017/0014385 A1 | 1/2017 | Friedhoff et al. |

FOREIGN PATENT DOCUMENTS

| | | |
|---|---|---|
| DE | 102004061593 | 6/2006 |
| EP | 0030023 A2 | 6/1981 |
| EP | 0 371 431 | 6/1990 |
| EP | 0605981 B1 | 2/1996 |
| EP | 0818449 A1 | 1/1998 |
| EP | 0631176 B1 | 12/2000 |
| EP | 1108 720 | 6/2001 |
| EP | 0867477 B1 | 5/2002 |
| EP | 1558 582 | 12/2005 |
| EP | 1683 516 | 7/2006 |
| EP | 1695966 A1 | 8/2006 |
| EP | 1734039 | 12/2006 |
| EP | 1667975 B1 | 11/2007 |
| EP | 1497266 B1 | 6/2008 |
| EP | 1824830 B1 | 7/2010 |
| EP | 1727803 B1 | 3/2012 |
| EP | 1956004 B1 | 6/2012 |
| EP | 2120950 B1 | 7/2012 |
| EP | 2190844 B1 | 4/2013 |
| EP | 2066641 B1 | 6/2014 |
| FR | 2 722 369 | 1/1996 |
| GB | 1147379 | 12/1967 |
| GB | 2341549 A | 3/2000 |
| JP | 02262627 | 10/1990 |
| JP | 2001-244773 A | 9/2001 |
| JP | 2005-531518 A | 10/2005 |
| JP | 04334357 B2 | 3/2010 |
| WO | WO 95/11592 A1 | 5/1995 |
| WO | WO 96/02138 | 2/1996 |
| WO | WO 96/10559 | 4/1996 |
| WO | WO 96/23783 | 8/1996 |
| WO | WO 96/32931 | 10/1996 |
| WO | WO 97/03967 | 2/1997 |
| WO | WO 97/32858 A1 | 9/1997 |
| WO | WO 97/45111 | 12/1997 |
| WO | WO 98/24785 | 6/1998 |
| WO | WO 98/27081 A1 | 6/1998 |
| WO | WO 98/47874 A1 | 10/1998 |
| WO | WO 98/54157 A1 | 12/1998 |
| WO | WO 98/54158 A1 | 12/1998 |
| WO | WO 98/57931 A2 | 12/1998 |
| WO | WO 98/57952 A1 | 12/1998 |
| WO | WO 99/06354 | 2/1999 |
| WO | WO 99/32436 | 7/1999 |
| WO | WO 99/32463 | 7/1999 |
| WO | WO 99/32927 | 7/1999 |
| WO | WO 99/42465 A2 | 8/1999 |
| WO | WO 99/47516 A1 | 9/1999 |
| WO | WO 99/52927 | 10/1999 |
| WO | WO 99/65906 A1 | 12/1999 |
| WO | WO 00/12073 A1 | 3/2000 |
| WO | WO 00/13681 | 3/2000 |
| WO | WO 00/34265 A2 | 6/2000 |
| WO | WO 00/42026 A1 | 7/2000 |
| WO | WO 00/57877 | 10/2000 |
| WO | WO 00/58303 A1 | 10/2000 |
| WO | WO 00/58313 A1 | 10/2000 |
| WO | WO 00/63203 A1 | 10/2000 |
| WO | WO 00/64866 | 11/2000 |
| WO | WO 00/64877 A1 | 11/2000 |
| WO | WO 01/07436 | 2/2001 |
| WO | WO 01/16108 A2 | 3/2001 |
| WO | WO 01/17963 A2 | 3/2001 |
| WO | WO 01/21160 | 3/2001 |
| WO | WO 01/29008 | 4/2001 |
| WO | WO 01/29008 A | 4/2001 |
| WO | WO 01/32646 A2 | 5/2001 |
| WO | WO 01/32660 A1 | 5/2001 |
| WO | WO 01/40217 A1 | 6/2001 |
| WO | WO 01/46166 | 6/2001 |
| WO | WO 01/64676 | 9/2001 |
| WO | WO 01/98279 A2 | 12/2001 |
| WO | WO 02/08178 A1 | 1/2002 |
| WO | WO 02/20489 A2 | 3/2002 |
| WO | WO 02/28837 A1 | 4/2002 |
| WO | WO 02/36562 A2 | 5/2002 |
| WO | WO 02/39987 | 5/2002 |
| WO | WO 02/44170 A2 | 6/2002 |
| WO | WO 02/051833 | 7/2002 |
| WO | WO 02/076464 | 10/2002 |
| WO | WO 02/078693 A2 | 10/2002 |
| WO | WO 02/089811 A1 | 11/2002 |
| WO | WO 02/098857 A1 | 12/2002 |
| WO | WO 02/102774 A1 | 12/2002 |
| WO | WO 03/002097 | 1/2003 |
| WO | WO 03/011284 A1 | 2/2003 |
| WO | WO 03/013510 A1 | 2/2003 |
| WO | WO 03/014097 A1 | 2/2003 |
| WO | WO 03/020707 A1 | 3/2003 |
| WO | WO 03/035061 A1 | 5/2003 |
| WO | WO 03/037872 A1 | 5/2003 |
| WO | WO 03/062206 | 7/2003 |
| WO | WO 03/066056 A1 | 8/2003 |
| WO | WO 03/072558 A2 | 9/2003 |
| WO | WO 03/080580 A2 | 10/2003 |
| WO | WO 03/080608 A2 | 10/2003 |
| WO | WO 03/095434 A1 | 11/2003 |
| WO | WO 03/104193 A1 | 12/2003 |
| WO | WO 2004/000828 | 12/2003 |
| WO | WO 2004/026830 A1 | 4/2004 |
| WO | WO 2004/026831 A1 | 4/2004 |
| WO | WO 2004/028450 | 4/2004 |
| WO | WO 2004/035047 A1 | 4/2004 |
| WO | WO 2004/041792 A1 | 5/2004 |
| WO | WO 2004/045118 | 5/2004 |
| WO | WO 2004/046110 | 6/2004 |
| WO | WO 2004/050085 A1 | 6/2004 |
| WO | WO 2004/058722 | 7/2004 |
| WO | WO 2004/071426 | 8/2004 |
| WO | WO 2004/074243 A2 | 9/2004 |
| WO | WO 2004/078176 A1 | 9/2004 |
| WO | WO 2004/080969 A1 | 9/2004 |
| WO | WO 2004/085433 | 10/2004 |
| WO | WO 2004/096771 | 11/2004 |
| WO | WO 2005/012254 | 2/2005 |
| WO | WO 2005/021530 A1 | 3/2005 |

(56) References Cited

FOREIGN PATENT DOCUMENTS

| | | |
|---|---|---|
| WO | WO 2005/021545 A | 3/2005 |
| WO | WO 2005/026125 A1 | 3/2005 |
| WO | WO 2005/030724 A2 | 4/2005 |
| WO | WO 2005/040124 A1 | 5/2005 |
| WO | WO 2005/066157 A1 | 7/2005 |
| WO | WO 2005/077345 | 8/2005 |
| WO | WO 2005/095346 A1 | 10/2005 |
| WO | WO 2005/103011 | 11/2005 |
| WO | WO 2005/113539 A1 | 12/2005 |
| WO | WO 2005/121140 A1 | 12/2005 |
| WO | WO 2006/018662 | 2/2006 |
| WO | WO 2006/038006 A2 | 4/2006 |
| WO | WO 2006/049734 | 5/2006 |
| WO | WO 2006/049941 | 5/2006 |
| WO | WO 2006/053785 A1 | 5/2006 |
| WO | WO 2006/055734 | 5/2006 |
| WO | WO 2006/059149 | 6/2006 |
| WO | WO 2006/060654 | 6/2006 |
| WO | WO 2006/070394 | 7/2006 |
| WO | WO 2006/076592 | 7/2006 |
| WO | WO 2006/078610 | 7/2006 |
| WO | WO 2006/079637 | 8/2006 |
| WO | WO 2006/081335 | 8/2006 |
| WO | WO 2006/086705 | 8/2006 |
| WO | WO 2006/089871 | 8/2006 |
| WO | WO 2006/095205 | 9/2006 |
| WO | WO 2006/097766 | 9/2006 |
| WO | WO 2006/100519 | 9/2006 |
| WO | WO 2006/112464 | 10/2006 |
| WO | WO 2006/116614 | 11/2006 |
| WO | WO 2007/002559 | 1/2007 |
| WO | WO 2007/026959 | 3/2007 |
| WO | WO 2007/039219 A1 | 4/2007 |
| WO | WO 2007/039220 A1 | 4/2007 |
| WO | WO 2007/039238 A1 | 4/2007 |
| WO | WO 2007/041409 | 4/2007 |
| WO | WO 2007/120600 | 10/2007 |
| WO | WO 2007/129111 | 11/2007 |
| WO | WO 2007 /136680 | 11/2007 |
| WO | WO 2007/136689 | 11/2007 |
| WO | WO 2007/136703 | 11/2007 |
| WO | WO 2007/136875 | 11/2007 |
| WO | WO 2007/147883 A1 | 12/2007 |
| WO | WO 2008/027483 | 3/2008 |
| WO | WO 2008/042388 | 4/2008 |
| WO | WO 2008/054748 | 5/2008 |
| WO | WO 2008/113818 A1 | 9/2008 |
| WO | WO 2009/023253 | 2/2009 |
| WO | WO 2009/074607 A1 | 6/2009 |
| WO | WO 2009/123714 | 10/2009 |
| WO | WO 2010/062321 | 6/2010 |
| WO | WO 2010/062323 | 6/2010 |
| WO | WO 2014/065437 | 5/2014 |
| WO | WO 2014/085362 | 6/2014 |
| WO | WO 2015/012554 | 1/2015 |
| WO | WO 2017/044767 | 1/2017 |

OTHER PUBLICATIONS

"QuaSAR" Research Monograph 22, 1978, NIDA, Barnett and Willette (eds.) See pp. 16-25 pp. 159-179, Tables 1-8.
Adams et al; "Antithrombotic and Vascular effects of AR246686, a novel 5-HT2A receptor antagonist" 2007 EJM, nn. 1-22.
Affolter, H., "CA2+ as Messenger of5HT2-Receptor Stimulation in Human Blood Platelets," Naunyn Schmiedebergs Arch. Pharmacol., 1984, vol. 325(4), 337-42.
Al-Shamma et al., "Nelotanserin, a Novel Selective Human 5-Hydroxytryptamine 2A Inverse Agonist for the Treatment of Insomnia," J Pharmacol. Exp. Ther., 2009, 332:281-290.
Al-Shamma et al; "The Selective Serotonin 5HT2A Inverse Agonist APD125 Promotes Sleep Onset and Consolidation in Male Wistar Rats During the Normal Active Phase" 2004 APSS.
Al-Shamma; "APD125: A 5-HT2A Inverse Agonist for the Treatment of Sleep Maintenance Insomnia" 2008 DDST; DD. 1-7.

Al-Shamma; "The Selective Serotonin 5HT2A Inverse Agonist APD125 Promotes Sleep Onset and Consolidation" Jun. 22, 2005 APSS, DD. 1-5.
Andrzejewska-Buczko Jr. et al., Klin. Oczna, 98(2), 101-4, 1996.
Anonymous, Br. Med. J, 298: 424-430, 1989.
Antinori et al., Neurology, 48:687-694, 1997.
Barluenga, Jr. et al., "A New and Specific Method for the Monomethylation of Primary Amines," J Chem. Soc. Chem. Commun., 1984,20, 1334-1335.
Batey, R.A. et al., "An Efficient New Protocol for the Formation of Unsymmetrical Tri- and Tretrasubstituted Ureas," Tetra. Lett., 1998, 39, 6267-6270.
Berge et al., "Pharmaceutical salts", J. of Pharmaceutical Sciences (1977) 66(1):1-19.
Berger and Major, Seminars and Neurology, 19:193-200, 1999.
Bernatowicz, M. et al., "A Comparison of Acid Labile Linkage Agents for the Synthesis of Peptide C-Terminal Amides," Tetra. Lett., 1989, 30(35), 4645-4648.
Blier, P. et al., "Putative mechanisms of action of antidepressant drugs in affective and anxiety disorders and pain," Journal of Psychiatry and Neuroscience, 2000, vol. 26(1), 37-43.
Bryn et al., Pharm. Res. V. 12 (1995), N. 7, p. 945-54.
Bryn, Solid-State Chemistry of Drugs, 2nd ed. (1999), Chapter 11—Hydrates and Solvates, 233-247.
Burger, A., "Isosterism and Bioisosterism in Drug Design", Prag. Drug Res., 37 (1991 ), pp. 287-371.
Burla et al., J Appl. Cryst., 38, 381, 2005.
Buysse et al., Psychiatry Research, 28(2), 193-213, 1989.
Cameron and Cotter, Naunyn Schmiedebergs Arch. Pharmacol., 367(6): 607-14, Jun. 2003.
Carter, H.E. et al., "Carbobenzoxy Chloride and Derivatives," Org. Syn. Coll., 1955, vol. 3, 167-169.
Casey et al., "Constitutively active mutant $5HT_{2A}$ serotonin receptors: inverse agonist activity of classical $5HT_{2A}$ antagonists", Society for Neuroscience Abstracts, vol. 22, p. 699 (1996).
Catalan, J. et al., "New Ultraviolet Stabilizers: 3- and 5-(2'-Hydroxyphenyl)pyrazoles," J Am. Chem. Soc., 114, 5039-5048 (1992).
Cazzola et al., "5-HT modifiers as a potential treatment of asthma", TIPS, 2000, vol. 21, p. 13.
Cazzola, M. and Matera, M.G., Trends Pharmacol. Sci. 21 :201-202, 2000.
Chambers, et al. Bioorg., Med. Chem. Lett. 2002, 12 1997-99. See p. 1997-98.
Chang et al., Shock, 24(4): 336-340, 2005.
Chang et al.,J Ocul.Pharmacol., 1:137-147, 1985.
Cohen-Mansfield J. and Billig, N., Agitated Behaviors in the Elderly. I.A. Conceptual Review,J Am. Geriatr. Soc. 34(10): 711-721, 1986.
Collier et al., "Radiosynthesis and in-vivo evaluation of the pseudopeptide 8-opioid antagonist [125]-ITIPP(\11)", J. Labeled Compd. Radiopharm., 1999, vol. 42, pp. S264-S266.
Collins et al., "N-Phenylamidines as Selective Inhibitors of Human Neuronal Nitric Oxide Synthase. Structure-Activity Studies and Demonstration of in Vivi Activity". Journal of Medicinal Chemistry, American Chemical Society, 41, No. 15,pp. 2858-2871, 1998:XP0022144154.
DeBie, J.J. et al., British J Pharm., 124:857-864, 1998.
Deuchar, G. et al.,Pulm. Pharmacol. Ther., 18(1):23-31, 2005.
Diagnostic and Statistical Manual of Mental Disorders, Fourth Edition, Text Revision: DSM-IV-TR, Washington, DC, American Psychiatric Association, 2000.
Dosa et al; "Solubilized phenyl-pyrazole ureas as potent, selective 5-HT2A inverse-agonists and their aDDlication as antiplatelet agents" 2010 BMCL; DD. 1-15.
Dosa et al; "Synthesis and SAR of Pyridinyl-Pyrazole Derivatives as Selective 5HT2A Inverse-Agonists for Platelet Aggregation" 2008 ACS, 235th ACS National Meeting, MEDI 44.
Dosa, P.I. et al., "Synthesis and SAR of Solubilized Pyrazole Derivatives as 5-HT2a Inverse-Agonists for Platelet Aggregration," 232th ACS National Meeting, Sep. 2006, MEDI-431, 1 page.
Elliott, J.M. et al., "4-0xospiro[benzopyran-2,4'-piperidines] as Class III Antiarrhythmic Agents. Pharmacological Studies on

(56) References Cited

OTHER PUBLICATIONS

3 ,4-Dihydro-1 '-]2-(benzofurazan-5-yl)-ethyl ]-6methane-sulfonamidospiro[(2H)-1-benzopyran-2,4'-piperidin]-4-one (L-691,121)", J Med. Chem., 35:3973-3976 (1992).
Elphick et al., Science, 306: 1380-1383, 2004.
Fujita, M. et al.,Am. Heart J 145:e16, 2003.
Fujiwara, T., and Chiba, S. Journal of Cardiovascular Pharmacology 26: 503-510, 1995.
Glennon, et al., J. Med. Chem., 1982, 25(10), 1163-68. Seep. 1166-67 and Table IL.
Greene et al., Protecting Groups in Organic Synthesis, 3rd Edition, 1999 (Wiley)*.
Griesser, The Importance of Solvates, in Polymorphism in the Pharmaceutical Industry; 211-23 3; Rolf Hilfzker, ed., 2006.
Grotewiel et al., "Receptors Exhibit Constitutive Activity that is Blocked by Inverse Agonists," Faseb J, Abstract 353, 8(7), May 21-25, 1994 (1 page).
Grunder et al., Time course of 5-HT2A receptor occupancy in the human brain after a single oral dose of the putative antipsychotic drug MDL 100,907 measured by positron emission tomography, Neuropsychopharmacology, Sep. 1997; 17(3): 175-85.
Guillory, "Generation of Polymorphs, Hydrates, Solvates, and Amorphous Solids, in Polymorphism in the Pharmaceutical Industry", 183-226, 202-209; Harry G. Britain, ed., 1999.
Gutsche, C.D. et al., "2-Phenylcycloheptanone," Org. Syn. Coll., 1963, vol. 4, 780-783.
Halberstadt et al., Neuropsychopharmacology (2009) 34, 1958-1967.
Hayashi, T. et al., Atherosclerosis 168: 23-31, 2003.
Herrick-Davis et al., "Activating mutations of the serotonin 5-HT2C receptor", J. Neurochem., Sep. 1997; 69(3):1138-44.
Herrick-Davis et al., "Constitutively active 5HT2C serotonin receptor created by site-directed mutagenesis", Society for Neuroscience Abstracts, vol. 22, p. 699 .18 (1996).
Higuchi et al., "Pro-drugs and Novel Delivery Systems", vol. 14 of the ACS Symposium Series; and in Bioreversible Carriers in Drug Design, ed. Edward B. Roche, American Pharmaceutical Association and Pergamon Press, 1987*.
Hittner et al; "A Selective 5-HT2A Receptor Inverse Agonist with Preclinical Antipsychotic Profile in Rats" 2000 NEURO.
Holtje, The Practice of medicinal Chemistry, 2nd ed., 2003, Wermuth (editor), Academic Press, pp. 387-403. Seep. 394.
Horibe, E., Circulation Research 68: 68-72, 2004.
ICSD-International Classification of Sleep Disorders: Diagnostic and Coding Manual: Diagnostic Classification SteerinR Committee, American Sleep Disorders Association, 1990.
Ieni, J. and Meyerson, L., "The 5-HT1A Receptor Probe [3H]8-OH-DPAT labels . . . ,"Life Sciences, 1988, vol. 42, 311-320.
Ikeguchi, K. and Kuroda, A., "Mianserin Treatment of Patients with Pyschosis Induced by Antiparkinsonian Drugs," Eur. Arch. Psych. Clin. Neurosci., 1995, 244, 320-324.
Jayakumar et al; "Synthesis and SAR of Alkoxyphenyl Pyrazole as 5-HT2A Inverse Agonists" 2006, ACS, 232$^{nd}$ ACS National Meeting, MEDI 430.
Jayakumar et al; "Synthesis and SAR of Substituted Diphenylamines as 5HT2A Inverse-Agonists" 2005 ACS, 229th ACS National Meeting, MEDI 049.
John Mandel, "Statistical Analysis of Experimental Data", Chapter 9, pp. 204-207, Toronto, Ontario, (1964).
John Mandel, "Statistical Analysis of Experimental Data", Chapter 3, pp. 28-57, Toronto, Ontario, (1964).
Julius, D. et al., "The 5HT2 Receptor Defines a Family of Structurally Distinct but Functionally Conserved Serotonin Receptors," Proc. Natl. Acad. Sci. USA, 1990, vol. 87, 928-932.
Kanayama, M. et al., J Neurosurg. Spine, 2:441-446, 2005.
Kaneniwa, et al., Solubilization of Water-Insoluble Organic Powders by Ball-Milling in the Presence of Polyvinylpyrrolidone; Chem. Pharm. Bull; 23(11) 2973-2986; 1975.
Katz, LR. et al., J Clin. Psychiatry, 60(2): 107-115, 1999.

Kitagawa, O. et al., "Beckmann Rearrangement of 0-4 Pentenyl Oxime through N-Bromosuccinimide-Mediated Activating Process", Chem. Pharm. Bull., 45(1) 32-35 (1997).
Konig, W. et al., "A New Method for Synthesis of Peptides: Activation of the Carboxyl Group with Dicyclohexylcarbodiimide using 1-Hydroxybenzotriazoles as Additives," Chem. Ber., 1970 103, 788-798 (English abstract included).
Koss E. et al., "Assessing patterns of agitation in Alzheimer's disease patients with the Cohen-Mansfield Agitation Inventory. The Alzheimer's Disease Cooperative Study", Alzheimer Dis. Assoc. Disord. 11(suDDL 2):S45-S50, 1997.
Krieger and Emre, Pediatr. Transplantation, 8:594-599, 2004.
Krystal et al; "The effects of APD125, a selective serotonin 5-HT2A, on sleep quality and sleep maintenance in a subjective study in patients with primary insomnia" 2009 SLEEP; DD. 1-23.
Landolt H.P. et al., Serotonin-2 Receptors and Human Sleep: Effect of Selective Antagonist on EEG Power Spectra, Neuropsvcho pharmacolo f!V, vol. 21(3):455-66, 1999.
Le Bas et al., "Radioiodinated analogs of EP 00652218 for the exploration of the tachykinin NK1 receptor by spect", J. Labeled Compd. Radiopharm., 2001, vol. 44:S280-S282.
Luthringer et al; "Pharmacokinetic and Pharmacodynamic Effects of the Selective 5HT2A Inverse Agonist APD125 in Healthy Adults" 2005 APSS.
Marchini, P. et al., "Sodium Borohydride-Carboxylic Acid Systems. Useful Reagents for the Alkylation of Amines," J Orf;;. Chem., 1975, 40(23), 3453-3456.
Marcos, E. et al., Circ. Res., 94(9): 1263-70, 2004.
Mastropasqua et al.,Acta. Ophthalmol. Scand. Suppl., 224:24-25, 1997.
Menzaghi et al; "ARI 16081, A Novel High Affinity 5-HT2A Receptor Inverse Agonist With In Vivo Efficacy" Nov. 1999 NEURO.
Menzaghi et al; "ARI 16081, A Novel Selective 5-HT2A Inverse Agonist as a Putative Atypical Antipsychotic: Comparative Studies with Clozapine and Haloperidol" 2000 CINP.
Menzaghi et al; "Identification of Novel Selective 5-HT2A Inverse Agonists as Putative Atypical Antipychotics Using Constitutively Activated Human 5-HT Receptors" Jun. 2000 AS PET.
Menzaghi et al; "Therapeutic Potential of Selective Serotonin 5HT2A Receptor Inverse Agonists: Pre-Clinical Evaluation of ARI 16081 as Anti psychotics in Rodents" 2002 FESN.
Miai, C., Clin. Exp. Pharmacol. Physiol., 30(3): 189-193, 2003.
Mizuki, Y. et al., "Effects of Mianserin on Negative Symptoms in Schizophrenia," Int. Clinical Psychopharmacolo5'Y, 1990,5: 83-95.
Morairty, et al.; Selective 5HT$_{2A}$ and 5HT$_6$ Receptor Antagonists Promote Sleep in Rats; Sleep; vol. 31,No. 1, 2008.
Morissette, et al., High-throughput Crystallization. Polymorphs, Salts, Co-crystals and Solvates of Pharmaceutical Solids, Advanced Dru£ Delivery Reviews, 56 (2004) 275-300.
Mueller, Ann. Thorac. Surg., 77:354-362, 2004.
Muto, T. et al., Mal. Cell. Biochem. 272: 119-132, 2005.
National Institute of Health, National Heart, Lung and Blood Institute, Insomnia Facts Sheet, Oct. 1995.
Newton, R.A. and Elliot, J.M., "Mianserin-Induced Down-Regulation of Human 5-Hydroxytryptamine2A and 5-Hydro . . . ,"Journal of Neurochemistry, 1997, 69: 1031-1038.
Nichols, et al. J. Med Chem, 1991, 34, 276-81. See p. 279.
Nishiyama, T.,Eur. J Pharmacol., 516:18-22, 2005.
Nomura et al., Blood Coagulation and Fibrinolysis 16: 423-428, 2005.
Otwinowski et al., Methods Enzymology, 1997, 276, 307.
Pawlak, D. et al., Thrombosis Research 90: 259-270, 1998.
Pietraszek, M.H. et al., Thrombosis Res. 66(6): 765-74, 1992.
Portegies et al., Eur. J Neural., 11:297-304,2004.
Prosser et al., "Selective serotonin 5-HT2A inverse agonists promote sleep consolidation in male Wistar rats during the normal inactive phase", #29, Arena Pharmaceuticals, Inc., APSS Meeting (Jun. 2004) 1 page.
Querbes et al., J Virology, 78:250-256, 2004.
Remington, *The Science of Pharmacy*, 20$^{th}$ Ed., 2000, Lippincott Williams & Wilkins, Editors: Gennaro, A.R. et al., 2000.

(56) References Cited

OTHER PUBLICATIONS

Rosenberg et al.; "APD125, a selective serotonin 5-HT(2A) receptor inverse agonist, significantly improves sleep maintenance in primary insomnia." Sleep (2008), 31(12), 1663-71.
Rosenberg et al; "APD125, a selective serotonin 5-HT2A receptor inverse agonist, significantly improves the key parameters of sleep maintenance in patients with primary insomnia" 2007 AASM.
Rosenberg et al; "APD125, a selective serotonin 5-HT2A receptor inverse agonist, significantly improves the key PSG parameters of sleep maintenance in patients with primary insomnia" 2008 APA; pp. 1-37.
Roth et al; "APD125, a selective serotonin 5-HT2A receptor inverse agonist, significantly improves the key parameters of sleep maintenance in patients with primary insomnia" 2008 APSS DD. 1-19.
Sahgal, A. (ed.), "Practical behavioural neuroscience: problems, pitfalls and suggestions," in Behavioral Neuroscience: A Practical Approach, IRL Press, New York, 1993, vol. 1, 1-8.
Satomura et al., "Sarpogrelate, a specific 5HT2-receptor antagonist, improves the coronary microcirculation in coronary artery disease", Clin. Cardiol. Jan. 2002; 25(1):28-32.
Sawnyok, J. et al., "Antidepressants as analgesics: an overview of central and peripheral mechanisms of action," Journal of Psvchiatrv and Neurosciences, 2001, vol. 26(1), 21-9.
Schmidt, C., "The Role of 5-HT2A Receptors in Antipsychotic Activity," Life Sciences, 1995, 56(25), 2209-2222.
Shan et al.; "Investigation of non-aqueous vehicles for a poorly soluble compound intended for softgel dosage form development". Abstract AAPS2005-000990, AAPS Journal, (2005).
Shan et al.; "Physicochemical characterization during salt selection process". Abstract AAPS2006-001961, AAPS Journal, (2006).
Shan et al.; "Physicochemical characterization during salt selection process". Abstract AAPS2005-000997, AAPS Journal, (2005).
Sharpley A.L., et al., "Slow Wave Sleep in Humans: Role of 5-HT$_{2A}$ and 5HT$_{2c}$ Receptors", Neuropharmacolo fzy, vol. 33(3/4):467-71, 1994.
Sheehan, J.C. et al., "1-Ethyl-3-(3 Dimethylamiono) Proplycarbodiimide Hydrochloride and Methiodide," Or£. Svn. Coll., 1973, vol. 5, 555-558.
Shibata, R. et al., "Adiponectin protects against myocardial ischemiareperfusion injury through AMPK- and COX-2 dependent mechanisms," Nature Medicine, advanced online Publications: pp. 1-8, Published Online Sep. 11, 2005.
Silva, A., J Pharmacol., 518(2-3): 152-7, 2005.
Singh et al., Transplantation, 69:467-472, 2000.
Smith et al., Test-retest variability of serotonin 5-HT2A receptor binding measured with positron emission tomography and [18F]altanserin in the human brain, Synapse, Dec. 1998; 30(4):380-92.
Sorenson et al., "Characterization of the 5-HT2 Receptor Antagonist MDL 100907 as Putative Atypical Antipsychotic: Behavioral, Electrophysiological and Neurochemical Studies," J Pharacol. Exp. Ther., 1993 266(2), 684-691.
Speer, et al.; "Influence of digestive enzymes on dissolution of a poorly water soluble compound from cross-linked gelatin capsules in sodium lauryl sulfate medium". Abstract AAPS2005-000998, AAPS Journal, (2005).
Speer, et al; "Intrinsic dissolution characterization of different morphic forms of a poorly water soluble compound". Abstract AAPS2006-002324, AAPS Journal, (2006).
Staley et al., Comparison of [(18)F] altanerin and [(18)F]durteroaltanserin for PET imaging of serotonin (2A) receptors in baboon brain: pharmacological studies, Nucl Med Biol, Apr. 2001; 28(3):271-9.
Storey, R., et al. "Automation of Solid Form Screening Procedures in the Pharmaceutical Industry—How to Avoid the Bottlenecks", Crystallography Reviews, 2004, vol. 10,No. 1,DD.45-56.
Strah-Pleynet, et al.; "5-HT2A Receptor inverse-agonists: Design and structure-activity relationship of novel pyrazole derivatives". Abstracts of Papers, 231st ACS National Meeting, Atlanta, GA, United States, Mar. 26-30, 2006 (2006), MEDI-145.
Strah-Pleynet, et al.; "Bioisosteric modifications of urea derivatives as 5-HT2A inverse-agonists" Abstracts of Papers, 229th ACS National Meeting, San Diego, CA, United States, Mar. 13-17, 2005 (2005), MEDI-042.
Strah-Pleynet, et al.; "Discovery and SAR of novel 5HT2A receptor inverse-agonists". Abstracts of Papers, 227th ACS National Meeting, Anaheim, CA, United States, Mar. 28-Apr. 1, 2004 (2004), MEDI-270.
Street et al., "Olanzapine treatment of psychotic and behavioral symptoms in patients with Alzheimer disease in nursing care facilities: a double-blind, randomized, placebo-controlled trial. The HGEU Study Group", Arch Gen Psychiatry, Oct. 2000; 57(10):968-76.
Takahashi, T. et al., Diabetes. Res. Clin. Pract., 58(2): 123-9, Nov. 2002.
Takenaka et al., "The effect of anplag (sarpogrelate HCl), novel selective 5-HT 2 antagonist on intraocular pressure in glaucoma patients", Investig Ophthalmol Vis Sci, 36(4):S724 (3390-377) 1995.
Talvik-Lotfi et al., "High 5HT2A receptor occupancy in M100907-treated schizophrenic patients", Phychopharmacology (2000) 148:400-403.
Tang, et al. "Anilinopyrazole as selective CDK2 inhibitors: design, synthesis, biological evaluation, and x-ray crystallographic analysis", Bioorg. Med. Chem. Lett. 13, 2985-88 (2003).
Teegarden et al., "Discovery of 1-[3-(4-Bromo-2-methyl-2H-pyrazol-3-yl)-4-methoxyphenyl]-3-(2,4-difluorophenyl(urea(Nelotanserin) and Related 5-Hydroxytryptamine2A Inverse Agonists for the Treatment ofInsomnia", J Med. Chem. 2003, vol. 53, pp. 1923-1936.
Teegarden etal.; "5-HT2A inverse-agonists for the treatment of insomnia" Current Topics in Medicinal Chemistry, (2008), 8(11), 969-976.
The International Classification of Sleep Disorders, Revised Diagnostic and Coding Manual, American Academy of Sleep Medicine (2001) pp. 1-336 (also includes table of contents and glossary).
Topliss, John G. "A Manual Method for Applying the Hansch Approach to Drug Design", Journal of Medicinial Chemistry, vol. 20, No. 4, pp. 463-469, 1997.
Van Zwieten, PA, "Receptors Involved in the Regulation of Vascular Tone," Arzneimittelforschung. 1985, vol. 35(12A): 1904-9.
Verstraete, M., "Prevention of atherosclerotic complications: controlled trial of ketanserin," British Medical Journal, 1989, vol. 298, 424-30.
Vikenes, K. et al., "Serotonin is associated with coronary artery disease and cardiac events," Circulation, 1999, vol. 100, 483-9.
Vippagunta, S. et al., "Crystalline solids," Advanced Drug Delivery Reviews, 48:3-26 (2001).
Westkaemper et al., Curr. Topics Med. Chem. 2002, 2, 575-598.
White, E., "Deamination of Amines. 2-Phenylethyl Benzoate via the Nitrosoamide Decomposition," Org. Syn. Coll., 1973, vol. 5, 336-339.
Wikstrom, H. et al., "Synthesis and Pharmacological Testing of 1, 2, 3, 4, 10, 14b-Hexahydro-6-methoxy . . . ," J Med. Chem., 2002, vol. 45, 3280-3285.
Wilson, H.C. et al., Thromb. Haemost., 2:66(3):355-60, Sep. 2, 1991.
Winokur A. et al., Acute Effects of Mirtazapine on Sleep Continuity and Sleep Architecture in Depressed Patients: A Pilot Study, Soc. of Biol. Psych., vol. 48:75-78, 2000.
Xiong et al; "Discovery and SAR of Highly Selective 5-HT2A Receptor Subtype Inverse-Agonists for Inhibition of Platelet Aggregation" 2008 ACS, 235$^{T}$ National Meeting, MEDI 45.
Xiong et al; "Synthesis and in Vivo Evaluation of Phenethylpiperazine Amides: Selective 5-Hydroxytryptamine2A Receptor Antagonists for the Treatment of Insomnia", Journal of Medical Chemistry, 2010, vol. 53, 5696-5706 JMC.
Yamada et al., Clin. Diagn. Viral., 1:245-256, 1993.
Yamashita, T. et al., Haemostatis 30:321-332, 2000.
Yevich et al. Curr. Med. Chem., 1997, 45(5), 295-312. Seep. 302.
Zhu et al., "Synthesis and mode of action of [$^{125}$I]- and $^3$H-labeled Thieno-2,3-c]pyridine antagonists of cell adhesion molecule expression", J. Org. Chem., (200) 67:943-8.

(56) References Cited

OTHER PUBLICATIONS

"The Merck Manual of Diagnosis and Therapy", Merck Research Laboratories, pp. 1769-1781 (2006).
Ahmed et al., "Bicylic heteroarylpiperazines as selective brain penetrant 5-HT6 receptor antagonists," (2005) *Bioorganic & Medicinal Chem. Letters*, 15:4867-4871.
Al-Shamma et al; "The Selective Serotonin $5HT_{2A}$ Inverse Agonist APD125 Promotes Sleep Onset and Consolidation in Male Wistar Rats During the Normal Active Phase," 1994 APSS Slides, 1-5.
Ancelin, et al. "Non-degenerative mild cognitive impairment in elderly people and use of anticholinergic drugs: longitudinal cohort study" (Feb. 1, 2006) *BMJ*, doi : 10.1136/bmj.38740.439664.DE.
Anonymous "Drug treats severe Alzheimer's". http://newsvote.bbc.co.uk/mpapps/pagetools/print/news.bbc.co.uk/2/hi/health/4832574.stm. Mar. 23, 2006.
ARICEPT® Label Jul. 2015.
Aschenbrenner et al., Drug Therapy in Nursing, 2009, TOC.
Bentley et al. "$5-HT_6$ Antisense Oligonucleotide I.C.V. Affects Rat Performance in the Water Maze and Feeding" (1997) *Journal of Psychopharma. (Supplement)* A64:255 (abstract).
Bentley et al. "Effect of the 5-HT6 Antagonist, Ro 04-6790 on Food Consumption in Rats Trained to a Fixed Feeding Regime" (1999) *British Journal of Pharmacol.* 126(Suppl.):66 (abstract).
Bentley et al., "Investigation of stretching behavior induced by the selective 5-HT6 receptor antagonist, Ro 04-6790, in rats" (1999) *British Journal of Pharmacol.* 126:1537-1542.
Birks et al. "Donepezil for dementia due to Alzheimer's disease", The Cochrane Library. http://onlinelibrary.wiley.com/store/10.1002/14651858.CD001190.pub2/asset/CD001190.pdf?v=1&t=h5uxf9xk&s=991bffcda40d23d5edf561ab6543198f531af16d [retrieved Aug. 14, 2012).
Bos et al. "5-HT6 receptor antagonists" lead optimization and biological evaluation of N-aryl and B-heteroaryl 4-amino-benzene sulfonamides (2001) *Eur. I Med. Chem.* 36(2): 165-178.
Bourson et al. "Determination of the Role of the 5-HT6 Receptor in the Rat Brain: A Study Using Antisense Oligonucelotides" (1995) *The Journal of Pharmacology & Experimental Therapeutics* 274(1): 173-180.
Bourson et al. "Involvement of 5-HT6 receptors in nigro-striatal function in rodents" (1998) *British J. of Pharmacol.* 125:1562-1566.
Branchek et al. "5-HT6 Receptors as Emerging Targets for Drug Discovery" (2000) *Annu. Rev. Pharmcol. Toxicol.* 40: 319-334.
Bromidge et al. "Phenyl Benzenesulfonamides are Novel and Selective 5-HT6 Antagonists: Identification of N-(2,50Dibromo-3-fluorophenyl)-4-methoxy-3-piperazin-1-ylbenzensulfonamide (SB-357134)" (2001) *Bioorganic & Medicinal Chemistry Letters* 11:55-58.
Callahan et al. "Characterization of the Selective 5-HT6 Receptor Antagonist SB 271046 in Behavioral Models of Cognition", $34^{th}$ Annual Scientific Meeting of the Soc. for Neurosci., San Diego. Oct. 2004.
Campbell et al. "Use of anticholinergics and the risk of cognitive impairment in an African American population" (2010) *Neurology* 75:152-159.
Carnahan et al. "The Concurrent Use of Anticholinergics and Cholinesterase Inhibitors: Rare Event or Common Practice?" (2004) JAGS 52(12):2082-2087 (abstract).
Castaneda-Corral et al. "Role of Peripheral and Spinal 5-HT6 Receptors According to the Rat Formalin Test" (2009) *Neuroscience* 162:444-452.
Chang-Fong et al. "1,2,3,4-Tetrahydrocarbazoles as 5-HT6 serotonin receptor ligands" (2004) *Bioorg. Med. Chem. Lett.* 14(8):1961-1964.
Chew et al. "Serum Anticholinergic Activity and Cognition in Patients with Moderate-to-Severe Dementia" (Jun. 2005) *Am J Geriatr Psychiatry* 13:6 (abstract).

Chuang et al. "5-HT6 Receptor Antagonist SB-742457 as a Novel Cognitive Enhancing Agent for Alzheimer's Disease" (2006) *Alzheimer's & Dementia, The Journal of the Alzheimer's Association*, 2(3/Supp. 1):S631-S632.
Clinical Trial Protocol Summaries (Five studies). http://www.gsk-clinicalstudyregister.com/quick-search-list.jsp?item=SB742457&type=Compound&letterrange=Q-U&studyType=All&phase=All&population=All&marketing=All (accessed Mar. 9, 2012).
Cooke "Glycopyrrolate in Bladder Dysfunction", Jan. 1, 1983 *South African Medical Journal* 63(1):3 (abstract).
Cuvposa glycopyrrolate oral solution Product Information Sheet, Rev. Jul. 2010.
Database Beilstein [Online] Beilstein Institute for Organic Chem., Frankfurt-Main, DE; XP002535545 Database Accession No. 5926580 (BRN), the whole document.
Davies et al. "Drug discovery targets: $5-HT_6$ receptor" (2005) *Drugs of the Future* 30(5):479-495.
Defilippi et al. "Drug Interactions with Cholinesterase Inhibitors" (2003) *Drugs Aging* 20(6):437-444 (abstract).
Douaud et al. "Preventing Alzheimer's disease-related gray matter atrophy by B-vitamin treatment" (2013) *PNAS* 110:9523-9528.
Drinka "Antimuscarinic Drugs for Overactive Bladder and Their Potential Effects on Cognitive Function in Older Patients" 2006 *JAGS* 54(6):1004-1005 (abstract).
East et al. "5HT6 receptor binding sites in schizophrenia and following antipsychotic drug administration: Autoradiographic studies with 125ISB-258585" (2002) *Synapse* 45:191-199.
Edwards et al. "Risk of delirium with concomitant use of tolterodine and and acetycholinesterase inhibitors". 2002 *J Amer Geriatric Society* 50(6):1165-1166 (abstract).
European Search Report for EP05025004.2 dated Jun. 30, 2006.
European Search Report for EP08157490.7 dated Jul. 8, 2008.
European Search Report for EP12170019.9 dated Aug. 16, 2012.
Ferguson "Modulation of lymphatic smooth muscle contraction responses by the endothelium" (1992) *Journal of Surgical Research* 52:359-363 (abstract).
File "Anxiolytic Action of a Neurokinin, Receptor Antagonist in the Social Interaction Test" (Nov. 1997) *Pharmacol. Biochem. Behav.* 58(3):747-752.
File "The Use of Social Interaction as a Method for Detecting Anxiolytic Activity of Chlordiazepoxide-llike Drugs" (Jun. 1980) *J Neuro. Methods* 2(3):219-238.
Foley et al. "The 5-HT6 Receptor Antagonist SB-271046 Reverses Scopolamine-Disrupted Consolidation of a Passive Avoidance Task and Ameliorates Spatial Task Deficits in Aged Rats" (2004) *Neuropsychopharmacology* 29:93-100.
Fullerton et al. "A phase 2 clinical trial of PF-05212377 (SAM-760) in subjects with mild to moderate Alzheimer's Disease with existing neuropsychiatric symptoms on a stable daily dose of Donepezil" Pfizer AAIC 2016 Poster Presentation, Cambridge, MA.
Garcia-Alloza et al. "Differential Involvement of 5-HT IB/ID and 5-HT6 Receptors in Cognitive and Non-cognitive Symptoms in Alzheimer's Disease" (2004) *Neuropsychopharmacology* 29:410-416.
Gardner "Distress Vocalization in Rat Pups a Simple Screening Method for Anxiolytic Drugs" (Nov. 1985) *J. Pharma. Meth.* 14(3):181-187 (Nov. 1985).
Geldmacher "Donepezil (Aricept®) for treatment of Alzheimer's disease and other dementing conditions" (2004) *Expert Rev. Neurotherapeutics* 4(1):5-16.
Gill et al. "A Prescribing Cascade Involving Cholinesterase Inhibitors and Anticholinergic Drugs" (2005) *Arch Intern Med* 165:808-813.
Gish et al. "Memorandum: Age-dependent manifestations of central anticholinergic effects" Department of Health and Human Services Public Health Service Food and Drug Administration Center for Drug Evaluation and Research, Mar. 5, 2007.
Glaxosmithkline Clinical Trial, http://www.gsk-clinicalstudyregister.com/result_comp_list.jsp?compound=SB742457&studyType=All&phase=All&population=All&marketing=All. Sep. 21, 2011.
Glaxosmithkline Pharmacology Study Report—A study in healthy volunteers to characterise [$^{11}$C]GSK215083A as a positron emission

(56) References Cited

OTHER PUBLICATIONS tomography (PET) tracer ligand for the 5-HT$_6$ receptor and to assess the occupancy at the 5-HT$_6$ receptor of SB-742457 in the brain using PET and a tracer dose of [$^{11}$C]GSK215083A (Sep. 24, 2009).
Glaxosmithkline, A Dose Ranging Study to Investigate the Efficacy and Safety of SB-742457 in Alzheimer's Disease NCT ID No. NCT00224497 (Verified 2007) Clinical Study.
Glaxosmithkline, SB-742457 and Donepezil in Alzheimer's Disease. NCT ID No. NCT00348192 (2006) Clinical Study.
Glennon et al. "2-Substituted Tryptamines: Agents with Selectivity for 5-HT6 Serotonin Receptors" (2000) *J. Med. Chem.*, 43: 1011-1018.
Gottlieb et al. "NMR Chemical Shifts of Common Laboratory Solvents as Trace Impurities" (1997) *J. Org. Chem.* 62:7512-7515.
Guy "Clinical Global Impression (CGI)—Severity of Depression Rating Scale" ECDEU Assessment Manual for Psychopharmacology (Rev. Ed. U.S. Dept. of Health, Education and Welvare, Bethesda, MD 1976).
Hamilton "A Rating Scale for Depression" (1960) *J. Neurol. Neurosurg. Psychiat.* 23:56-62.
Hamilton "Development of a Rating Scale for Primary Depressive Illness" (Dec. 1967) *Br. I Clin. Psych.* 6(4):278-296.
Hashimoto et al. "Urinary Incontinence: an Unrecognised Adverse Effect with Donepezil" (Aug. 12, 2000) *The Lancet* 356:568 (abstract).
Helm et al. "GABAb receptor antagonist SGS742 improves spatial memory and reduces protein binding to the cAMP response element (CRE) in the hippocampus" (2005) *Neuropharmacology* 48:956-964.
Hirst et al. "Characterization of [25I]-SB-258585 binding to human recombinant and native 5-HT6 receptors in rat, pig and human brain tissue" (2000) *British Journal of Pharmacology* 130:1597-1605.
Hirst et al. "Differences in the Central Nervous System Distribution and Pharmacology of the Mouse 5-Hydroxytryptamine-6 Receptor Compared with Rat and Human Receptors Investigated by Radioligand Binding, Site-Directed Mutagenesis, and Molecular Building" (2003) *Mol. Pharmacol.* 64:1295-1308.
Holenz et al. "Medicinal Chemistry Driven Approaches Toward Novel and Selective Serontonin 5-HT6 Receptor Ligands" (2005) *J. Med. Chem.* 48(6):1781-1795.
Ibach et al. "Acetylcholinesterase Inhibition in Alzheimer's Disease" (2004) *Current Pharmaceutical Design* 10:231-251.
Iliff et al. "A Paravascular Pathway Facilitates CSF Flow Through the Brain Parenchyma and the Clearance of Interstitial Solutes, Including Amyloid β." (2012) *Sci. Transl. Med.* 4(147):147ra111.
International Preliminary Report on Patentability for International Application No. PCT/US2005/041726 dated Sep. 21, 2006 by Authorized Officer Stefan Hartinger.
International Preliminary Report on Patentability for International Application No. PCT/US2007/011810 dated Jul. 16, 2008 by Authorized Officer Bart De Jong.
International Preliminary Report on Patentability; PCT/US2007/021182 dated Nov. 4, 2008 by Authorized Officer P. Lauro.
International Search Report and Written Opinion for PCT/EP008/067225 dated Mar. 23, 2009.
International Search Report and Written Opinion for PCT/EP2004/010843 dated Mar. 14, 2005.
International Search Report and Written Opinion for PCT/EP2005/012463 dated Feb. 20, 2006.
International Search Report and Written Opinion for PCT/EP2006/009460 dated Dec. 14, 2006.
International Search Report and Written Opinion for PCT/EP2008/053285 dated Jul. 29, 2008.
International Search Report and Written Opinion for PCT/US2004/023488 dated Oct. 12, 2004.
International Search Report and Written Opinion for PCT/US2004/023880 dated Nov. 15, 2004.
International Search Report and Written Opinion for PCT/US2007/021182 dated Mar. 14, 2005.
International Search Report and Written Opinion for PCT/US2008/009740 dated Feb. 18, 2009.
International Search Report and Written Opinion for PCT/US2009/005811 dated Jul. 8, 2010.
International Search Report and Written Opinion for PCT/US2009/005809 dated Apr. 28, 2010.
International Search Report and Written Opinion for PCT/US2009/002019 dated Dec. 14, 2009.
International Search Report and Written Opinion for PCT/US2016/031359 dated Jul. 29, 2016.
International Search Report and Written Opinion for PCT/US2016/037090 dated Sep. 9, 2016.
International Search Report for International Application No. PCT/US2006/002721 dated Feb. 20, 2007.
International Search Report for International Application No. PCT/US2005/041726 dated May 18, 2006 by Authorized Officer Stefan Hartinger.
International Search Report for International Application No. PCT/US2006/001516 dated Jun. 7, 2006.
International Search Report for International Application No. PCT/US2007/011810 dated Oct. 30, 2007 by Authorized Officer Bart De Jong.
International Search Report for PCT/EP2003/003197 dated Dec. 11, 2003.
Isaac et al. "6-Bicyclopiperazinyl-1-arylsulfonylindoles and 6-Bicyclopiperidinyl-1-arylsulfonylindoles Derivatives as Novel, Potent, and Selective 5-HT6 Receptor Antagonists" (2000) *Bioorganic & Med. Chem. Letters* 10:1719-1721.
Janos et al. "Overactive bladder medicines and cognitive testing" (Nov. 2008) *Int J Clin Pract* 62(11):1637-1642 (abstract).
Jayakumar et al. "Synthesis and SAR of Novel-Phenyl-Pyrazole Urea derivatives" (2006) ACS, abstract.
Jayakumar et al; "Synthesis and SAR of Substituted Diphenylamines as 5HT2A Inverse-Agonists" (2004) ACS, meeting abstract.
Jeon et al. "The synthesis of a new pyrazolylimidazolinone via 1,3-dipolar cycloaddition reaction of N-methyl sydnone with methyl propiolate" (1998) *Bull. Korean Chem. Soc.* 19(7):725-726.
Jewart et al. "Cognitive, Behavioral and Physiological Changes in Alzheimer Disease Patients as a Function of Incontinence Medications" (Apr. 2005) *Am J Geriatr Psychiatry* 13(4):324-328 (abstract).
Jhee et al. "Centrally Acting Antiemetics Mitigate Nausea and Vomiting in Patients with Alzheimer's Disease Who Receive Rivastigmine" (Mar./Apr. 2002) *Clinical Neuropharmacology* 25(2):122-123 (abstract).
Johnell et al. "Concurrent Use of Anticholinergic Drugs and Cholinesterase Inhibitors" (2008) *Drugs Aging* 25(10):871-877 (abstract).
Johnson et al. "5-HT6 receptor antagonists: Prospects for the treatment of cognitive disorders including dementia" (2008) *Current Opinion in Drug Discovery and Development* 11(5): 642-654.
Kaduszkiewicz et al. "Cholinesterase inhibitors for patients with Alzheimer's disease: systematic review of randomised clinical trials" (2005) *BMJ online* 331-321.
Kan et al. "Association of the HTR6 Polymorphism C267T With Late-Onset Alzheimer's Disease in Chinese" (1995) *J. Pharmacol. & Exp. Therapeutics* 274:173-180.
Kay et al. "Antimuscarinic Drugs for Overactive Bladder and Their Potential Effects on Cognitive Function in Older Patients" (2005) *JAGS* 53:2195-2201 (abstract).
Kay et al. "Preserving cognitive function for patients with overactive bladder: evidence for a differential effect with darifenacin" (Nov. 2008) *Int J Clin Pract.* 62(11):1792-1800.
Khoshkhoo et al. "Crystallization of polymorphs: the effect of solvent" (1993) *J. Phys. DD Appl.Phys.* 26:B90-B93.
Khullar et al. "Prevalence of Faecal Incontinence Among Women with Urinary Incontinence" (1998) *Br. J. Obstet. Gynaecol.* 105:1211-1213.
Kubinyi "3D QSAR in Drug Design: Ligand-Protein Interactions and Molecular Similarity" (1998) *Springer,* 800 pages. p. 2-3:243 (abstract).

(56) References Cited

OTHER PUBLICATIONS

Levin et al. "Direct measurement of the anticholinergic activity of a series of pharmacological compounds on the canine and rabbit urinary bladder" (1982) *J. Urology* 128(2):396-398 (abstract).
Lewy Body Dementia Association, Inc., treatment options page, http://www.lbda.org/content/treatment-options, at least as early as Apr. 10, 2015.
Liang et al. "Olanzapine in the treatment of schizophrenia: a open trial clinical study" (1999) *Chinese Journal of Psychiatry* vol. 04, Title page/TOC only.
Lieben et al. "The Selective 5-HT6 Receptor Antagonist Ro4368554 Restores Memory Performance in Cholinergic and Serotonergic Models of Memory Deficiency in the Rat" (2005) *Neuropsychopharmacology* 30: 2169-2179.
Liem-Moolenaar et al. "Central Nervous System Effects of the Interaction Between Risperidone (single dose) and the 5-HT6 Antagonist SB742457 (repeated doses) in Healthy Men" (2010) *Br. J. Clin. Pharma.* 71(6):907-916.
Lightowler et al. "Anxiolytic-like Effect of Paroxetine in a Rat Social Interaction Test" Oct. 1994) *Pharmacol. Biochem. Behav.* 49(2):281-285 (abstract).
Lindner et al. "An Assessment of the Effects of Serontonin 6 (5-HT6) Receptor Antagonists in Rodent Models of Learning" (2003) *J. Pharmacol. Exp. Ther.* 307(2): 682-691.
Lombardo et al "CTAD Poster Presentation Figure 4 entitled Phase 1 PET Study to Evaluate the Receptor Occupancy of RVT-101" Sep. 21, 2011.
London Stock Exchange Announcement—GlaxoSmithKline (GSK) plc, Issued on Thursday, Dec. 13, 2007, New York, New York.
Lopez et al. "Predictors of progression in patients with AD and Lewy bodies" (2000) *Neurology* 54:1774-1779 (abstract).
Lu et al. "Chronic Exposure to Anticholinergic Medications Adversely Affects the Course of Alzheimer Disease" (Jul.-Aug. 2003) *Am J Geriatr Psychiatry* 11(4):458-461 (abstract).
Maher-Edwards et al "Double-blind, controlled phase II study of a 5-HT6 receptor antagonist, SB-742457, in Alzheimer's disease" (2010) *Current Alzheimer Research* 7:374-385.
Maher-Edwards et al. "SB-742457 and donepezil in Alzheimer disease: a randomized, placebo-controlled study" (2011) *Int. J Geriatr. Psychiatry* 26:536-544.
Major et al. "Establishment of a Line of Human Fetal Glial Cells That Supports JC Virus Multiplication" (1985) *PNAS USA* 82:1257-1261.
Martarello et al. "Radiolabelling and in vivo evaluation of [11C]GSK215083 as a potential PET radioligand for the 5-HT6 receptor in the porcine brain" (2005) *J. Label Compd. Radiopharm.* 48:S7.
Martarello et al.. "Radiolabelling and in vivo evaluation of [11C]GSK215083 as potential PET radioligand for the 5-HT6 receptor in the porcine brain" (2005) *Journal of Cerebral Blood Flow & Metabolism* 25:S598.
McKeith et al. "Efficacy of rivastigmine in dementia with Lewy bodies: a randomised, double-blind, placebo-controlled international study" (2000) *The Lancet* 356:2031-2036 (abstract).
MedlinePlus, MedlinePlus Medical Encyclopedia, 2009, pp. 1-5 (abstract).
Mestre et al. "5-Hydroxytryptamine 2A receptor antagonists as potential treatment for psychiatric disorders" (2013) *Expert Opin. Investig Drugs* 22(4):411-421.
Mitchell et al. "5-HT6 receptors: a novel target for cognitive enhancement" (2005) *Pharmacol & Therapeutics* 108:320-333.
Montgomery et al. "A New Depression Scale Designed to be Sensitive to Change" (Apr. 1979) *Br. J. Psychiatry* 134(4):382-389.
Müller, Inorganic Structural Chemistry, Apr. 15, 1993, John Wiley and Sons, 274 pages, pp. 14-15.
Nordberg et al. "Cholinesterase Inhibitors in the Treatment of Alzheimer's Disease" (1998) *Drug Safety* 19(6):465-480.
Office Action for U.S. Appl. No. 11/883,043, mailed on Sep. 8, 2009.

Oken "Antihistamines, a Possible Risk Factor for Alzheimer's Disease" (1995) *Medical Hypotheses* 44:47-48 (abstract).
Olichney et al. "Cognitive Decline is Faster in Lewy Body Variant than in Alzheimer's Disease" (1998) *Neurology* 51:351-357 (abstract).
Ono Pharmaceutical Co., Ltd. "Launch of Rivistach.RTM. Patch, for the Treatment of Dementia of Alzheimer's Type" (2011) 2 pages.
Parker et al. "Human Kinetic Modeling of the 5HT6 PET Radioligand 11C-GSK215083 and Its Utility for Determining Occupancy at Both 5HT6 and 5HT2A Receptors by SB742457 as a Potential Therapeutic Mechanism of Aaction in Alzheimer Disease" (2015) *J. Nucl. Med.* 56:1901-1909.
Phase 1 Study, result summary. Study AZ3105822, a single-blind, randomized, placebo-controlled study to evaluate the effect of repeated dosing of an investigational product on the pharmacokinetics and pharmacodynamics of Warfarin in healthy adult subjects. http://www.gsk-clinicalstudyregister.com/result _detail.jsp?protocolId=105822&studyId=BC2066FF-1606-487D-B093-189458F0AE76&compound=SB742457 (undated).
Phase 2, Study 1, result summary. Study AZ3110865, a study comparing SB-74257 or donepezil versus placebo in subjects with mild-to-moderate Alzheimer's disease. http:..www.gsk-clinical studyregister.com/result_detail. jsp?protocolId=AZ3110865&studyId=242C4974-9729-4D30-8F91-327CF0631014&compound=SB742457 (undated).
Phase 2, Study 2, result summary. Study AZ3110866, a fixed dose study of SB-742457 versus placebo when added to existing donepezil treatment in subjects with mild-to-moderate Alzheimer's disease. http://www.gsk-clinicalstudyresgister.com/result_detail.jsp?protocolID=AZ3110866&studyId=B8176D5B-C331-4621-9303-2BBF51E4690B&compound=SB742457 (undated).
Pineiro-Nunez et al., "Discovery and SAR studies of 2,6-difluorobenzenesulfonic acid 1-methyl-3-(methylopiperidin-4-yl)-1H-indol-5-yl ester, a novel and potent 5-HT6 antagonist treatment of cognitive deficit", 299th ACS Natl. Mtg., Mar. 13-17, San Diego, Abst. Medi 282 (2005).
Porsolt et al. "Behavioral despair in mice: a primary screening test for antidepressants" (1977) *Arch. Int. Pharmac. Ther.* 229(2):327-336 abstract.
Product Information Sheet, Detrol.RTM. LA (tolterodine tartrate) capsules, Rev. Mar. 2008.
Product Information Sheet, Enablex.RTM. (darifenacin) tablets, T2010-XX.
Product Information Sheet, Exelon.RTM. Patch (rivastigmine transdermal system), LTS Lohmann Therapie Systems AG, 2000.
Product Information Sheet, Sanctura.RTM. (trospium chloride), Rev. Jan. 2011.
Product Information Sheet, VESIcare.RTM. (solifenacin succinate) tablets, Rev. Apr. 2010.
Przyklenk et al. "Targeted inhibition of the serotonin 5HT2A receptor improves coronary patency in an in vivo model of recurrent thrombosis" (2010) *J. Thromb Haemost.* 8(2):331-340.
Raschetti et al. "Cholinesterase Inhibitors in Mild Cognitive Impairment: A Systematic Review of Randomised Trials" (2007) *PloS Med.* 4(11):1818-1828.
Ray et al. "Central Anticholinergic Hypersensitivity in Aging" (Apr.-Jun. 1992) *Journal of Geriatric Psychiatry and Neurology* 5:72-77 (abstract).
Remington's Pharmaceutical Science, 15th ed, Mack Publishing Company, Easton, PA (Jun. 1976) (abstract).
Riemer et al. "Influence of the 5-HT6 Receptor on Acetylcholine Release in the Cortex: Pharmacological Characterization of 4-(2-Bromo-6-pyrrolidin-1-ylpyridine-4-sulfonyl)phenylamine, a Potent and Selective 5-HT6 Receptor Antagonist" (2003) *Brief Articles, J. Med. Chem.* 46:1273-1276.
Roberts et al. "The distribution of 5-HT6 receptors in rat brain: an autoradiographic binding study using the radiolabeled 5-HT6 receptor antagonist '125ISB-258585" (2002) *Brain Research* 934:49-57.
Robichaud et al. "Ch. 2: Recent Advances in Selective Serotonin Receptor Modulation" (2000) *Annual Reports in Medicinal Chemistry* 36:11-20.
Robinul RTM. glycopyrrolate tablets Product Information Sheet, Rev. Apr. 2010.

(56) References Cited

OTHER PUBLICATIONS

Roche Bioreversible Carriers in Drug Design ed (1987) (TOC only).
Roe et al. "Use of Anticholinergic Medications by Older Adults with Dementia" (2002) *JAGS* 50:836-842 (abstract).
Rogers et al. "5-HT6 Receptor Antagonists Enhance Retention of a Water Maze Task in the Rat" (2001) *Psychopharmacology* 158:114-119.
Rojas-Fernandez "Successful Use of Donepezil for the Treatment of Dementia with Lewy Bodies" (2001) *Annals of Pharmacotherapy* 35(2):202-205.
Roth et al. "Serotonin receptors represent highly favorable molecular targets for cognitive enhancement in schizophrenia and other disorders" (2004) *Psychopharmacology* 174:17-24.
Rudolph et al. "The Anticholinergic Risk Scale and Anticholinergic Adverse Effects in Older Persons" (Mar. 10, 2008) *Arch Intern Med* 168(5):508-513.
Russell et al. "N-Arylsulfonylindole Dervivatives as Serotonin 5-HT6 Receptor Ligands" (2001) *J. Med. Chem.* 44(23):3881-3895.
Shua-Haim et al. "Safety, Tolerability, and Caregiver's Impressions of Combination Therapy With Rivastigmine and Memantine for the Treatment of Alzheimer's Disease" (2004) *Neurobiology & Aging* S205: P1-377.
Sink et al. "Dual Use of Bladder Anticholinergics and Cholinesterase Inhibitors: Long-Term Functional and Cognitive Outcomes" (2008) *JAGS* 56:847-853.
Sleight et al. "Characterization of Ro 04-6790 and Ro 63-0563: potent and selective antagonists at human and rat 5-HT6 receptors" (1998) *British Journal of Phamacol.* 124:556-562.
Speer et al. "Influence of Digestive Enzymes Combined with Sodium Lauryl Sulfate on Dissolution of Cross-linked Gelatin Capsules" 2005 AAPS, poster.
Stadler et al. "5-HT6 antagonists: a novel approach for the symptomatic treatment of Alzheimer's Disease", 37th IUPAC Cong. Aug. 14-19, 1999, Berlin, Abst. MM-7.
Strah-Pleynet et al. "5HT2A Receptor Inverse Agonists: Design and SAR of Novel Pyrazole Derivatives" (2006) meeting abstract.
Strah-Pleynet et al. "Bioisosteric Modifications of Urea Derivatives as 5HT2A Inverse-Agonists" 2004 ACS, meeting abstract.
Strah-Pleynet et al. "Discovery and SAR of novel 5-HT.sub.2A, inverse-agonists" 227th ACS National Meeting, MED1 270, Arena Pharmaceutical Inc. (Mar. 2004), 1 page, poster.
Teegarden et al. "Discovery of 1-[3-(4-Bromo-2-methyl-2H-pyrazol-3-yl)-4-methoxy-phenyl]-3-(2,4-difluoro-phenyl)-urea (APD125) and Related 5-HT.sub.2A Inverse Agonists for the Treatment of Insomnia" (2009) *JMC* pp. 1-50.
Teramura-Gronblad et al. "Use of Anticholinergic Drugs and Cholinesterase Inhibitors and Their Association with Psychological Well-Being Among Frail Older Adults in Residential Care Facilities" (2011) *Ann Pharmacotherapy* 45:596-602 (abstract).
Terry et al. "The Cholinergic Hypothesis of Age and Alzheimer's Disease-Related Cognitive Deficits: Recent Challenges and Their Implications for Novel Drug Development" (2003) *JPET* 306(3):821-827.
Thome et al. "Association analysis of HTR6 and HTR2A polymorphisms in sporadic Alzheimer's disease" (2001) *Journal of Neural Transmission* 108:1175-1180.
Totterdell "Synaptic Circutry of Interactions Between Limbic and Dopaminergic Afferents to the Ventral Striatum" (2004) *International Journal of Neuropsychopharmacology* 7:S14 SP.11.01.
Tsai et al. "Association Analysis of the 5-HT6 Receptor Polymorphism C267T in Alzheimer' s Disease" (1999) *Neuroscience Letters* 276:138-139.
Tsao et al. "Transient Memory Impairment and Hallucinations Associated with Tolterodine Use" (Dec. 4, 2003) *New England Journal of Medicine* 349(23):2274-2275 (abstract).
Upton et al. "5-$HT_6$ Receptor antagonists as novel cognitive enhancing agents for Alzheimer's Disease" (2008) *Neurotherapeutics* 5(3):458-469.
Vacante et al. "Extension of JC Virus Host Range to Monkey Cells by Insertion of a Simian Virus 40 Enhancer into the JC Virus Regulatory Region" *Virology* 170:353-361.
Van Eijk et al. "Effect of rivastigmine as an adjunct to usual care with haloperidol on duration of delirium and mortality in critically ill patients: a multicentre, double-blind, placebo-controlled randomised trial" (2010) *The Lancet* 376:1829-1837 (abstract).
Vanover et al. "Role of 5-HT2A receptor antagonists in the treatment of insomnia" (2010) *Nature and Science of Sleep* 2:139-150.
Vasilevskii "Oxidative Iodination of Substituted N-Methylpyrazoles," (1980) *Bull. Acad. Sci. USSR* 29(5):778-784.
Vasilevsky et al. "Study of the Heterocyclization of vic-Substituted Hydrazides of Actylenylpyrazolecarboxylic Acids into N-Amino Pyrazolpyridinones" (2002) *J. Hetercycl. Chem.* 39:1229-1233.
Verdejo et al. "Tratamiento con propantelina de la incontinencia urinaria por inestabilidad vesical en pacientes ancianos" (1992) *Anales de Medicina* 9(3):1160120.
Williams et al. "Survival and mortality differences between dementia with Lewy bodies vs Alzheimer disease" (1935) *Neurology* 67:1935-1941 (abstract).
Willner "Animal Models as Simulations of Depression" (1991) *Trends Pharmacol. Sci.* 12(4):131-136 (abstract).
Woolley et al. "5-HT6 Receptors" (2004) *Current Drug Targets—CNS & Neurological Disorders* 3:59-79.
Woolley et al. "A role for 5-HT6 Receptors in Retention of Spatial Learning in the Morris Water Maze" (2001) *Neuropharmacology* 41:210-219.
Woolley et al. "Reversal of a cholinergic-induced deficit in a rodent model of recognition memory by the selective 5-HT6 receptor antagonist, Ro 04-6790" (2003) *Psychopharmacology* 170:358-367.
Gillman, The serotonin syndrome and its treatment, *Journal of Phychopharmacology* (1999), 31(1): 100-109.
Kalueff et al., Hypolocomotion, anxiety and serotonin syndrome-like behavior contribute to the complex phenotype of serotonin transporter knockout mice, *Genes, Brain and Behavior* (2007), 6:389-400.
International Search Report and Written Opinion for PCT/US16/42556 dated Dec. 23, 2016.
Monti "Serotonin 5-HT2A Receptor Antagonists in the Treatment of Insomnia: Present Status and Future Prospects" (2010) *Drugs of Today* 46(3):183-193.

\* cited by examiner

Differential Scanning Calorimetry (DSC) Thermogram for Form I of
1-[3-(4-Bromo-2-methyl-2H-pyrazol-3-yl)-4-methoxy-phenyl]-3-(2,4-difluoro-phenyl)-urea A Pictorial Representation of the Hemi-acetonitrile Solvate of 1-[3-(4-Bromo-2-methyl-2H-pyrazol-3-yl)-4-methoxy-phenyl]-3-(2,4-difluoro-phenyl)-urea as Generated by Mercury v. 1.4.2 (Build 2) Based on Single-crystal X-ray Diffraction Analysis Comparison of Calculated PXRD Pattern of Form IV, Based Upon Single-crystal X-ray Diffraction Results Obtained at ca. 150 °K Versus Bulk Form IV Isolated from Acetonitrile and Analyzed at ca. 298 °K

PROCESSES USEFUL FOR THE PREPARATION OF 1-[3-(4-BROMO-2-METHYL-2H-PYRAZOL-3-YL)-4-METHOXY-PHENYL]-3-(2,4-DIFLUORO-PHENYL)-UREA AND CRYSTALLINE FORMS RELATED THERETO

CROSS-REFERENCE TO RELATED APPLICATIONS

This application is a continuation of U.S. patent application Ser. No. 14/679,421, filed Apr. 6, 2015, which is a continuation of U.S. patent application Ser. No. 13/126,563, filed Apr. 28, 2011, now U.S. Pat. No. 9,126,946, issued on Sep. 8, 2015, which is a continuation of PCT International Application No. PCT/US2009/005809, filed Oct. 27, 2009, which in turn claims priority to U.S. Provisional Application Ser. No. 61/197,499, filed Oct. 28, 2008, the disclosures of each of which are incorporated herein by reference in their entirety.

FIELD OF THE INVENTION

The present invention is directed to processes and intermediates useful for the preparation of 1-[3-(4-bromo-2-methyl-2H-pyrazol-3-yl)-4-methoxy-phenyl]-3-(2,4-difluoro-phenyl)-urea (Compound I), crystalline forms and solvate forms thereof; and compositions comprising 1-[3-(4-bromo-2-methyl-2H-pyrazol-3-yl)-4-methoxy-phenyl]-3-(2,4-difluoro-phenyl)-urea, crystalline forms and solvate forms thereof prepared by processes as described herein.

BACKGROUND OF THE INVENTION

The compound, 1-[3-(4-bromo-2-methyl-2H-pyrazol-3-yl)-4-methoxy-phenyl]-3-(2,4-difluoro-phenyl)-urea (Compound I, shown below), which is described in PCT Application PCT/US2004/023488 and incorporated herein by reference in its entirety, belongs to a class of serotonin 5-HT$_{2A}$-receptor modulators that are useful in the treatment of serotonin 5-HT$_{2A}$-receptor associated diseases and disorders.

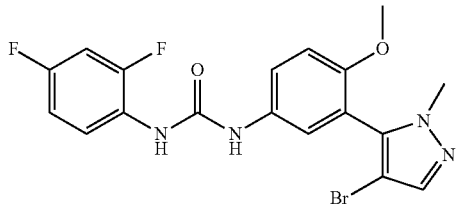 [SMILES: COc1ccc(NC(=O)Nc2ccc(F)cc2F)cc1-c1c(Br)cnn1C]

1-[3-(4-bromo-2-methyl-2H-pyrazol-3-yl)-4-methoxy-phenyl]-3-(2,4-difluoro-phenyl)-urea
(Compound I)

Certain synthetic processes for preparing 1-[3-(4-bromo-2-methyl-2H-pyrazol-3-yl)-4-methoxy-phenyl]-3-(2,4-difluoro-phenyl)-urea have been described in PCT Applications PCT/US2004/023880 and PCT/US2006/002721, both of which are incorporated herein by reference in their entirety.

PCT Application PCT/US2004/023880 discloses processes that prepare 1-[3-(4-bromo-2-methyl-2H-pyrazol-3-yl)-4-methoxy-phenyl]-3-(2,4-difluoro-phenyl)-urea from 3-(4-bromo-2-methyl-2H-methyl-3-yl)-4-methoxy-phenylamine and 2,4-difluorophenyl-isocyanate in the presence of toluene (Example 5, PCT Application PCT/US2004/023880) with an impurity of 0.9 mole % identified as the desbromo of 1-[3-(4-bromo-2-methyl-2H-pyrazol-3-yl)-4-methoxy-phenyl]-3-(2,4-difluoro-phenyl)-urea and an overall purity of 98.2% purity by HPLC. While the solid state properties for 1-[3-(4-bromo-2-methyl-2H-pyrazol-3-yl)-4-methoxy-phenyl]-3-(2,4-difluoro-phenyl)-urea were not characterized, it was found in a subsequent experiment that the toluene process as described in Example 5 (PCT Application PCT/US2004/023880) was observed to be a mixture of at least Form I and Form II.

PCT Application PCT/US2006/002721 discloses processes that prepare 1-[3-(4-bromo-2-methyl-2H-pyrazol-3-yl)-4-methoxy-phenyl]-3-(2,4-difluoro-phenyl)-urea from 3-(4-bromo-2-methyl-2H-methyl-3-yl)-4-methoxy-phenylamine and 2,4-difluorophenyl-isocyanate in the presence of an alcoholic solvent, such as methanol and n-propanol (Examples 1-5, PCT Application PCT/US2006/002721) to give substantially Form II.

Although Form II is considered the more thermodynamically stable polymorph, Form I was identified as the desirable crystalline form based on, inter alia, improved pharmacokinetic characteristics. Accordingly, there exists a need for efficient synthetic procedures for preparing Form I of 1-[3-(4-bromo-2-methyl-2H-pyrazol-3-yl)-4-methoxy-phenyl]-3-(2,4-difluoro-phenyl)-urea that are economically effective, provide batch-to-batch consistency, as well as the preparation of Form I that is substantially pure and/or free of harmful contaminants in bulk quantity. The synthetic procedures and intermediates for 1-[3-(4-bromo-2-methyl-2H-pyrazol-3-yl)-4-methoxy-phenyl]-3-(2,4-difluoro-phenyl)-urea (Compound I), as described herein, meet one or more of these and other needs.

SUMMARY OF THE INVENTION

The present invention provides, inter alia, processes and intermediates for preparing 1-[3-(4-bromo-2-methyl-2H-pyrazol-3-yl)-4-methoxy-phenyl]-3-(2,4-difluoro-phenyl)-urea (Compound I), crystalline forms and solvate forms thereof.

One aspect of the present invention relates to processes for preparing Form I of 1-[3-(4-bromo-2-methyl-2H-pyrazol-3-yl)-4-methoxy-phenyl]-3-(2,4-difluoro-phenyl)-urea comprising the step of:

converting an acetonitrile solvate of 1-[3-(4-bromo-2-methyl-2H-pyrazol-3-yl)-4-methoxy-phenyl]-3-(2,4-difluoro-phenyl)-urea to provide Form I of 1-[3-(4-bromo-2-methyl-2H-pyrazol-3-yl)-4-methoxy-phenyl]-3-(2,4-difluoro-phenyl)-urea.

One aspect of the present invention relates to processes for preparing an acetonitrile solvate of 1-[3-(4-bromo-2-methyl-2H-pyrazol-3-yl)-4-methoxy-phenyl]-3-(2,4-difluoro-phenyl)-urea comprising the steps of:

a) reacting 3-(4-bromo-2-methyl-2H-pyrazol-3-yl)-4-methoxy-phenylamine with 2,4-difluorophenyl-isocyanate in the presence of acetonitrile to form a reaction mixture comprising 1-[3-(4-bromo-2-methyl-2H-pyrazol-3-yl)-4-methoxy-phenyl]-3-(2,4-difluoro-phenyl)-urea; and b) crystallizing 1-[3-(4-bromo-2-methyl-2H-pyrazol-3-yl)-4-methoxy-phenyl]-3-(2,4-difluoro-phenyl)-urea from the reaction mixture to form the acetonitrile solvate of 1-[3-(4-bromo-2-methyl-2H-pyrazol-3-yl)-4-methoxy-phenyl]-3-(2,4-difluoro-phenyl)-urea.

One aspect of the present invention relates to processes for preparing 3-(4-bromo-2-methyl-2H-pyrazol-3-yl)-4-methoxy-phenylamine, the process comprising:

reacting N-[3-(4-bromo-2-methyl-2H-pyrazol-3-yl)-4-methoxy-phenyl]-acetamide with an inorganic base in the presence of a mixture of an aromatic solvent and a $C_1$-$C_6$ alkanol to form 3-(4-bromo-2-methyl-2H-pyrazol-3-yl)-4-methoxy-phenylamine.

One aspect of the present invention relates to processes for preparing 1-[3-(4-bromo-2-methyl-2H-pyrazol-3-yl)-4-methoxy-phenyl]-3-(2,4-difluoro-phenyl)-urea comprising the steps of:

a) reacting N-[4-methoxy-3-(2-methyl-2H-pyrazol-3-yl)-phenyl]-acetamide with a brominating agent in the presence of a brominating solvent to form N-[3-(4-bromo-2-methyl-2H-pyrazol-3-yl)-4-methoxy-phenyl]-acetamide;

b) reacting N-[3-(4-bromo-2-methyl-2H-pyrazol-3-yl)-4-methoxy-phenyl]-acetamide with an inorganic base in the presence of a mixture of an aromatic solvent and a $C_1$-$C_6$ alkanol to form 3-(4-bromo-2-methyl-2H-pyrazol-3-yl)-4-methoxy-phenylamine; and c) reacting 3-(4-bromo-2-methyl-2H-pyrazol-3-yl)-4-methoxy-phenylamine with 2,4-difluorophenyl-isocyanate in the presence of a urea-forming solvent to form 1-[3-(4-bromo-2-methyl-2H-pyrazol-3-yl)-4-methoxy-phenyl]-3-(2,4-difluoro-phenyl)-urea.

One aspect of the present invention relates to processes for preparing Form I of 1-[3-(4-bromo-2-methyl-2H-pyrazol-3-yl)-4-methoxy-phenyl]-3-(2,4-difluoro-phenyl)-urea, the process comprising:

a) dissolving 1-[3-(4-bromo-2-methyl-2H-pyrazol-3-yl)-4-methoxy-phenyl]-3-(2,4-difluoro-phenyl)-urea in tetrahydrofuran to form a solution;

b) adding an aliphatic solvent to the solution to form a mixture comprising a first solvate of 1-[3-(4-bromo-2-methyl-2H-pyrazol-3-yl)-4-methoxy-phenyl]-3-(2,4-difluoro-phenyl)-urea;

c) isolating the first solvate of 1-[3-(4-bromo-2-methyl-2H-pyrazol-3-yl)-4-methoxy-phenyl]-3-(2,4-difluoro-phenyl)-urea from the mixture to provide an isolated first solvate of 1-[3-(4-bromo-2-methyl-2H-pyrazol-3-yl)-4-methoxy-phenyl]-3-(2,4-difluoro-phenyl)-urea;

d) washing the isolated first solvate of 1-[3-(4-bromo-2-methyl-2H-pyrazol-3-yl)-4-methoxy-phenyl]-3-(2,4-difluoro-phenyl)-urea with acetonitrile to form a second solvate of 1-[3-(4-bromo-2-methyl-2H-pyrazol-3-yl)-4-methoxy-phenyl]-3-(2,4-difluoro-phenyl)-urea; and e) converting the second solvate to provide Form I of 1-[3-(4-bromo-2-methyl-2H-pyrazol-3-yl)-4-methoxy-phenyl]-3-(2,4-difluoro-phenyl)-urea.

One aspect of the present invention relates to compositions comprising Form I of 1-[3-(4-bromo-2-methyl-2H-pyrazol-3-yl)-4-methoxy-phenyl]-3-(2,4-difluoro-phenyl)-urea prepared according to any of the processes described herein, wherein the composition comprises less than 0.9 mole % of 1-(2,4-difluorophenyl)-3-(4-methoxy-3-(1-methyl-1H-pyrazol-5-yl)phenyl)urea.

One aspect of the present invention relates to processes for preparing pharmaceutical compositions comprising admixing:

a composition comprising Form I of 1-[3-(4-bromo-2-methyl-2H-pyrazol-3-yl)-4-methoxy-phenyl]-3-(2,4-difluoro-phenyl)-urea prepared according to any of the processes described herein, wherein said composition comprises less than 0.9 mole % of 1-(2,4-difluorophenyl)-3-(4-methoxy-3-(1-methyl-1H-pyrazol-5-yl)phenyl)urea; and a pharmaceutically acceptable carrier.

One aspect of the present invention relates to an acetonitrile solvate of 1-[3-(4-bromo-2-methyl-2H-pyrazol-3-yl)-4-methoxy-phenyl]-3-(2,4-difluoro-phenyl)-urea. In some embodiments, the acetonitrile solvate has a molecular ratio of acetonitrile to 1-[3-(4-bromo-2-methyl-2H-pyrazol-3-yl)-4-methoxy-phenyl]-3-(2,4-difluoro-phenyl)-urea of about 1:2.

One aspect of the present invention relates to an acetonitrile solvate of 1-[3-(4-bromo-2-methyl-2H-pyrazol-3-yl)-4-methoxy-phenyl]-3-(2,4-difluoro-phenyl)-urea. In some embodiments, the acetonitrile solvate has a molecular ratio of acetonitrile to 1-[3-(4-bromo-2-methyl-2H-pyrazol-3-yl)-4-methoxy-phenyl]-3-(2,4-difluoro-phenyl)-urea of about 1:2.

One aspect of the present invention relates to compositions comprising an acetonitrile solvate of 1-[3-(4-bromo-2-methyl-2H-pyrazol-3-yl)-4-methoxy-phenyl]-3-(2,4-difluoro-phenyl)-urea prepared according to any of the processes described herein.

DETAILED DESCRIPTION OF THE INVENTION

Figure 1:
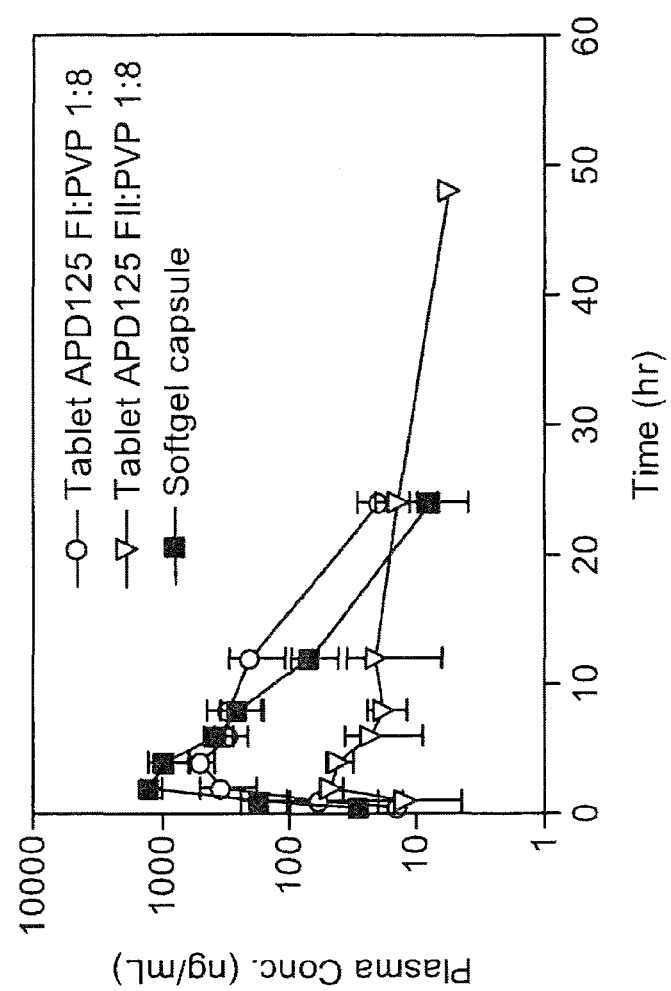
FIG. 1 depicts APD125 plasma exposure in monkeys after oral administration of wet-granulation tablets (composition: 30 mg APD125 Form I or Form II in a ratio of 1:8 to PVP) or SGCs (composition: 40 mg APD125 in Cremophor®:Labrasol® [1:1], Dose Adjusted to 30 mg).

1-[3-(4-bromo-2-methyl-2H-pyrazol-3-yl)-4-methoxy-phenyl]-3-(2,4-difluoro-phenyl)-urea (Compound I) is a potent inverse agonist of the serotonin 5-HT$_{2A}$-receptor and as such is useful for the treatment of serotonin 5-HT$_{2A}$-receptor associated diseases and disorders, for example, increasing slow wave sleep, improving sleep consolidation, improving sleep maintenance and improving sleep quality, and for treating insomnia and related sleep disorders, dyssomnias, parasomnias and nonrestorative sleep and the like; and treating platelet aggregation, coronary artery disease, myocardial infarction, transient ischemic attack, angina, stroke, atrial fibrillation, thrombosis, asthma or symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders and progressive multifocal leukoencephalopathy and the like.

DEFINITIONS

The term "$C_5$-$C_{10}$ alkane" as used herein refers to a straight chain or branched chain alkane with 5 to 10 carbon atoms. Examples include hexane, heptane and the like.

The term "$C_1$-$C_6$ alkanol" as used herein refers to a compound of formula $C_1$-$C_6$ alkyl-OH where the alkyl group has 1 to 6 carbon atoms. Examples include methanol, ethanol, n-propanol, isopropanol, n-butanol, t-butanol and the like.

The term "aromatic solvent" as used herein refers to a solvent or an isomeric mixture of solvents that contains one aromatic ring and is optionally substituted with 1, 2 or 3 substituents provided that the solvent is a liquid at ambient temperature. Examples include benzene, toluene, o-xylene, m-xylene, p-xylene, xylenes and the like.

The term "$C_5$-$C_8$ cycloalkane" as used herein refers to a cyclic alkane with 5 to 8 carbon atoms. Examples include cyclohexane, cycloheptane and the like.

The term "inorganic base" as used herein refers to a base selected from an alkali metal hydroxide and alkaline earth hydroxide. Examples include lithium hydroxide, sodium hydroxide, potassium hydroxide and the like.

The term "ICH" as used herein refers to The International Conference on Harmonization of Technical Requirements for Registration of Pharmaceuticals for Human Use (ICH).

The terms "5-HT$_{2A}$ serotonin receptor-related disorder" and "5-HT$_{2A}$ serotonin receptor-related disease" as used herein respectively refer to a disorder or disease in an individual, which may be prevented, inhibited, ameliorated, treated or cured by modulation (e.g. agonsim, antagonism or inverse agonism) of the 5HT$_{2A}$ serotonin receptor, for example, by administering to the individual in need thereof a therapeutically effective amount of a pharmaceutical composition of the present invention comprising a 5HT$_{2A}$ serotonin receptor modulator.

The term "in need of treatment" as used herein refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" as used herein refers to any animal, including mammals, preferably mice, rats, other rodents, rabbits, dogs, cats, swine, cattle, sheep, horses, or primates, and most preferably humans.

The term "inverse agonists" as used herein refers to moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease;

(2) Inhibiting the disease; for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The term "sleep maintenance" as used herein refers to the ability to sleep without persistent interruptions or extended periods of wakefulness. Sleep Maintenance Insomnia is a disturbance in maintaining sleep after sleep onset is achieved. It is characterized by persistently interrupted sleep without difficulty falling asleep, and sleep-continuity disturbance. Parameters used for measuring sleep maintenance include but are not limited to, wake time after sleep onset (WASO) and number of awakenings (NAW).

The term "sleep quality" as used herein refers to both the subjective assessment given by an individual of how restorative and undisturbed sleep has been (via a standardized questionnaire) and to a series of objective measures derived from polysomnography. Examples of standardized sleep questionnaires, include but are not limited to the Pittsburgh Sleep Quality Index (Buysse et al., Psychiatry Research (1989), 28(2), 193-213). Examples of objective measures of sleep quality include, but are not limited to, the amount and depth of nonREM sleep, the amount of REM sleep and the temporal organization of nonREM and REM stages. Subjective and objective measures of sleep quality are not necessarily concordant.

The term "nonrestorative sleep" as used herein refers to a disorder characterized by the subjective assessment given by an individual that sleep is restless, light, or of poor quality even though the duration may appear normal. NRS is associated with other symptoms including, but not limited to, excessive daytime sleepiness, mood swings and cognitive impairments.

The term "coPVP" as used herein refers to a vinylpyrrolidone-vinyl acetate copolymer, CAS registry number 25086-89-9. The term is used interchangeably with the terms copolyvidonum Plasdone™, copovidone and copolyvidone. coPVP has following structural formula:

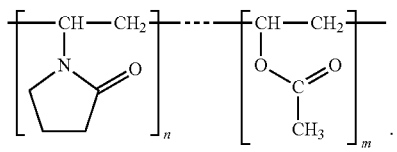

In some embodiments coPVP is a copolymer of 1-vinyl-2-pyrrolidone and vinyl acetate in a ratio of 6:4 by mass, wherein n≈1.2 m. Examples of coPVP include but are not limited to Kollidon™ VA 64, Plasdone™ S-630 and the like.

The term "cps" as used herein is intended to refer to the unit of dynamic viscosity known as the centipoise (cP). 1 cP=1 millipascal second.

The term "DFA" as used herein refers to 2,4-difluoroaniline, CAS registry number 367-25-9, which represented by the following formula:

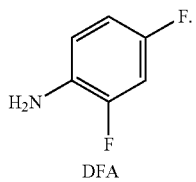

DFA

The term "HDPE" as used herein refers to high-density polyethylene.

The term "MCC" as used herein refers to microcrystalline cellulose, CAS registry number 9004-34-6. The term is used interchangeably with the terms cellulose gel, crystalline cellulose and E460. MCC has the following structural formula:

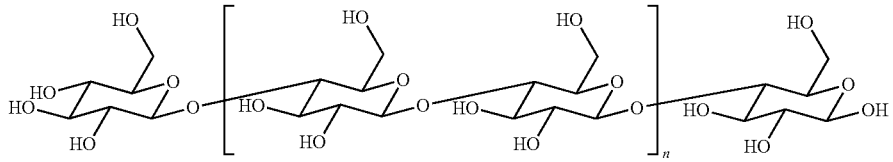

wherein n≈220.
Examples of MCC include, but are not limited to, Avicel™ PH, Avicel™ PH 102, Celex™, Celphere™, Ceolus™ KG, Emcocel™, Ethispheres™, Fibrocel™, Pharmacel™, Tabulose™ and Vivapur™.

The term "PIC" as used herein refers to powder in capsule.

The term "Poloxamer" as used herein refers to a class of pharmaceutical excipients comprising or consisting essentially of either a single compound or a mixture of compounds prepared from synthetic block copolymers of ethylene oxide and propylene oxide. In some embodiments, an excipient in this class comprises or consists essentially of a single compound or a mixture of compounds of the following formula:

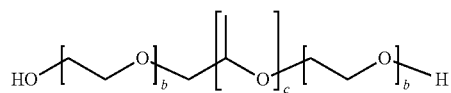

wherein "b" at each occurrence is independently an integer between 1 to 102; "c" is an integer between 1 and 57; b+c+b is 3 to 327; and the average molecule weight of the poloxamer is about 17500 or less. Poloxamers are known or can be prepared by methods in the art. A number of poloxamers are commercially available. Representative examples of a Poloxamer include, but are not limited to, Poloxamer 124 (Pluronic® L44NF), Poloxamer 188 (Pluronic® F68NF), Poloxamer 237 (Pluronic® F87NF), Poloxamer 338 (Pluronic® F108NF), Poloxamer 407 (Pluronic® F127NF) and the like.

The term "PVA" as used herein refers to polyvinyl alcohol, CAS registry number 9002-89-5. The term is used interchangeably with the term vinyl alcohol polymer. PVA has the following structural formula:

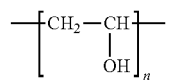

wherein n lies between 500 and 5000, equivalent to a molecular weight range of approximately 20,000 to 200,000. In some embodiments PVA is high viscosity with a molecular weight≈200,000. In some embodiments PVA is medium viscosity with a molecular weight≈130,000. In some embodiments PVA is medium viscosity with a molecular weight≈20,000. Examples of PVA include but are not limited to Airvol™, Elvanol™ and Gohsenol™.

The term "PVP" as used herein refers to polyvinylpyrrolidone. The term is used interchangeably with the terms, E1201, povidone, povidonum, poly[1-(2-oxo-1-pyrrolidinyl)ethylene, polyvidone and 1-vinyl-2-pyrrolidinone polymer. PVP has the following structural formula:

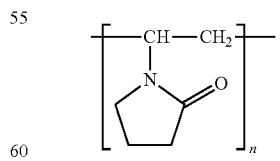

wherein the molecular weight is from about 2500 to about 3,000,000. Examples of PVP include, but are not limited to, Kollidon™, Kollidon™ VA 64, Plasdone™, Plasdone™ K-29/32 and Kollidon™ 30.

The term "% RSD" as used herein refers to the relative standard deviation, which is the absolute value of the coefficient of variation expressed as a percentage. The term is widely used in analytical chemistry to express the precision of an assay:

(standard deviation of array $X$)×100/(average of array $X$)=relative standard deviation.

The term "SGC" as used herein refers to a soft gelatin capsule.

The term "SLS" as used herein refers to sodium lauryl sulfate, which has the following structural formula:

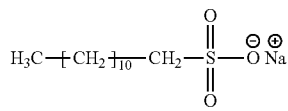

The term "xCMC" as used herein refers to croscarmellose sodium, CAS Registry Number 74811-65-7. The term is used interchangeably with the terms carmellosum natricum conexum, crosslinked carboxymethyl cellulose sodium and modified cellulose gum. xCMC is a crosslinked polymer of carboxymethyl cellulose sodium. Carboxymethyl cellulose sodium has the following structural formula:

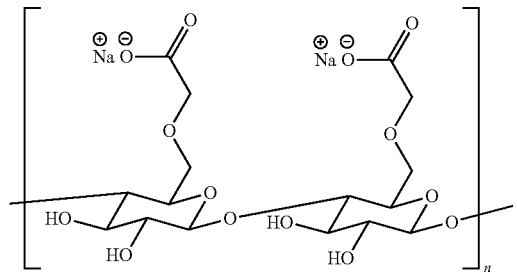

Examples of xCMC include, but are not limited to, Ac-Di-Sol™, Explocel™, Nymcel™ ZSX, Pharmacel™ XL, Primellose™, Solutab™ and Vivasol™.

The term "xPVP" as used herein refers to crosslinked povidone, CAS registry number 9003-39-8, wherein povidone has the same definition as described herein. The term is used interchangeably with the terms crospovidone, crospovidonum, E1202, polyvinylpolypyrrolidone, PVPP, 1-vinyl-2-pyrrolidinone and 1-ethenyl-2-pyrrolidinone homopolymer. Examples of xPVP include, but are not limited to, PolyPlasdone™ XL, PolyPlasdone™ XL-10, Kollidon™ CL and Kollidon™ CL-M.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All combinations of the embodiments pertaining to the aspects described herein are specifically embraced by the present invention just as if each and every combination was individually explicitly recited, to the extent that such combinations embrace possible aspects. In addition, all subcombinations of the embodiments contained within the aspects described herein, as well as all subcombinations of the embodiments contained within all other aspects described herein, are also specifically embraced by the present invention just as if each and every subcombination of all embodiments are explicitly recited herein.

Certain Aspects of the Present Invention

1. Form I of 1-[3-(4-Bromo-2-methyl-2H-pyrazol-3-yl)-4-methoxy-phenyl]-3-(2,4-difluoro-phenyl)-urea (Compound L), Processes and Compositions related thereto One aspect of the present invention is directed to the preparation of Form I of 1-[3-(4-bromo-2-methyl-2H-pyrazol-3-yl)-4-methoxy-phenyl]-3-(2,4-difluoro-phenyl)-urea (Compound I) and compositions thereof. Form I can be identified by its unique solid state signature with respect to, for example, differential scanning calorimetry (DSC), powder X-ray diffraction (PXRD), IR Raman spectroscopy and other solid state methods. Further characterization with respect to water or solvent content of the crystalline form can be gauged by any of the following methods for example, thermogravimetric analysis (TGA), DSC and the like. For DSC, it is known that the temperatures observed for thermal events will depend upon the rate of temperature change as well as sample preparation technique and the particular instrument employed. Thus, the values reported herein relating to DSC thermograms can vary by plus or minus about 4° C. The values reported herein relating to DSC thermograms can also vary by plus or minus about 20 joules per gram. In samples contaminated with Form II of 1-[3-(4-bromo-2-methyl-2H-pyrazol-3-yl)-4-methoxy-phenyl]-3-(2,4-difluoro-phenyl)-urea the values reported herein relating to DSC thermograms can vary by plus or minus >20 joules per gram. For PXRD, the relative intensities of the peaks can vary, depending upon the sample preparation technique, the sample mounting procedure and the particular instrument employed. Moreover, instrument variation and other factors can often affect the 2θ values. Therefore, the peak assignments of diffraction patterns can vary by plus or minus about 0.2°2θ. For TGA, the features reported herein can vary by about ±5° C. The TGA features reported herein can also vary by about ±2% weight change due to, for example, sample variation. Further characterization with respect to hygroscopicity of the crystalline form can be gauged by, for example, dynamic vapor sorption (DVS). The DVS features reported herein can vary by about ±5% relative humidity. The DVS features reported herein can also vary and by about ±5% weight change.

The physical properties of crystalline Form I of 1-[3-(4-bromo-2-methyl-2H-pyrazol-3-yl)-4-methoxy-phenyl]-3-(2,4-difluoro-phenyl)-urea (Compound I) are summarized in Table A below.

TABLE A

Characterization of Form I of 1-[3-(4-bromo-2-methyl-2H-pyrazol-3-yl)-4-methoxy-phenyl]-3-(2,4-difluoro-phenyl)-urea (Compound I)

Figure 21:
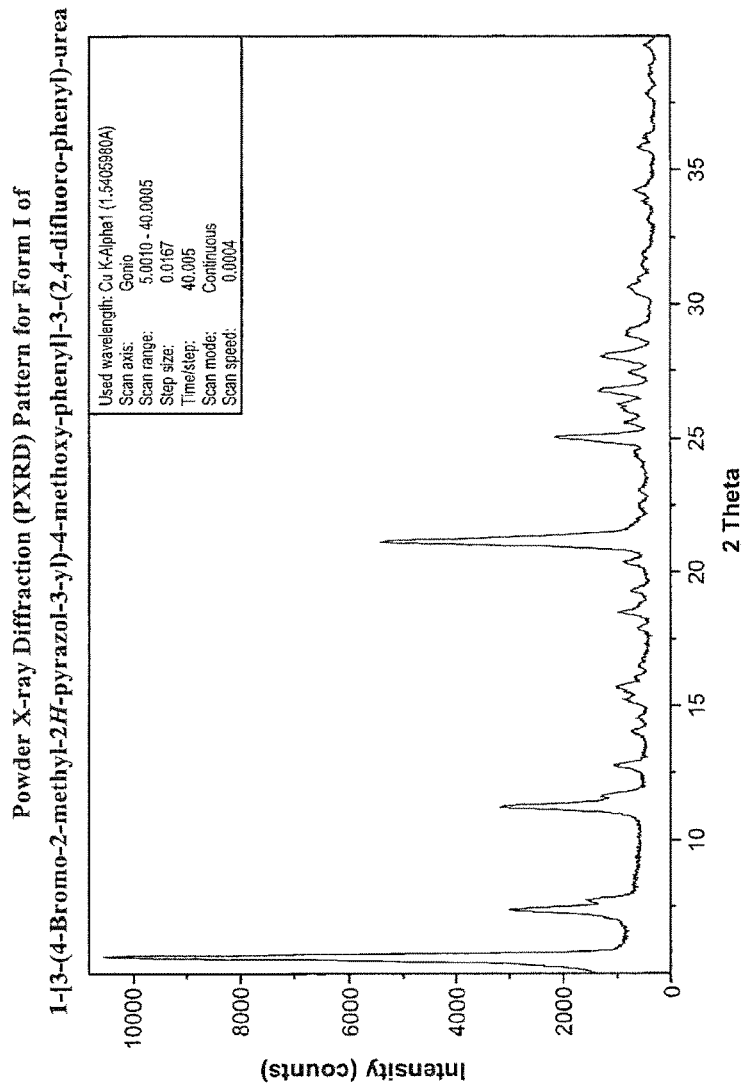
FIG. 21 depicts a powder X-ray diffraction (PXRD) pattern for Form I of 1-[3-(4-bromo-2-methyl-2H-pyrazol-3-yl)-4-methoxy-phenyl]-3-(2,4-difluoro-phenyl)-urea (Compound I), which was recorded using a PANalytical X'Pert Plus Powder X-Ray Diffractometer in the theta/theta geometry; scanning angles 5.0°-40.0°2θ.

| | |
|---|---|
| PXRD | FIG. 21: Peaks of about 17% or greater relative intensity at 5.6°, 7.4°, 11.2°, 21.1° and 25.0° 2θ |
| DSC | FIG. 22: an endotherm with an extrapolated onset temperature of about 170° C., an associated heat flow of about 64 joules per gram and a peak temperature of about 172° C. |
| FT RAMAN | FIG. 23: Peaks at 3086, 2955, 2840, 1656, 1622, 1605, 1572, 1534, 1004, 1004, 964, 911, 759, 751, 732, 723, 673, 505, 390, 335 and 315 cm$^{-1}$ |
| TGA | FIG. 24: negligible weight loss below about 150° C. |

The negligible weight loss observed in the TGA data suggests that Form I of 1-[3-(4-bromo-2-methyl-2H-pyrazol-3-yl)-4-methoxy-phenyl]-3-(2,4-difluoro-phenyl)-urea (Compound I) is an anhydrous, non-solvated crystalline form. The DSC thermogram further reveals a melting endotherm with an onset at about 170° C.

A further aspect of the present invention is directed to compositions comprising Form I of 1-[3-(4-bromo-2-methyl-2H-pyrazol-3-yl)-4-methoxy-phenyl]-3-(2,4-difluoro-phenyl)-urea and less than 0.9 mole % of 1-(2,4-difluorophenyl)-3-(4-methoxy-3-(1-methyl-1H-pyrazol-5-yl)phenyl)urea.

One aspect of the present invention is directed to compositions comprising Form I of 1-[3-(4-bromo-2-methyl-2H-pyrazol-3-yl)-4-methoxy-phenyl]-3-(2,4-difluoro-phenyl)-urea, wherein the compositions comprise less than 0.9 mole % of 1-(2,4-difluorophenyl)-3-(4-methoxy-3-(1-methyl-1H-pyrazol-5-yl)phenyl)urea. In some embodiments, Form I of 1-[3-(4-bromo-2-methyl-2H-pyrazol-3-yl)-4-methoxy-phenyl]-3-(2,4-difluoro-phenyl)-urea constitutes at least about 0.1% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 1% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 5% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 10% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 15% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 20% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 30% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 40% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 50% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 60% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 70% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 80% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 90% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 95% by weight of the composition.

One aspect of the present invention is directed to compositions comprising Form I of 1-[3-(4-bromo-2-methyl-2H-pyrazol-3-yl)-4-methoxy-phenyl]-3-(2,4-difluoro-phenyl)-urea and less than 0.9 mole % of 1-(2,4-difluorophenyl)-3-(4-methoxy-3-(1-methyl-1H-pyrazol-5-yl)phenyl)urea and further comprising a pharmaceutically acceptable carrier. In some embodiments, the composition is formulated for oral administration. In some embodiments, the composition is in the form of a pill, capsule or tablet.

2. Converting an acetonitrile solvate of 1-[3-(4-bromo-2-methyl-2H-pyrazol-3-yl)-4-methoxy-phenyl]-3-(2,4-difluoro-phenyl)-urea to Form I of 1-[3-(4-bromo-2-methyl-2H-pyrazol-3-yl)-4-methoxy-phenyl]-3-(2,4-difluoro-phenyl)-urea (Compound 1)

One aspect of the present invention relates to processes for preparing Form I of 1-[3-(4-bromo-2-methyl-2H-pyrazol-3-yl)-4-methoxy-phenyl]-3-(2,4-difluoro-phenyl)-urea comprising the step of:

converting an acetonitrile solvate of 1-[3-(4-bromo-2-methyl-2H-pyrazol-3-yl)-4-methoxy-phenyl]-3-(2,4-difluoro-phenyl)-urea to provide Form I of 1-[3-(4-bromo-2-methyl-2H-pyrazol-3-yl)-4-methoxy-phenyl]-3-(2,4-difluoro-phenyl)-urea.

In some embodiments, the acetonitrile solvate of 1-[3-(4-bromo-2-methyl-2H-pyrazol-3-yl)-4-methoxy-phenyl]-3-(2,4-difluoro-phenyl)-urea has a molecular ratio of acetonitrile to 1-[3-(4-bromo-2-methyl-2H-pyrazol-3-yl)-4-methoxy-phenyl]-3-(2,4-difluoro-phenyl)-urea of about 1:2 (i.e., hemi-acetonitrile solvate of 1-[3-(4-bromo-2-methyl-2H-pyrazol-3-yl)-4-methoxy-phenyl]-3-(2,4-difluoro-phenyl)-urea).

Figure 25:
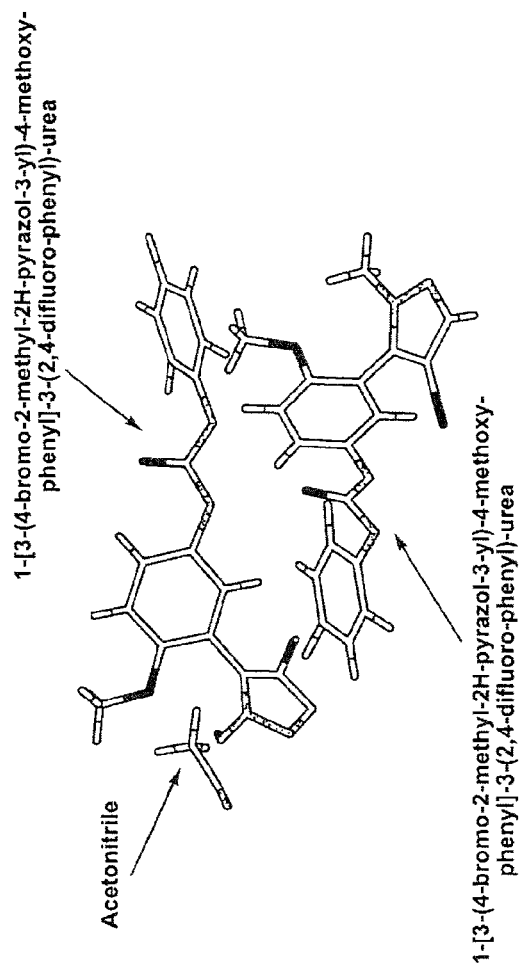
FIG. 25 depicts a pictorial representation of the hemi-acetonitrile solvate of 1-[3-(4-bromo-2-methyl-2H-pyrazol-3-yl)-4-methoxy-phenyl]-3-(2,4-difluoro-phenyl)-urea (Form IV) as generated by Mercury v. 1.4.2 (build 2) based on single-crystal X-ray diffraction analysis.
Figure 26:
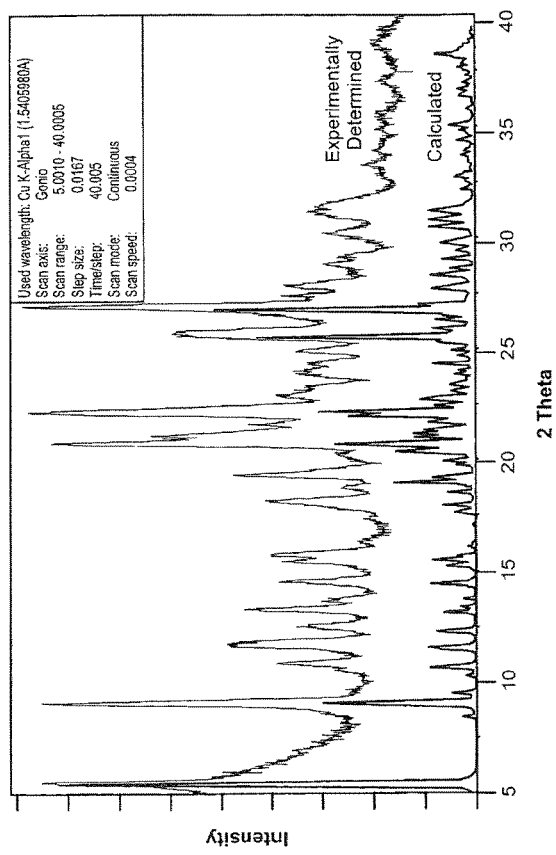
FIG. 26 depicts the comparison of calculated PXRD pattern of hemi-acetonitrile solvate of 1-[3-(4-bromo-2-methyl-2H-pyrazol-3-yl)-4-methoxy-phenyl]-3-(2,4-difluoro-phenyl)-urea (Form IV), based upon single-crystal X-diffraction results obtained at ca. 150° K versus bulk Form IV isolated from acetonitrile and analyzed at ca. 298° K.
Figure 27:
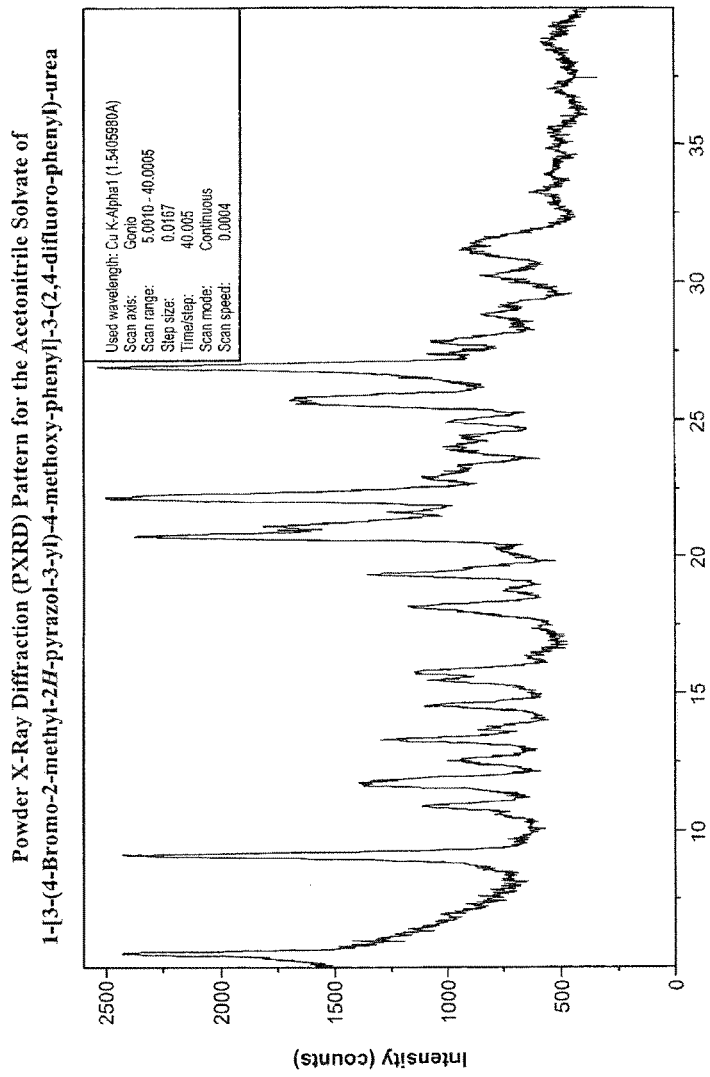
FIG. 27 depicts a powder X-ray diffraction (PXRD) pattern for a Acetonitrile Solvate of 1-[3-(4-Bromo-2-methyl-2H-pyrazol-3-yl)-4-methoxy-phenyl]-3-(2,4-difluoro-phenyl)-urea, which was recorded using a PANalytical X'Pert Plus Powder X-Ray Diffractometer in the 2θ geometry; scanning angles 5.0°-40.0°2θ.

A single-crystal X-ray diffraction analysis demonstrated the acetonitrile solvate to exist as a hemi-acetonitrile solvate containing a theoretical acetonitrile content of 4.75% w/w, having the molecular formula $C_{18}H_{15}BrF_2N_2O_2 \cdot 0.5(CH_3CN)$, referred herein as Form IV and hemi-acetonitrile solvate of 1-[3-(4-bromo-2-methyl-2H-pyrazol-3-yl)-4-methoxy-phenyl]-3-(2,4-difluoro-phenyl)-urea. A pictorial representation of the hemi-acetonitrile solvate as generated by is Mercury v. 1.4.2 (build 2) is shown in FIG. 25. A calculated X-ray powder diffraction pattern of Form IV, derived from the single-crystal results, is provided in FIG. 26, which is overlaid with an experimentally obtained X-ray powder diffraction pattern of bulk acetonitrile solvate Form IV isolated from acetonitrile. FIG. 27 shows the experimentally obtained X-ray powder diffraction pattern without the calculated PXRD.

Figure 28:
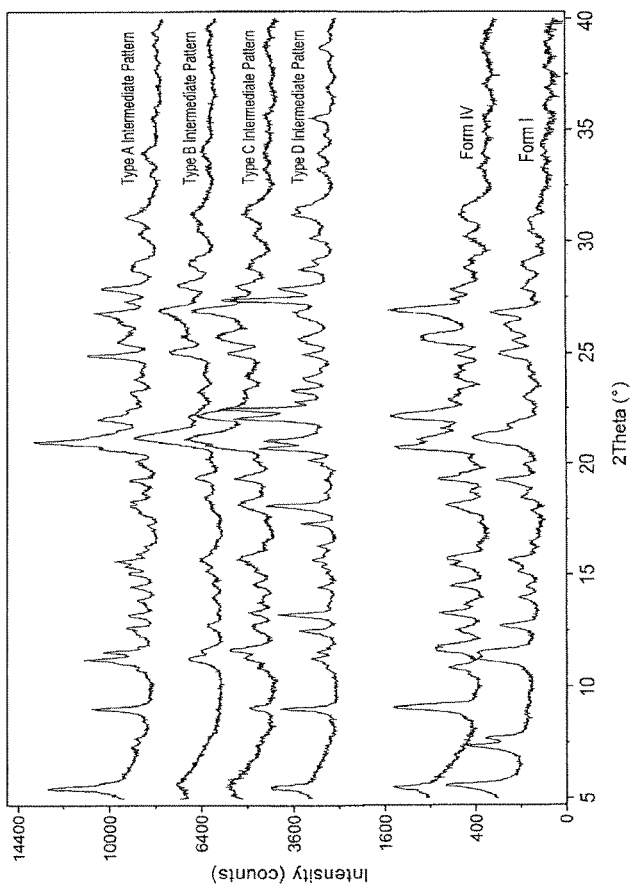
FIG. 28 depicts the transient X-ray powder diffraction patterns observed as Form IV of 1-[3-(4-bromo-2-methyl-2H-pyrazol-3-yl)-4-methoxy-phenyl]-3-(2,4-difluoro-phenyl)-urea converts into Form I, which was recorded using a PANalytical X'Pert Plus Powder X-Ray Diffractometer in the 2θ geometry; scanning angles 5.0°-40.0°2θ.

Upon solvent content reduction, by evaporation and/or heating, Form IV will convert to Form I, exhibiting a range of X-ray powder diffraction patterns (FIG. 28) potentially intermediate in appearance between Forms IV and I and/or having the appearance of binary mixtures of Forms IV and I until the sample in question has fully converted to Form I. Once Form IV is isolated from acetonitrile the conversion from Form IV to Form I can occur within minutes to weeks, depending upon storage or drying conditions. Since the conversion to Form I can potentially occur quite quickly upon isolation from acetonitrile at room temperature, X-ray powder diffraction patterns obtained during the conversion process can be complicated by potential Form IV to Form I conversion during acquisition of a single X-ray powder diffraction pattern. Once conversion of Form IV to Form I is complete, a well-defined and characteristic X-ray powder diffraction pattern of Form I is observed.

The conversion of the acetonitrile solvate of 1-[3-(4-bromo-2-methyl-2H-pyrazol-3-yl)-4-methoxy-phenyl]-3-(2,4-difluoro-phenyl)-urea (for example, Form IV) to Form I of 1-[3-(4-bromo-2-methyl-2H-pyrazol-3-yl)-4-methoxy-phenyl]-3-(2,4-difluoro-phenyl)-urea can be conducted under a variety of reduced pressures and temperatures.

In some embodiments, the converting an acetonitrile solvate of 1-[3-(4-bromo-2-methyl-2H-pyrazol-3-yl)-4-methoxy-phenyl]-3-(2,4-difluoro-phenyl)-urea is conducted under reduced pressure. In some embodiments, the converting an acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 100 mm Hg or less. In some embodiments, the converting an acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 35 mm Hg or less. In some embodiments, the converting an acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 10 mm Hg or less. In some embodiments, the converting an acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 5 mm Hg or less.

If the acetonitrile solvate of 1-[3-(4-bromo-2-methyl-2H-pyrazol-3-yl)-4-methoxy-phenyl]-3-(2,4-difluoro-phenyl)-urea (Form IV) is left in acetonitrile or if during post-isolation from acetonitrile the residual solvent content is too great then there is a risk that Form IV will convert to Form II. Therefore, as the solvent content is decreased the risk of Form IV converting to Form II is reduced. The undesirable conversion of Form IV to Form II was found to be temperature dependent and as a result, by controlling the temperature the conversion of Form IV to Form II could be minimized. Accordingly, the conversion of Form IV to Form I of 1-[3-(4-bromo-2-methyl-2H-pyrazol-3-yl)-4-methoxy-phenyl]-3-(2,4-difluoro-phenyl)-urea can be conducted at a first temperature and then at a second temperature optionally under reduced pressure.

In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted during at least two time periods, wherein the conversion is conducted at a first temperature during a first time period and wherein the conversion is conducted at a second temperature during a second time period, and wherein the first temperature is not equivalent to the second temperature.

In some embodiments, the second temperature is higher than the first temperature.

In some embodiments, the first temperature is at about 0° C. to about 45° C. In some embodiments, the first temperature is at about 15° C. to about 40° C. In some embodiments, the first temperature is at about 20° C. to about 30° C.

In some embodiments, the second temperature is about 45° C. to about 90° C. In some embodiments, the second temperature is about 60° C. to about 80° C. In some embodiments, the second temperature is about 65° C. to about 75° C.

In some embodiments, the first temperature is at about 20° C. to about 30° C. and the second temperature is about 65° C. to about 75° C.

The first temperature can be maintained until the solvent content is sufficiently reduced to minimize the conversion to Form II. Loss on drying (LOD) is one method for determining the solvent content present in the bulk material. This is achieved by obtaining representative samples of the bulk material at various time points and determining the LOD. The LOD for each sample is expressed as the percentage of volatiles lost during the drying of the sample and indicates the percent of the volatiles that remain in the bulk material at the specific time the sample was obtained. Once the suitable LOD level or solvent content is achieved then the second temperature is initiated. A variety of instruments can be used for LOD determinations; one such instrument is a moisture analyzer by Denver Instruments (Model IR-200 or equivalent model).

In some embodiments, the first temperature is maintained until the LOD is about 35%, about 30%, about 25%, about 20%, about 15%, about 10%, about 5% or less for a representative sample of the bulk material obtained from any of the process as described herein before initiating the second temperature, optionally this process can be conducted under reduced pressure.

Loss on drying is a method that can be used to determine the amount of volatiles when conducting large scale processes, other suitable methods can also be used, such as, $^1$H NMR, gas chromatography (such as, head-space GC), thermogravimetric analysis (TGA) and the like.

In some embodiments the process further comprises the step of maintaining the first temperature until a loss on drying (LOD) for a representative sample from the process is at a level of about 30% or less. In some embodiments the process further comprises the step of maintaining the first temperature until a loss on drying (LOD) for a representative sample from the process is at a level of about 20% or less. In some embodiments the process further comprises the step of maintaining the first temperature until a loss on drying (LOD) for a representative sample from the process is at a level of about 15% or less. In some embodiments the process further comprises the step of maintaining the first temperature until a loss on drying (LOD) for a representative sample from the process is at a level of about 10% or less.

In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 0° C. to about 45° C. until a loss on drying (LOD) for a representative sample from the process is at a level of about 30% or less and thereafter raising to a second temperature of about 45° C. to about 90° C. In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 15° C. to about 40° C. until a loss on drying (LOD) for a representative sample from the process is at a level of about 20% or less and thereafter raising to a second temperature about 60° C. to about 80° C. In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 20° C. to about 30° C. until a loss on drying (LOD) for a representative sample from the process is at a level of about 15% or less and thereafter raising to a second temperature of about 60° C. to about 80° C. In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 20° C. to about 30° C. until a loss on drying (LOD) for a representative sample from the process is at a level of about 10% or less and thereafter raising to a second temperature of about 65° C. to about 75° C.

In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 35 mm Hg or less at a first temperature of about 20° C. to about 30° C. until a loss on drying (LOD) for a representative sample from the process is at a level of about 10% or less; and thereafter raising the first temperature to a second temperature of about 65° C. to about 75° C. while maintaining the reduced pressure of about 35 mm Hg or less.

3. Preparation of an acetonitrile solvate of 1-[3-(4-bromo-2-methyl-2H-pyrazol-3-yl)-4-methoxy-phenyl]-3-(2,4-difluoro-phenyl)-urea As described herein, supra, the acetonitrile solvate of 1-[3-(4-bromo-2-methyl-2H-pyrazol-3-yl)-4-methoxy-phenyl]-3-(2,4-difluoro-phenyl)-urea can be used as an intermediate to prepare Form I of 1-[3-(4-bromo-2-methyl-2H-pyrazol-3-yl)-4-methoxy-phenyl]-3-(2,4-difluoro-phenyl)-urea. The present invention also discloses processes for preparing the acetonitrile solvate of 1-[3-(4-bromo-2-methyl-2H-pyrazol-3-yl)-4-methoxy-phenyl]-3-(2,4-difluoro-phenyl)-urea.

Accordingly, one aspect of the present invention relates to processes for preparing an acetonitrile solvate of 1-[3-(4-bromo-2-methyl-2H-pyrazol-3-yl)-4-methoxy-phenyl]-3-(2,4-difluoro-phenyl)-urea comprising the steps of:

a) reacting 3-(4-bromo-2-methyl-2H-pyrazol-3-yl)-4-methoxy-phenylamine with 2,4-difluorophenyl-isocyanate in the presence of acetonitrile to form a reaction mixture comprising 1-[3-(4-bromo-2-methyl-2H-pyrazol-3-yl)-4-methoxy-phenyl]-3-(2,4-difluoro-phenyl)-urea; and b) crystallizing the 1-[3-(4-bromo-2-methyl-2H-pyrazol-3-yl)-4-methoxy-phenyl]-3-(2,4-difluoro-phenyl)-urea from the reaction mixture to form the acetonitrile solvate of 1-[3-(4-bromo-2-methyl-2H-pyrazol-3-yl)-4-methoxy-phenyl]-3-(2,4-difluoro-phenyl)-urea, the general process is illustrated in Scheme 1 below.

Scheme 1

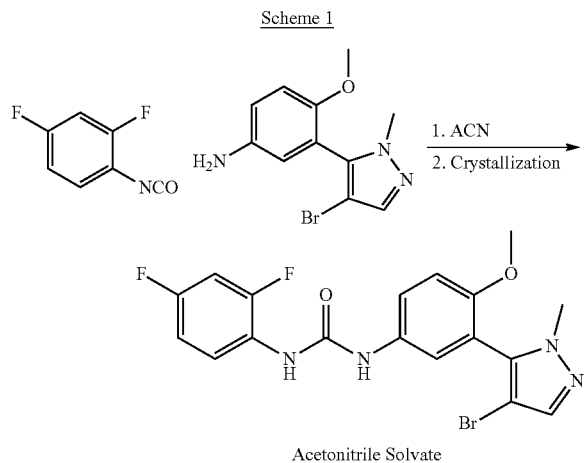

Acetonitrile Solvate

The starting material shown in Scheme 1, 3-(4-bromo-2-methyl-2H-pyrazol-3-yl)-4-methoxy-phenylamine, can be prepared by a variety of suitable methods, for examples, such as those described in PCT Applications PCT/US2004/023880 and PCT/US2006/002721, both of which are incorporated herein by reference in their entirety. In addition to these methods, 3-(4-bromo-2-methyl-2H-pyrazol-3-yl)-4-methoxy-phenylamine can also be prepared by the novel processes described herein that utilize, in general, an inorganic base in the presence of a mixture comprising an aromatic solvent and a $C_1$-$C_6$ alkanol.

In some embodiments, the acetonitrile solvate of 1-[3-(4-bromo-2-methyl-2H-pyrazol-3-yl)-4-methoxy-phenyl]-3-(2,4-difluoro-phenyl)-urea has a molecular ratio of acetonitrile to 1-[3-(4-bromo-2-methyl-2H-pyrazol-3-yl)-4-methoxy-phenyl]-3-(2,4-difluoro-phenyl)-urea of about 1:2.

In some embodiments, reacting 3-(4-bromo-2-methyl-2H-pyrazol-3-yl)-4-methoxy-phenylamine with 2,4-difluorophenyl-isocyanate is conducted under a nitrogen atmosphere.

In some embodiments, reacting 3-(4-bromo-2-methyl-2H-pyrazol-3-yl)-4-methoxy-phenylamine with 2,4-difluorophenyl-isocyanate is conducted in the presence of about 10% of $H_2O$ or less. In some embodiments, reacting 3-(4-bromo-2-methyl-2H-pyrazol-3-yl)-4-methoxy-phenylamine with 2,4-difluorophenyl-isocyanate is conducted in the presence of about 1% of $H_2O$ or less. In some embodiments, reacting 3-(4-bromo-2-methyl-2H-pyrazol-3-yl)-4-methoxy-phenylamine with 2,4-difluorophenyl-isocyanate is conducted in the presence of about 0.1% of $H_2O$ or less.

In some embodiments, reacting 3-(4-bromo-2-methyl-2H-pyrazol-3-yl)-4-methoxy-phenylamine with 2,4-difluorophenyl-isocyanate is conducted at a temperature of about −30° C. to about 10° C. In some embodiments, reacting 3-(4-bromo-2-methyl-2H-pyrazol-3-yl)-4-methoxy-phenylamine with 2,4-difluorophenyl-isocyanate is conducted at a temperature of about −25° C. to about 0° C. In some embodiments, reacting 3-(4-bromo-2-methyl-2H-pyrazol-3-yl)-4-methoxy-phenylamine with 2,4-difluorophenyl-isocyanate is conducted at a temperature of about −15° C. to about −5° C.

In some embodiments, reacting 3-(4-bromo-2-methyl-2H-pyrazol-3-yl)-4-methoxy-phenylamine with 2,4-difluorophenyl-isocyanate is conducted by adding the 2,4-difluorophenyl-isocyanate to the 3-(4-bromo-2-methyl-2H-pyrazol-3-yl)-4-methoxy-phenylamine in acetonitrile to form the reaction mixture.

In some embodiments, the reaction mixture comprises less than about 2% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, the reaction mixture comprises less than about 1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, the reaction mixture comprises less than about 0.1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC.

In some embodiments, adding 2,4-difluorophenyl-isocyanate is conducted at a rate sufficient to form the reaction mixture, wherein the reaction mixture comprises less than about 2% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, adding 2,4-difluorophenyl-isocyanate is conducted at a rate sufficient to form the reaction mixture, wherein the reaction mixture comprises less than about 1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, adding 2,4-difluorophenyl-isocyanate is conducted at a rate sufficient to form the reaction mixture, wherein the reaction mixture comprises less than about 0.1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC.

In some embodiments, after the completion of adding 2,4-difluorophenyl-isocyanate, the reaction mixture is stirred until about 2% or less of the 3-(4-bromo-2-methyl-2H-pyrazol-3-yl)-4-methoxy-phenylamine is present in the reaction mixture with respect to the 1-[3-(4-bromo-2-methyl-2H-pyrazol-3-yl)-4-methoxy-phenyl]-3-(2,4-difluoro-phenyl)-urea as determined by HPLC. In some embodiments, after the completion of adding 2,4-difluorophenyl-isocyanate, the reaction mixture is stirred until about 1% or less of the 3-(4-bromo-2-methyl-2H-pyrazol-3-yl)-4-methoxy-phenylamine is present in the reaction mixture with respect to the 1-[3-(4-bromo-2-methyl-2H-pyrazol-3-yl)-4-methoxy-phenyl]-3-(2,4-difluoro-phenyl)-urea as determined by HPLC. In some embodiments, after the completion of adding 2,4-difluorophenyl-isocyanate, the reaction mixture is stirred until about 0.1% or less of the 3-(4-bromo-2-methyl-2H-pyrazol-3-yl)-4-methoxy-phenylamine is present in the reaction mixture with respect to the 1-[3-(4-bromo-2-methyl-2H-pyrazol-3-yl)-4-methoxy-phenyl]-3-(2,4-difluoro-phenyl)-urea as determined by HPLC.

Any suitable reverse or normal phase HPLC method can be used determine the percentage of 3-(4-bromo-2-methyl-2H-pyrazol-3-yl)-4-methoxy-phenylamine compared to 1-[3-(4-bromo-2-methyl-2H-pyrazol-3-yl)-4-methoxy-phenyl]-3-(2,4-difluoro-phenyl)-urea provided that the methods afford at least baseline resolution between the 3-(4-bromo-2-methyl-2H-pyrazol-3-yl)-4-methoxy-phenylamine HPLC signal and the 1-[3-(4-bromo-2-methyl-2H-pyrazol-3-yl)-4-methoxy-phenyl]-3-(2,4-difluoro-phenyl)-urea HPLC signal. One particularly useful method is as follows:

RP-HPLC: HPLC system, equipped with a detector, column oven, quaternary gradient pump, and auto sampler, such as an HPLC system form Waters Inc., Milford, Mass. or an equivalent. Detection wavelength set to 252 nm. The RP HPLC column is a Waters Symmetry Shield RP18, 3.5 μm, 4.6×150 mm or equivalent with a pre-column filter 0.5 μm (Upchurch Scientific). The run time is 37 minutes with an equilibration time of 5 minutes and an injection volume of 5 μL. The mobile phases include, Mobile Phase A: 0.1% TFA in water and Mobile Phase B: 0.1% TFA in Acetonitrile. The gradient is as follows:

| Time (min) | Flow Rate (mL/min) | % A | % B | Curve |
|---|---|---|---|---|
| 0.00 | 1.00 | 90 | 10 | 6 |
| 10.00 | 1.00 | 60 | 40 | 6 |
| 25.00 | 1.00 | 45 | 55 | 6 |
| 30.00 | 1.00 | 10 | 90 | 6 |
| 32.00 | 1.00 | 10 | 90 | 1 |
| 37.00 | 1.00 | 85 | 15 | 1 |

The retention time for 3-(4-bromo-2-methyl-2H-pyrazol-3-yl)-4-methoxy-phenylamine using this method is about 5.4 minutes (relative retention time of 0.24) with a relative response factor of 0.23. The retention time for 1-[3-(4-bromo-2-methyl-2H-pyrazol-3-yl)-4-methoxy-phenyl]-3-(2,4-difluoro-phenyl)-urea using this method is about 22.9 minutes (relative retention time of 1) with a relative response factor of 1.

In some embodiments, after the completion of adding 2,4-difluorophenyl-isocyanate, the reaction mixture is stirred for about 2 hours or less. In some embodiments, after the completion of adding 2,4-difluorophenyl-isocyanate, the reaction mixture is stirred for about 1.5 hours or less.

In some embodiments, crystallizing 1-[3-(4-bromo-2-methyl-2H-pyrazol-3-yl)-4-methoxy-phenyl]-3-(2,4-difluoro-phenyl)-urea is conducted at a temperature of about −30° C. to about 15° C. In some embodiments, crystallizing 1-[3-(4-bromo-2-methyl-2H-pyrazol-3-yl)-4-methoxy-phenyl]-3-(2,4-difluoro-phenyl)-urea is conducted at a temperature of about −25° C. to about 5° C. In some embodiments, crystallizing 1-[3-(4-bromo-2-methyl-2H-pyrazol-3-yl)-4-methoxy-phenyl]-3-(2,4-difluoro-phenyl)-urea is conducted at a temperature of about −15° C. to about 0° C. In some embodiments, crystallizing 1-[3-(4-bromo-2-methyl-2H-pyrazol-3-yl)-4-methoxy-phenyl]-3-(2,4-difluoro-phenyl)-urea is conducted at a temperature of about −10° C. to about −5° C.

In some embodiments, the process comprises:
reacting 3-(4-bromo-2-methyl-2H-pyrazol-3-yl)-4-methoxy-phenylamine with 2,4-difluorophenyl-isocyanate in the presence of acetonitrile is conducted by adding 2,4-difluorophenyl-isocyanate to 3-(4-bromo-2-methyl-2H-pyrazol-3-yl)-4-methoxy-phenylamine at a temperature of about −25° C. to about 0° C. and a rate sufficient to form the reaction mixture, wherein the reaction mixture comprises less than about 2% of 3-(4-bromo-2-methyl-2H-pyrazol-3-yl)-4-methoxy-phenylamine with respect to 1-[3-(4-bromo-2-methyl-2H-pyrazol-3-yl)-4-methoxy-phenyl]-3-(2,4-difluoro-phenyl)-urea as determined by HPLC; and
crystallizing 1-[3-(4-bromo-2-methyl-2H-pyrazol-3-yl)-4-methoxy-phenyl]-3-(2,4-difluoro-phenyl)-urea is conducted at a temperature of about −15° C. to about 0° C.

In some embodiments the process further comprises the step of isolating the acetonitrile solvate of 1-[3-(4-bromo-2-methyl-2H-pyrazol-3-yl)-4-methoxy-phenyl]-3-(2,4-difluoro-phenyl)-urea.

In some embodiments, isolating is conducted by filtration of the acetonitrile solvate of 1-[3-(4-bromo-2-methyl-2H-pyrazol-3-yl)-4-methoxy-phenyl]-3-(2,4-difluoro-phenyl)-urea from the reaction mixture.

4. Preparation of 3-(4-bromo-2-methyl-2H-pyrazol-3-yl)-4-methoxy-phenylamine from N-[3-(4-bromo-2-methyl-2H-pyrazol-3-yl)-4-methoxy-phenyl]-acetamide The compound 3-(4-bromo-2-methyl-2H-pyrazol-3-yl)-4-methoxy-phenylamine is an intermediate useful in the preparation of 1-[3-(4-bromo-2-methyl-2H-pyrazol-3-yl)-4-methoxy-phenyl]-3-(2,4-difluoro-phenyl)-urea (Compound I), crystalline forms and solvate forms thereof. There is a continuing effort to develop new processes for intermediates such as 3-(4-bromo-2-methyl-2H-pyrazol-3-yl)-4-methoxy-phenylamine that have improve efficiency with economic benefit and/or improved product purity. Novel processes for preparing 3-(4-bromo-2-methyl-2H-pyrazol-3-yl)-4-methoxy-phenylamine are described herein. The general process is illustrated in Scheme 2 below.

Scheme 2

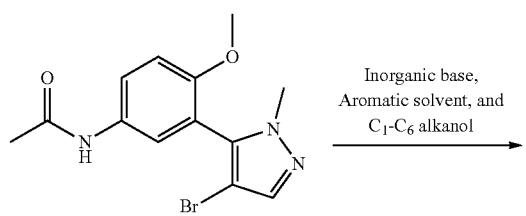

-continued

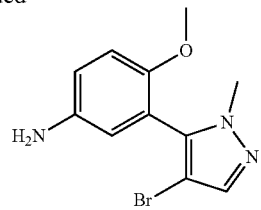

The starting material shown in Scheme 2, N-[4-methoxy-3-(2-methyl-2H-pyrazol-3-yl)-phenyl]-acetamide, can be prepared by a variety of suitable methods, for examples, such as those described in PCT Applications PCT/US2004/023880 and PCT/US2006/002721, both of which are incorporated herein by reference in their entirety.

Accordingly, one aspect of the present invention relates to processes for preparing 3-(4-bromo-2-methyl-2H-pyrazol-3-yl)-4-methoxy-phenylamine, the process comprising:

reacting N-[3-(4-bromo-2-methyl-2H-pyrazol-3-yl)-4-methoxy-phenyl]-acetamide with an inorganic base in the presence of a mixture of an aromatic solvent and a $C_1$-$C_6$ alkanol to form 3-(4-bromo-2-methyl-2H-pyrazol-3-yl)-4-methoxy-phenylamine.

In some embodiments, reacting N-[3-(4-bromo-2-methyl-2H-pyrazol-3-yl)-4-methoxy-phenyl]-acetamide with the inorganic base is conducted at a temperature of about 75° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 100° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 105° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 110° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 112° C.

Reacting N-[3-(4-bromo-2-methyl-2H-pyrazol-3-yl)-4-methoxy-phenyl]-acetamide can be performed in the presence of a suitable inorganic base. Suitable inorganic bases include alkali metal hydroxides and alkaline earth hydroxides. Examples of suitable bases include lithium hydroxide, sodium hydroxide, potassium hydroxide and the like.

In some embodiments, the inorganic base is an alkali metal hydroxide. In some embodiments, the inorganic base is sodium hydroxide.

Although reacting N-[3-(4-bromo-2-methyl-2H-pyrazol-3-yl)-4-methoxy-phenyl]-acetamide with an inorganic base can be conducted in the presence of water, one embodiment is directed to processes conducted without added water. Residual water present in reagents and solvents is excluded as "added" water in the context of this description. Accordingly, in some embodiments, reacting N-[3-(4-bromo-2-methyl-2H-pyrazol-3-yl)-4-methoxy-phenyl]-acetamide with an inorganic base is conducted in the presence of about 5% or less of water. In some embodiments, reacting N-[3-(4-bromo-2-methyl-2H-pyrazol-3-yl)-4-methoxy-phenyl]-acetamide with an inorganic base is conducted in the presence of about 4% or less of water. In some embodiments, reacting N-[3-(4-bromo-2-methyl-2H-pyrazol-3-yl)-4-methoxy-phenyl]-acetamide with an inorganic base is conducted in the presence of about 3% or less of water. In some embodiments, reacting N-[3-(4-bromo-2-methyl-2H-pyrazol-3-yl)-4-methoxy-phenyl]-acetamide with an inorganic base is conducted in the presence of about 2% or less of water. In some embodiments, reacting N-[3-(4-bromo-2-methyl-2H-pyrazol-3-yl)-4-methoxy-phenyl]-acetamide with an inorganic base is conducted in the presence of about 1% or less of water. In some embodiments, reacting N-[3-(4-bromo-2-methyl-2H-pyrazol-3-yl)-4-methoxy-phenyl]-acetamide with an inorganic base is conducted in the presence of about 0.5% or less of water.

In some embodiments, the aromatic solvent is xylene. In some embodiments, the aromatic solvent is a mixture of xylenes.

In some embodiments, the $C_1$-$C_6$ alkanol is n-propanol.

In some embodiments, the aromatic solvent is a mixture of xylenes and the $C_1$-$C_6$ alkanol is n-propanol. In some embodiments, the volume ratio of the mixture of xylenes to n-propanol is about 7:1 to about 1:1. In some embodiments, the volume ratio of the mixture of xylenes to n-propanol is about 6:1 to about 4:1. In some embodiments, the volume ratio of the mixture of xylenes to n-propanol is about 5:1.

In some embodiments, the process comprises:

reacting N-[3-(4-bromo-2-methyl-2H-pyrazol-3-yl)-4-methoxy-phenyl]-acetamide with the inorganic base is conducted at a temperature of about 75° C. to about reflux temperature;

and wherein:

the inorganic base is sodium hydroxide;

the aromatic solvent is a mixture of xylenes; and the $C_1$-$C_6$ alkanol is n-propanol; wherein the volume ratio of the mixture of xylenes to n-propanol is about 5:1.

Particular processes that are useful for preparing N-[3-(4-bromo-2-methyl-2H-pyrazol-3-yl)-4-methoxy-phenyl]-acetamide are described herein.

Accordingly, in some embodiments, N-[3-(4-bromo-2-methyl-2H-pyrazol-3-yl)-4-methoxy-phenyl]-acetamide is prepared by the process comprising:

reacting N-[4-methoxy-3-(2-methyl-2H-pyrazol-3-yl)-phenyl]-acetamide with a brominating agent in the presence of a brominating solvent to form the N-[3-(4-bromo-2-methyl-2H-pyrazol-3-yl)-4-methoxy-phenyl]-acetamide, the general process is illustrated in Scheme 3 below.

Scheme 3

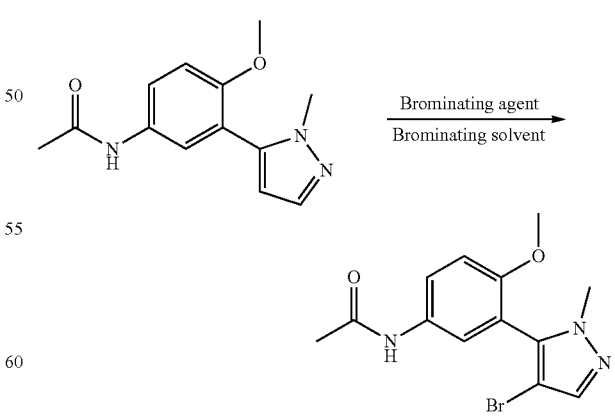

The starting material shown in Scheme 3, N-[4-methoxy-3-(2-methyl-2H-pyrazol-3-yl)-phenyl]-acetamide, can be prepared by a variety of suitable methods, for examples, such as those described in PCT Applications PCT/US2004/

023880 and PCT/US2006/002721, both of which are incorporated herein by reference in their entirety.

In some embodiments, reacting N-[4-methoxy-3-(2-methyl-2H-pyrazol-3-yl)-phenyl]-acetamide with the brominating agent is conducted at a temperature of about 25° C. to about 100° C. In some embodiments, reacting N-[4-methoxy-3-(2-methyl-2H-pyrazol-3-yl)-phenyl]-acetamide with the brominating agent is conducted at a temperature of about 25° C. to about 75° C. In some embodiments, reacting N-[4-methoxy-3-(2-methyl-2H-pyrazol-3-yl)-phenyl]-acetamide with the brominating agent is conducted at a temperature of about 25° C. to about 65° C. In some embodiments, reacting N-[4-methoxy-3-(2-methyl-2H-pyrazol-3-yl)-phenyl]-acetamide with the brominating agent is conducted at a temperature of about 35° C. to about 65° C.

In some embodiments, reacting N-[4-methoxy-3-(2-methyl-2H-pyrazol-3-yl)-phenyl]-acetamide with the brominating agent is conducted under a nitrogen atmosphere.

In some embodiments, reacting N-[4-methoxy-3-(2-methyl-2H-pyrazol-3-yl)-phenyl]-acetamide with the brominating agent is conducted by adding the brominating agent to the N-[4-methoxy-3-(2-methyl-2H-pyrazol-3-yl)-phenyl]-acetamide in the brominating solvent.

Any suitable brominating agent can be used in the aforementioned process to prepare N-[3-(4-bromo-2-methyl-2H-pyrazol-3-yl)-4-methoxy-phenyl]-acetamide. Suitable brominating agents include, for example, $Br_2$, N-bromosuccinimide (NBS), 1,3-dibromo-5,5-dimethylhydantoin, pyridinium tribromide ($pyrHBr_3$) and the like.

In some embodiments, the brominating agent is N-bromosuccinimide.

The molar ratio of brominating agent to N-[4-methoxy-3-(2-methyl-2H-pyrazol-3-yl)-phenyl]-acetamide can routinely be selected or optimized by the skilled artisan. In general the brominating agent is presence in excess compared to N-[4-methoxy-3-(2-methyl-2H-pyrazol-3-yl)-phenyl]-acetamide. In some embodiments, the molar ratio of brominating agent to N-[4-methoxy-3-(2-methyl-2H-pyrazol-3-yl)-phenyl]-acetamide is selected from about 2:1, about 1.9:1, about 1.8:1, about 1.7:1, about 1.6:1, about 1.5:1, about 1.4:1, about 1.3:1, about 1.2:1, about 1.1:1 and about 1:1.

Any suitable brominating solvent can be used in the aforementioned process to prepare N-[3-(4-bromo-2-methyl-2H-pyrazol-3-yl)-4-methoxy-phenyl]-acetamide provided that each reagent in the process is sufficiently soluble in the brominating solvent. Suitable brominating solvents include, for example, N,N-dimethylacetamide, N,N-dimethylformamide and the like.

In some embodiments, the brominating solvent is N,N-dimethylacetamide.

In some embodiments, the brominating agent is N-bromosuccinimide and the brominating solvent is N,N-dimethylacetamide.

In some embodiments, the process comprises:
reacting N-[4-methoxy-3-(2-methyl-2H-pyrazol-3-yl)-phenyl]-acetamide with the brominating agent is conducted at a temperature of about 35° C. to about 65° C.;
the brominating agent is N-bromosuccinimide; and
the brominating solvent is N,N-dimethylacetamide.

5. Preparation of 1-[3-(4-Bromo-2-methyl-2H-pyrazol-3-yl)-4-methoxy-phenyl]-3-(2,4-difluoro-phenyl)-urea from 3-(4-Bromo-2-methyl-2H-pyrazol-3-yl)-4-methoxy-phenylamine Also provided in the present invention are novel processes for the preparation of 1-[3-(4-bromo-2-methyl-2H-pyrazol-3-yl)-4-methoxy-phenyl]-3-(2,4-difluoro-phenyl)-urea that utilize the step of preparing 3-(4-bromo-2-methyl-2H-pyrazol-3-yl)-4-methoxy-phenylamine from N-[3-(4-bromo-2-methyl-2H-pyrazol-3-yl)-4-methoxy-phenyl]-acetamide.

Accordingly, one aspect of the present invention relates to processes for preparing 1-[3-(4-bromo-2-methyl-2H-pyrazol-3-yl)-4-methoxy-phenyl]-3-(2,4-difluoro-phenyl)-urea comprising the steps of:
reacting N-[3-(4-bromo-2-methyl-2H-pyrazol-3-yl)-4-methoxy-phenyl]-acetamide with an inorganic base in the presence of a mixture of an aromatic solvent and a $C_1$-$C_6$ alkanol to form 3-(4-bromo-2-methyl-2H-pyrazol-3-yl)-4-methoxy-phenylamine; and
reacting 3-(4-bromo-2-methyl-2H-pyrazol-3-yl)-4-methoxy-phenylamine with 2,4-difluorophenyl-isocyanate in the presence of a urea-forming solvent to form 1-[3-(4-bromo-2-methyl-2H-pyrazol-3-yl)-4-methoxy-phenyl]-3-(2,4-difluoro-phenyl)-urea.

Another aspect of the present invention relates to processes for preparing 1-[3-(4-bromo-2-methyl-2H-pyrazol-3-yl)-4-methoxy-phenyl]-3-(2,4-difluoro-phenyl)-urea comprising the steps of:
a) reacting N-[4-methoxy-3-(2-methyl-2H-pyrazol-3-yl)-phenyl]-acetamide with a brominating agent in the presence of a brominating solvent to form the N-[3-(4-bromo-2-methyl-2H-pyrazol-3-yl)-4-methoxy-phenyl]-acetamide;
b) reacting N-[3-(4-bromo-2-methyl-2H-pyrazol-3-yl)-4-methoxy-phenyl]-acetamide with an inorganic base in the presence of a mixture of an aromatic solvent and a $C_1$-$C_6$ alkanol to form 3-(4-bromo-2-methyl-2H-pyrazol-3-yl)-4-methoxy-phenylamine; and
c) reacting 3-(4-bromo-2-methyl-2H-pyrazol-3-yl)-4-methoxy-phenylamine with 2,4-difluorophenyl-isocyanate in the presence of a urea-forming solvent to form 1-[3-(4-bromo-2-methyl-2H-pyrazol-3-yl)-4-methoxy-phenyl]-3-(2,4-difluoro-phenyl)-urea.

5a. Formation of N-[3-(4-bromo-2-methyl-2H-pyrazol-3-yl)-4-methoxy-phenyl]-acetamide from N-[4-methoxy-3-(2-methyl-2H-pyrazol-3-yl)-phenyl]-acetamide In some embodiments, reacting N-[4-methoxy-3-(2-methyl-2H-pyrazol-3-yl)-phenyl]-acetamide with the brominating agent is conducted at a temperature of about 25° C. to about 100° C. In some embodiments, reacting N-[4-methoxy-3-(2-methyl-2H-pyrazol-3-yl)-phenyl]-acetamide with the brominating agent is conducted at a temperature of about 25° C. to about 75° C. In some embodiments, reacting N-[4-methoxy-3-(2-methyl-2H-pyrazol-3-yl)-phenyl]-acetamide with the brominating agent is conducted at a temperature of about 25° C. to about 65° C. In some embodiments, reacting N-[4-methoxy-3-(2-methyl-2H-pyrazol-3-yl)-phenyl]-acetamide with the brominating agent is conducted at a temperature of about 35° C. to about 65° C.

In some embodiments, reacting N-[4-methoxy-3-(2-methyl-2H-pyrazol-3-yl)-phenyl]-acetamide with the brominating agent is conducted under a nitrogen atmosphere.

In some embodiments, reacting N-[4-methoxy-3-(2-methyl-2H-pyrazol-3-yl)-phenyl]-acetamide with the brominating agent is conducted by adding the brominating agent to the N-[4-methoxy-3-(2-methyl-2H-pyrazol-3-yl)-phenyl]-acetamide in the brominating solvent.

Any suitable brominating agent can be used in the aforementioned processes to prepare N-[3-(4-bromo-2-methyl-2H-pyrazol-3-yl)-4-methoxy-phenyl]-acetamide. Suitable brominating agents include, for example, $Br_2$, N-bromosuccinimide (NBS), 1,3-dibromo-5,5-dimethylhydantoin, pyridinium tribromide (pyrHBr₃) and the like.

In some embodiments, the brominating agent is N-bromosuccinimide.

The molar ratio of brominating agent to N-[4-methoxy-3-(2-methyl-2H-pyrazol-3-yl)-phenyl]-acetamide can routinely be selected or optimized by the skilled artisan. In general the brominating agents is presence in excess compared to N-[4-methoxy-3-(2-methyl-2H-pyrazol-3-yl)-phenyl]-acetamide. In some embodiments, the molar ratio of brominating agent to N-[4-methoxy-3-(2-methyl-2H-pyrazol-3-yl)-phenyl]-acetamide is selected from about 2:1, about 1.9:1, about 1.8:1, about 1.7:1, about 1.6:1, about 1.5:1, about 1.4:1, about 1.3:1, about 1.2:1, about 1.1:1 and about 1:1.

Any suitable brominating solvent can be used in the aforementioned processes to prepare N-[3-(4-bromo-2-methyl-2H-pyrazol-3-yl)-4-methoxy-phenyl]-acetamide provided that each reagent in the process is sufficiently soluble in the brominating solvent. Suitable brominating solvents include, for example, N,N-dimethylacetamide, N,N-dimethylformamide, tetrahydrofuran and the like.

In some embodiments, the brominating solvent is N,N-dimethylacetamide.

In some embodiments, the brominating agent is N-bromosuccinimide and the brominating solvent is N,N-dimethylacetamide.

In some embodiments, the process comprises:
reacting N-[4-methoxy-3-(2-methyl-2H-pyrazol-3-yl)-phenyl]-acetamide with the brominating agent is conducted at a temperature of about 35° C. to about 65° C.;
the brominating agent is N-bromosuccinimide; and
the brominating solvent is N,N-dimethylacetamide.

5b. Formation of 3-(4-bromo-2-methyl-2H-pyrazol-3-yl)-4-methoxy-phenylamine from N-[3-(4-bromo-2-methyl-2H-pyrazol-3-yl)-4-methoxy-phenyl]-acetamide In some embodiments, reacting N-[3-(4-bromo-2-methyl-2H-pyrazol-3-yl)-4-methoxy-phenyl]-acetamide with the inorganic base is conducted at a temperature of about 75° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 100° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 105° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 110° C. to about reflux temperature. In some embodiments, reacting N-[3-(4-bromo-2-methyl-2H-pyrazol-3-yl)-4-methoxy-phenyl]-acetamide with the inorganic base is conducted at a temperature of about 112° C.

Reacting N-[3-(4-bromo-2-methyl-2H-pyrazol-3-yl)-4-methoxy-phenyl]-acetamide can be performed in the presence of any suitable inorganic base. Suitable inorganic bases include alkali metal hydroxides and alkaline earth hydroxides. Examples of suitable inorganic bases include lithium hydroxide, sodium hydroxide, potassium hydroxide and the like.

In some embodiments, the inorganic base is an alkali metal hydroxide. In some embodiments, the inorganic base is sodium hydroxide.

Although reacting N-[3-(4-bromo-2-methyl-2H-pyrazol-3-yl)-4-methoxy-phenyl]-acetamide with an inorganic base can be conducted in the presence of water, one embodiment is directed to processes conducted without added water. Residual water present in reagents and solvents is excluded as "added" water in the context of this description. Accordingly, in some embodiments, reacting N-[3-(4-bromo-2-methyl-2H-pyrazol-3-yl)-4-methoxy-phenyl]-acetamide with an inorganic base is conducted in the presence of about 5% or less of water. In some embodiments, reacting N-[3-(4-bromo-2-methyl-2H-pyrazol-3-yl)-4-methoxy-phenyl]-acetamide with an inorganic base is conducted in the presence of about 4% or less of water. In some embodiments, reacting N-[3-(4-bromo-2-methyl-2H-pyrazol-3-yl)-4-methoxy-phenyl]-acetamide with an inorganic base is conducted in the presence of about 3% or less of water. In some embodiments, reacting N-[3-(4-bromo-2-methyl-2H-pyrazol-3-yl)-4-methoxy-phenyl]-acetamide with an inorganic base is conducted in the presence of about 2% or less of water. In some embodiments, reacting N-[3-(4-bromo-2-methyl-2H-pyrazol-3-yl)-4-methoxy-phenyl]-acetamide with an inorganic base is conducted in the presence of about 1% or less of water. In some embodiments, reacting N-[3-(4-bromo-2-methyl-2H-pyrazol-3-yl)-4-methoxy-phenyl]-acetamide with an inorganic base is conducted in the presence of about 0.5% or less of water.

In some embodiments, the aromatic solvent is xylene. In some embodiments, the aromatic solvent is a mixture of xylenes.

In some embodiments, the $C_1$-$C_6$ alkanol is n-propanol.

In some embodiments, the aromatic solvent is a mixture of xylenes and $C_1$-$C_6$ alkanol is n-propanol.

In some embodiments, the volume ratio of the mixture of xylenes to n-propanol is about 7:1 to about 1:1. In some embodiments, the volume ratio of the mixture of xylenes to n-propanol is about 6:1 to about 4:1. In some embodiments, the volume ratio of the mixture of xylenes to n-propanol is about 5:1.

In some embodiments, the process comprises:
reacting N-[3-(4-bromo-2-methyl-2H-pyrazol-3-yl)-4-methoxy-phenyl]-acetamide with the inorganic base is conducted at a temperature of about 75° C. to about reflux temperature; and
wherein:
the inorganic base is sodium hydroxide;
the aromatic solvent is a mixture of xylenes; and
the $C_1$-$C_6$ alkanol is n-propanol; wherein the volume ratio of the mixture of xylenes to n-propanol is about 5:1.

5c. Formation of 1-[3-(4-bromo-2-methyl-2H-pyrazol-3-yl)-4-methoxy-phenyl]-3-(2,4-difluoro-phenyl)-urea from 3-(4-bromo-2-methyl-2H-pyrazol-3-yl)-4-methoxy-phenylamine In some embodiments, reacting 3-(4-bromo-2-methyl-2H-pyrazol-3-yl)-4-methoxy-phenylamine with 2,4-difluorophenyl-isocyanate is conducted under a nitrogen atmosphere.

In some embodiments, reacting 3-(4-bromo-2-methyl-2H-pyrazol-3-yl)-4-methoxy-phenylamine with 2,4-difluorophenyl-isocyanate is conducted in the presence of about 10% of $H_2O$ or less. In some embodiments, reacting 3-(4-bromo-2-methyl-2H-pyrazol-3-yl)-4-methoxy-phenylamine with 2,4-difluorophenyl-isocyanate is conducted in the presence of about 1% of $H_2O$ or less. In some embodiments, reacting 3-(4-bromo-2-methyl-2H-pyrazol-3-yl)-4- methoxy-phenylamine with 2,4-difluorophenyl-isocyanate is conducted in the presence of about 0.1% of H$_2$O or less.

In some embodiments, reacting 3-(4-bromo-2-methyl-2H-pyrazol-3-yl)-4-methoxy-phenylamine with 2,4-difluorophenyl-isocyanate is conducted at a temperature of about −30° C. to about 10° C. In some embodiments, reacting 3-(4-bromo-2-methyl-2H-pyrazol-3-yl)-4-methoxy-phenylamine with 2,4-difluorophenyl-isocyanate is conducted at a temperature of about −25° C. to about 0° C. In some embodiments, reacting 3-(4-bromo-2-methyl-2H-pyrazol-3-yl)-4-methoxy-phenylamine with 2,4-difluorophenyl-isocyanate is conducted at a temperature of about −15° C. to about −5° C.

In some embodiments, reacting 3-(4-bromo-2-methyl-2H-pyrazol-3-yl)-4-methoxy-phenylamine with 2,4-difluorophenyl-isocyanate is conducted by adding the 2,4-difluorophenyl-isocyanate to the 3-(4-bromo-2-methyl-2H-pyrazol-3-yl)-4-methoxy-phenylamine in acetonitrile to form a reaction mixture.

In some embodiments, the reaction mixture comprises less than about 2% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, the reaction mixture comprises less than about 1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, the reaction mixture comprises less than about 0.1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC.

In some embodiments, adding 2,4-difluorophenyl-isocyanate is conducted at a rate sufficient to form the reaction mixture, wherein the reaction mixture comprises less than about 2% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, adding 2,4-difluorophenyl-isocyanate is conducted at a rate sufficient to form the reaction mixture, wherein the reaction mixture comprises less than about 1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC. In some embodiments, adding 2,4-difluorophenyl-isocyanate is conducted at a rate sufficient to form the reaction mixture, wherein the reaction mixture comprises less than about 0.1% of the 3-(4-bromo-2-methyl-2H-pyrazol-3-yl)-4-methoxy-phenylamine with respect to the 1-[3-(4-bromo-2-methyl-2H-pyrazol-3-yl)-4-methoxy-phenyl]-3-(2,4-difluoro-phenyl)-urea as determined by HPLC.

In some embodiments, after the completion of adding 2,4-difluorophenyl-isocyanate, the reaction mixture is stirred until about 2% or less of the 3-(4-bromo-2-methyl-2H-pyrazol-3-yl)-4-methoxy-phenylamine is present in the reaction mixture with respect to the 1-[3-(4-bromo-2-methyl-2H-pyrazol-3-yl)-4-methoxy-phenyl]-3-(2,4-difluoro-phenyl)-urea as determined by HPLC. In some embodiments, after the completion of adding 2,4-difluorophenyl-isocyanate, the reaction mixture is stirred until about 1% or less of the 3-(4-bromo-2-methyl-2H-pyrazol-3-yl)-4-methoxy-phenylamine is present in the reaction mixture with respect to the 1-[3-(4-bromo-2-methyl-2H-pyrazol-3-yl)-4-methoxy-phenyl]-3-(2,4-difluoro-phenyl)-urea as determined by HPLC. In some embodiments, after the completion of adding 2,4-difluorophenyl-isocyanate, the reaction mixture is stirred until about 0.1% or less of the 3-(4-bromo-2-methyl-2H-pyrazol-3-yl)-4-methoxy-phenylamine is present in the reaction mixture with respect to the 1-[3-(4-bromo-2-methyl-2H-pyrazol-3-yl)-4-methoxy-phenyl]-3-(2,4-difluoro-phenyl)-urea as determined by HPLC.

In some embodiments, after the completion of adding 2,4-difluorophenyl-isocyanate, the reaction mixture is stirred for about 2 hours or less. In some embodiments, after the completion of adding 2,4-difluorophenyl-isocyanate, the reaction mixture is stirred for about 1.5 hours or less.

In some embodiments the process further comprises the step of isolating the 1-[3-(4-bromo-2-methyl-2H-pyrazol-3-yl)-4-methoxy-phenyl]-3-(2,4-difluoro-phenyl)-urea from the reaction mixture comprising 1-[3-(4-bromo-2-methyl-2H-pyrazol-3-yl)-4-methoxy-phenyl]-3-(2,4-difluoro-phenyl)-urea and the urea-forming solvent. In some embodiments, the isolating is conducted by filtration of the 1-[3-(4-bromo-2-methyl-2H-pyrazol-3-yl)-4-methoxy-phenyl]-3-(2,4-difluoro-phenyl)-urea from the reaction mixture comprising 1-[3-(4-bromo-2-methyl-2H-pyrazol-3-yl)-4-methoxy-phenyl]-3-(2,4-difluoro-phenyl)-urea and the urea-forming solvent.

Any suitable urea-forming solvent can be used in the aforementioned process to prepare 1-[3-(4-bromo-2-methyl-2H-pyrazol-3-yl)-4-methoxy-phenyl]-3-(2,4-difluoro-phenyl)-urea. Representative urea-forming solvents include but not limited to aromatic solvents (e.g., benzene, toluene, and the like), N,N-dimethylformamide (DMF), N,N-dimethylacetamide (DMA), methylsulfoxide, acetonitrile, ethyl acetate, methylene chloride, mixtures thereof and the like. One particularly useful solvent is acetonitrile as this solvent provides advantages over other solvents, such as, providing the acetonitrile solvate that can be converted to Form I of 1-[3-(4-bromo-2-methyl-2H-pyrazol-3-yl)-4-methoxy-phenyl]-3-(2,4-difluoro-phenyl)-urea.

In some embodiments, the urea-forming solvent is acetonitrile.

In some embodiments the process further comprises the step of crystallizing the 1-[3-(4-bromo-2-methyl-2H-pyrazol-3-yl)-4-methoxy-phenyl]-3-(2,4-difluoro-phenyl)-urea from the reaction mixture to form a acetonitrile solvate of 1-[3-(4-bromo-2-methyl-2H-pyrazol-3-yl)-4-methoxy-phenyl]-3-(2,4-difluoro-phenyl)-urea.

In some embodiments, the acetonitrile solvate of 1-[3-(4-bromo-2-methyl-2H-pyrazol-3-yl)-4-methoxy-phenyl]-3-(2,4-difluoro-phenyl)-urea has a molecular ratio of acetonitrile to 1-[3-(4-bromo-2-methyl-2H-pyrazol-3-yl)-4-methoxy-phenyl]-3-(2,4-difluoro-phenyl)-urea of about 1:2.

In some embodiments, the crystallizing is conducted at a temperature of about −30° C. to about 15° C. In some embodiments, the crystallizing is conducted at a temperature of about −25° C. to about 5° C. In some embodiments, the crystallizing is conducted at a temperature of about −15° C. to about 0° C. In some embodiments, the crystallizing is conducted at a temperature of about −10° C. to about −5° C.

In some embodiments the process further comprises the step of isolating the acetonitrile solvate of 1-[3-(4-bromo-2-methyl-2H-pyrazol-3-yl)-4-methoxy-phenyl]-3-(2,4-difluoro-phenyl)-urea. In some embodiments, the isolating is conducted by filtration of the acetonitrile solvate of 1-[3-(4-bromo-2-methyl-2H-pyrazol-3-yl)-4-methoxy-phenyl]-3-(2,4-difluoro-phenyl)-urea from the reaction mixture.

In some embodiments the process further comprises the step of converting the acetonitrile solvate of 1-[3-(4-bromo-2-methyl-2H-pyrazol-3-yl)-4-methoxy-phenyl]-3-(2,4-difluoro-phenyl)-urea.

In some embodiments the process further comprises the step of converting the acetonitrile solvate of 1-[3-(4-bromo-2-methyl-2H-pyrazol-3-yl)-4-methoxy-phenyl]-3-(2,4-difluoro-phenyl)-urea to form I of 1-[3-(4-bromo-2-methyl-2H-pyrazol-3-yl)-4-methoxy-phenyl]-3-(2,4-difluoro-phenyl)-urea.

In some embodiments, the converting of the acetonitrile solvate of 1-[3-(4-bromo-2-methyl-2H-pyrazol-3-yl)-4-methoxy-phenyl]-3-(2,4-difluoro-phenyl)-urea is conducted under reduced pressure.

In some embodiments, the converting of the acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 100 mm Hg or less. In some embodiments, the converting of the acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 35 mm Hg or less. In some embodiments, the converting of the acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 10 mm Hg or less. In some embodiments, the converting of the acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 5 mm Hg or less.

In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted during at least two time periods, wherein the conversion is conducted at a first temperature during a first time period and wherein the conversion is conducted at a second temperature during a second time period, and wherein the first temperature is not equivalent to the second temperature.

In some embodiments, the second temperature is higher than the first temperature. In some embodiments, the first temperature is at about 0° C. to about 45° C. In some embodiments, the first temperature is at about 15° C. to about 40° C. In some embodiments, the first temperature is at about 20° C. to about 30° C.

In some embodiments, the second temperature is about 45° C. to about 90° C. In some embodiments, the second temperature is about 60° C. to about 80° C. In some embodiments, the second temperature is about 65° C. to about 75° C.

In some embodiments, the first temperature is at about 20° C. to about 30° C. and the second temperature is about 65° C. to about 75° C.

In some embodiments the process further comprises the step of maintaining the first temperature until a loss on drying (LOD) for a representative sample from the process is at a level of about 30% or less. In some embodiments the process further comprises the step of maintaining the first temperature until a loss on drying (LOD) for a representative sample from the process is at a level of about 20% or less. In some embodiments the process further comprises the step of maintaining the first temperature until a loss on drying (LOD) for a representative sample from the process is at a level of about 15% or less. In some embodiments the process further comprises the step of maintaining the first temperature until a loss on drying (LOD) for a representative sample from the process is at a level of about 10% or less.

In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 0° C. to about 45° C. until a loss on drying (LOD) for a representative sample from the process is at a level of about 30% or less and thereafter raising to a second temperature of about 45° C. to about 90° C. In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 15° C. to about 40° C. until a loss on drying (LOD) for a representative sample from the process is at a level of about 20% or less and thereafter raising to a second temperature about 60° C. to about 80° C. In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 20° C. to about 30° C. until a loss on drying (LOD) for a representative sample from the process is at a level of about 15% or less and thereafter raising to a second temperature of about 60° C. to about 80° C. In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a first temperature of about 20° C. to about 30° C. until a loss on drying (LOD) for a representative sample from the process is at a level of about 10% or less and thereafter raising to a second temperature of about 65° C. to about 75° C.

In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 35 mm Hg or less at a first temperature of about 20° C. to about 30° C. until a loss on drying (LOD) for a representative sample from the process is at a level of about 10% or less; and thereafter raising the first temperature to a second temperature of about 65° C. to about 75° C. while maintaining the reduced pressure of about 35 mm Hg or less.

6. Preparation of Form I of 1-[3-(4-bromo-2-methyl-2H-pyrazol-3-yl)-4-methoxy-phenyl]-3-(2,4-difluoro-phenyl)-urea Also provided in the present invention are processes that are particularly useful for reprocessing/recrystallizing 1-[3-(4-bromo-2-methyl-2H-pyrazol-3-yl)-4-methoxy-phenyl]-3-(2,4-difluoro-phenyl)-urea that may have undesirable levels of impurities, polymorphs, contaminants, reagents, solvents or the like to give Form I of 1-[3-(4-bromo-2-methyl-2H-pyrazol-3-yl)-4-methoxy-phenyl]-3-(2,4-difluoro-phenyl)-urea. These processes can utilize a variety of physical forms of 1-[3-(4-bromo-2-methyl-2H-pyrazol-3-yl)-4-methoxy-phenyl]-3-(2,4-difluoro-phenyl)-urea as the starting material, for example, Form I, Form II, Form IV, amorphous material or mixtures thereof.

Accordingly, the present invention relates to processes for preparing Form I of 1-[3-(4-bromo-2-methyl-2H-pyrazol-3-yl)-4-methoxy-phenyl]-3-(2,4-difluoro-phenyl)-urea, the process comprising:

a) dissolving 1-[3-(4-bromo-2-methyl-2H-pyrazol-3-yl)-4-methoxy-phenyl]-3-(2,4-difluoro-phenyl)-urea in tetrahydrofuran to form a solution;

b) adding an aliphatic solvent to the solution to form a mixture comprising a first solvate of 1-[3-(4-bromo-2-methyl-2H-pyrazol-3-yl)-4-methoxy-phenyl]-3-(2,4-difluoro-phenyl)-urea;

c) isolating the first solvate of 1-[3-(4-bromo-2-methyl-2H-pyrazol-3-yl)-4-methoxy-phenyl]-3-(2,4-difluoro-phenyl)-urea from the mixture to provide an isolated first solvate of 1-[3-(4-bromo-2-methyl-2H-pyrazol-3-yl)-4-methoxy-phenyl]-3-(2,4-difluoro-phenyl)-urea; and d) converting the isolated first solvate to provide Form I of 1-[3-(4-bromo-2-methyl-2H-pyrazol-3-yl)-4-methoxy-phenyl]-3-(2,4-difluoro-phenyl)-urea. This embodiment provides processes that give Form I of 1-[3-(4-bromo-2-methyl-2H-pyrazol-3-yl)-4-methoxy-phenyl]-3-(2,4-difluoro-phenyl)-urea with good purity and under certain circumstances these processes are acceptable if trace amounts of aliphatic solvent can be tolerated. However, in the example where the aliphatic solvent is heptane, ICH guidelines suggest that the maximum level of heptane to be about 5000 ppm. As a result, it was found that by washing the first solvate of 1-[3-(4-bromo-2-methyl-2H-pyrazol-3-yl)-4-methoxy-phenyl]-3-(2,4-difluoro-phenyl)-urea with acetonitrile provided a second solvate that could subsequently be converted to Form I of 1-[3-(4-bromo-2-methyl-2H-pyrazol-3-yl)-4-methoxy-phenyl]-3-(2,4-difluoro-phenyl)-urea with solvent levels below ICH guidelines.

Accordingly, another aspect of the present invention relates to processes for preparing Form I of 1-[3-(4-bromo-2-methyl-2H-pyrazol-3-yl)-4-methoxy-phenyl]-3-(2,4-difluoro-phenyl)-urea, the process comprising:

a) dissolving 1-[3-(4-bromo-2-methyl-2H-pyrazol-3-yl)-4-methoxy-phenyl]-3-(2,4-difluoro-phenyl)-urea in tetrahydrofuran to form a solution;

b) adding an aliphatic solvent to the solution to form a mixture comprising a first solvate of 1-[3-(4-bromo-2-methyl-2H-pyrazol-3-yl)-4-methoxy-phenyl]-3-(2,4-difluoro-phenyl)-urea;

c) isolating the first solvate of 1-[3-(4-bromo-2-methyl-2H-pyrazol-3-yl)-4-methoxy-phenyl]-3-(2,4-difluoro-phenyl)-urea from the mixture to provide an isolated first solvate of 1-[3-(4-bromo-2-methyl-2H-pyrazol-3-yl)-4-methoxy-phenyl]-3-(2,4-difluoro-phenyl)-urea;

d) washing the isolated first solvate of 1-[3-(4-bromo-2-methyl-2H-pyrazol-3-yl)-4-methoxy-phenyl]-3-(2,4-difluoro-phenyl)-urea with acetonitrile to form a second solvate of 1-[3-(4-bromo-2-methyl-2H-pyrazol-3-yl)-4-methoxy-phenyl]-3-(2,4-difluoro-phenyl)-urea; and e) converting the second solvate to provide Form I of 1-[3-(4-bromo-2-methyl-2H-pyrazol-3-yl)-4-methoxy-phenyl]-3-(2,4-difluoro-phenyl)-urea.

In some embodiments, the dissolving 1-[3-(4-bromo-2-methyl-2H-pyrazol-3-yl)-4-methoxy-phenyl]-3-(2,4-difluoro-phenyl)-urea in tetrahydrofuran is conducted at a weight ratio of 1-[3-(4-bromo-2-methyl-2H-pyrazol-3-yl)-4-methoxy-phenyl]-3-(2,4-difluoro-phenyl)-urea to tetrahydrofuran of about 1:6 to about 1:5. In some embodiments, the dissolving 1-[3-(4-bromo-2-methyl-2H-pyrazol-3-yl)-4-methoxy-phenyl]-3-(2,4-difluoro-phenyl)-urea in tetrahydrofuran is conducted at a weight ratio of 1-[3-(4-bromo-2-methyl-2H-pyrazol-3-yl)-4-methoxy-phenyl]-3-(2,4-difluoro-phenyl)-urea to tetrahydrofuran of about 1.3:5.6. In some embodiments, the dissolving 1-[3-(4-bromo-2-methyl-2H-pyrazol-3-yl)-4-methoxy-phenyl]-3-(2,4-difluoro-phenyl)-urea in tetrahydrofuran is conducted at a temperature of about 25° C. to about reflux temperature.

In some embodiments, the dissolving 1-[3-(4-bromo-2-methyl-2H-pyrazol-3-yl)-4-methoxy-phenyl]-3-(2,4-difluoro-phenyl)-urea in tetrahydrofuran is conducted at a temperature of about 55° C. to about reflux temperature. In some embodiments, the dissolving 1-[3-(4-bromo-2-methyl-2H-pyrazol-3-yl)-4-methoxy-phenyl]-3-(2,4-difluoro-phenyl)-urea in tetrahydrofuran is conducted at a temperature of about 60° C. to about reflux temperature. In some embodiments, the dissolving 1-[3-(4-bromo-2-methyl-2H-pyrazol-3-yl)-4-methoxy-phenyl]-3-(2,4-difluoro-phenyl)-urea in tetrahydrofuran is conducted at or about reflux temperature. In some embodiments the process further comprises the step of cooling the solution of 1-[3-(4-bromo-2-methyl-2H-pyrazol-3-yl)-4-methoxy-phenyl]-3-(2,4-difluoro-phenyl)-urea in tetrahydrofuran in step a) prior to step b).

In some embodiments, the cooling is to a temperature of about −35° C. to about 10° C. In some embodiments, the cooling is to a temperature of about −25° C. to about −5° C.

In some embodiments, adding heptane to the solution to form a first solvate of 1-[3-(4-bromo-2-methyl-2H-pyrazol-3-yl)-4-methoxy-phenyl]-3-(2,4-difluoro-phenyl)-urea is conducted at a temperature of about −35° C. to about 10° C. In some embodiments, adding heptane to the solution to form a first solvate of 1-[3-(4-bromo-2-methyl-2H-pyrazol-3-yl)-4-methoxy-phenyl]-3-(2,4-difluoro-phenyl)-urea is conducted at a temperature of about −25° C. to about −5° C.

In some embodiments, the aliphatic solvent is a $C_5$-$C_{10}$ alkane, a $C_5$-$C_8$ cycloalkane or a mixture thereof. In some embodiments, the aliphatic solvent is a $C_5$-$C_{10}$ alkane. In some embodiments, the aliphatic solvent is hexane. In some embodiments, the aliphatic solvent is cyclohexane. In some embodiments, the aliphatic solvent is heptane.

Figure 29:
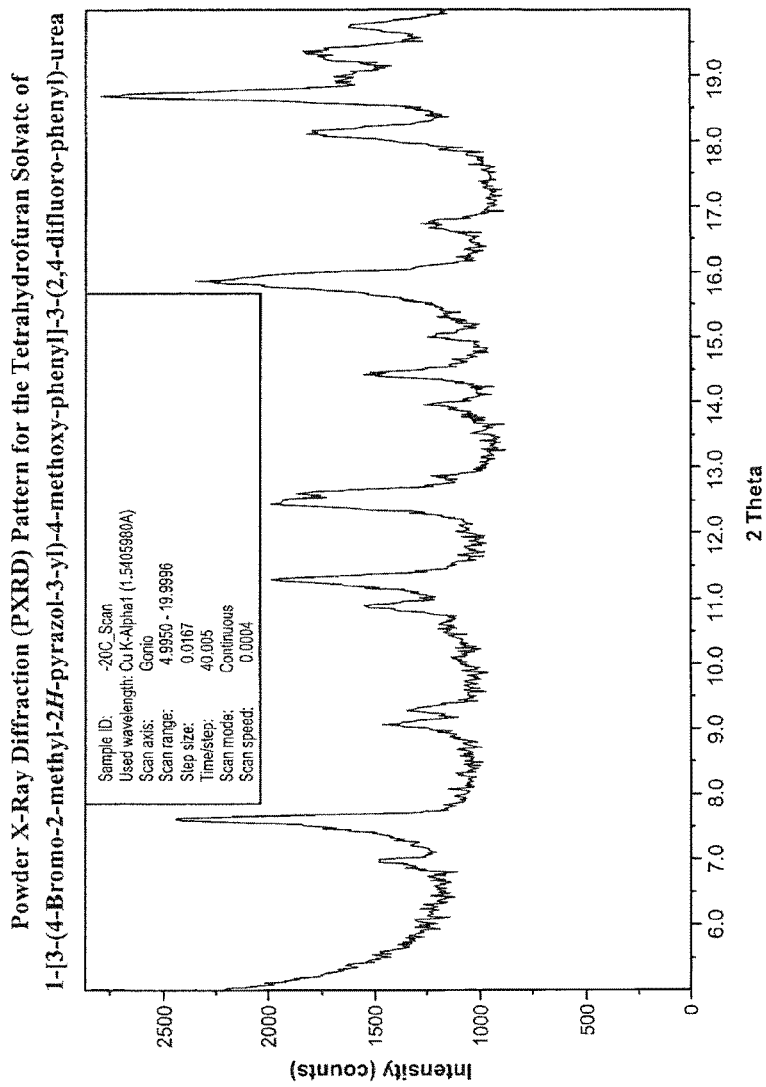
FIG. 29 depicts a powder X-ray diffraction (PXRD) pattern for a tetrahydrofuran solvate of 1-[3-(4-bromo-2-methyl-2H-pyrazol-3-yl)-4-methoxy-phenyl]-3-(2,4-difluoro-phenyl)-urea, which was recorded using a PANalytical X'Pert Plus Powder X-Ray Diffractometer in the 2θ geometry; scanning angles 5.0°-40.0°2θ.
Figure 30:
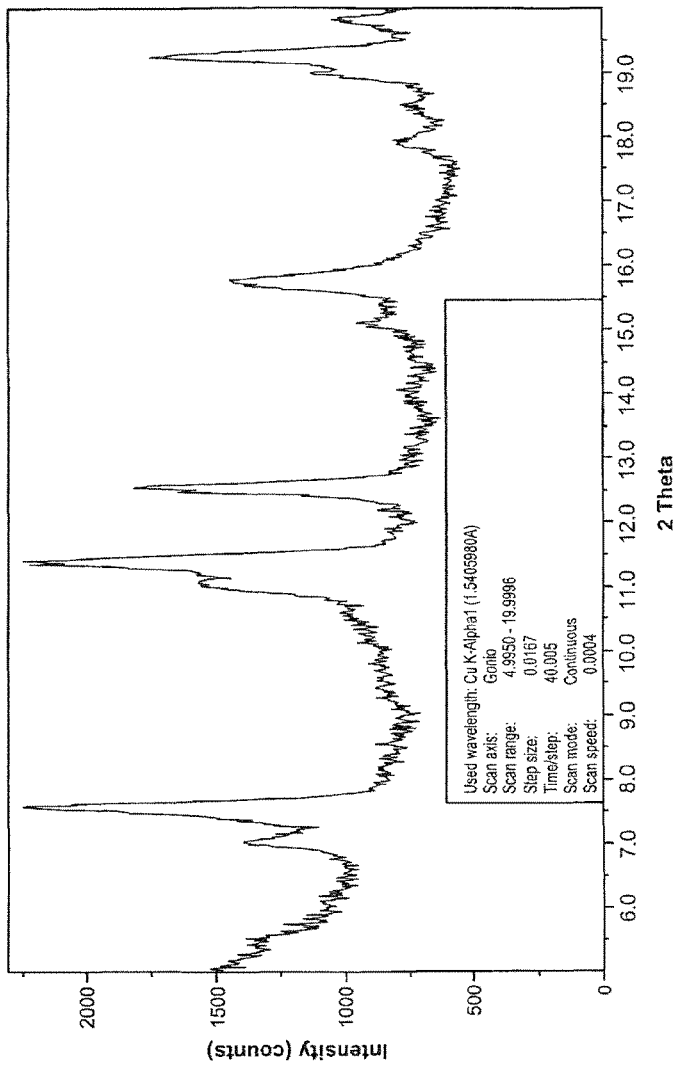
FIG. 30 depicts a powder X-ray diffraction (PXRD) pattern for a Heptane Solvate of 1-[3-(4-bromo-2-methyl-2H-pyrazol-3-yl)-4-methoxy-phenyl]-3-(2,4-difluoro-phenyl)-urea, which was recorded using a PANalytical X'Pert Plus Powder X-Ray Diffractometer in the theta/theta geometry; scanning angles 5.0°-40.0°2θ.

It is understood that the mixture obtained by the addition of heptane comprises at least a tetrahydrofuran solvate or a heptane solvate or a mixture of these two solvates. In addition, there may be other solvates that are present in the mixture that have not been identified. The tetrahydrofuran solvate and the heptane solvate have been identified. The powder X-ray diffraction (PXRD) pattern for the tetrahydrofuran solvate of 1-[3-(4-bromo-2-methyl-2H-pyrazol-3-yl)-4-methoxy-phenyl]-3-(2,4-difluoro-phenyl)-urea is shown in FIG. 29. The powder X-ray diffraction (PXRD) pattern for the heptane solvate of 1-[3-(4-bromo-2-methyl-2H-pyrazol-3-yl)-4-methoxy-phenyl]-3-(2,4-difluoro-phenyl)-urea is shown in FIG. 30.

In some embodiments, the first solvate is a tetrahydrofuran solvate.

In some embodiments, the first solvate is a heptane solvate.

In some embodiments, adding the aliphatic solvent to the solution to form a mixture comprising a first solvate of 1-[3-(4-bromo-2-methyl-2H-pyrazol-3-yl)-4-methoxy-phenyl]-3-(2,4-difluoro-phenyl)-urea is conducted at a temperature of about −35° C. to about 10° C.

In some embodiments, adding the aliphatic solvent to the solution to form a mixture comprising a first solvate of 1-[3-(4-bromo-2-methyl-2H-pyrazol-3-yl)-4-methoxy-phenyl]-3-(2,4-difluoro-phenyl)-urea is conducted at a temperature of about −25° C. to about −5° C.

In some embodiments, isolating the first solvate of 1-[3-(4-bromo-2-methyl-2H-pyrazol-3-yl)-4-methoxy-phenyl]-3-(2,4-difluoro-phenyl)-urea from the mixture is conducted by filtration to provide the isolated first solvate of 1-[3-(4-bromo-2-methyl-2H-pyrazol-3-yl)-4-methoxy-phenyl]-3-(2,4-difluoro-phenyl)-urea.

In some embodiments, washing the isolated first solvate of 1-[3-(4-bromo-2-methyl-2H-pyrazol-3-yl)-4-methoxy-phenyl]-3-(2,4-difluoro-phenyl)-urea with acetonitrile is conducted at a temperature of about −20° C. to about 10° C. to form a second solvate of 1-[3-(4-bromo-2-methyl-2H-pyrazol-3-yl)-4-methoxy-phenyl]-3-(2,4-difluoro-phenyl)-urea. In some embodiments, washing the isolated first solvate of 1-[3-(4-bromo-2-methyl-2H-pyrazol-3-yl)-4- methoxy-phenyl]-3-(2,4-difluoro-phenyl)-urea with acetonitrile is conducted at a temperature of about −10° C. to about 10° C. to form a second solvate of 1-[3-(4-bromo-2-methyl-2H-pyrazol-3-yl)-4-methoxy-phenyl]-3-(2,4-difluoro-phenyl)-urea. In some embodiments, washing the isolated first solvate of 1-[3-(4-bromo-2-methyl-2H-pyrazol-3-yl)-4-methoxy-phenyl]-3-(2,4-difluoro-phenyl)-urea with acetonitrile is conducted at a temperature of about −5° C. to about 5° C. to form a second solvate of 1-[3-(4-bromo-2-methyl-2H-pyrazol-3-yl)-4-methoxy-phenyl]-3-(2,4-difluoro-phenyl)-urea.

In some embodiments, the second solvate is an acetonitrile solvate of 1-[3-(4-bromo-2-methyl-2H-pyrazol-3-yl)-4-methoxy-phenyl]-3-(2,4-difluoro-phenyl)-urea. Additional information for converting the acetonitrile solvate to Form I of 1-[3-(4-bromo-2-methyl-2H-pyrazol-3-yl)-4-methoxy-phenyl]-3-(2,4-difluoro-phenyl)-urea has been described supra, also see the Examples infra.

In some embodiments, the acetonitrile solvate of 1-[3-(4-bromo-2-methyl-2H-pyrazol-3-yl)-4-methoxy-phenyl]-3-(2,4-difluoro-phenyl)-urea has a molecular ratio of acetonitrile to 1-[3-(4-bromo-2-methyl-2H-pyrazol-3-yl)-4-methoxy-phenyl]-3-(2,4-difluoro-phenyl)-urea of about 1:2.

In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted under reduced pressure. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a reduced pressure of about 100 mm Hg or less. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a reduced pressure of about 35 mm Hg or less. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a reduced pressure of about 10 mm Hg or less. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a reduced pressure of about 5 mm Hg or less. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted during at least two time periods, wherein the conversion is conducted at a first temperature during a first time period and wherein the conversion is conducted at a second temperature during a second time period, and wherein the first temperature is not equivalent to the second temperature.

In some embodiments, the second temperature is higher than the first temperature.

In some embodiments, the first temperature is at about 0° C. to about 45° C. In some embodiments, the first temperature is at about 15° C. to about 40° C. In some embodiments, the first temperature is at about 20° C. to about 30° C.

In some embodiments, the second temperature is about 45° C. to about 90° C. In some embodiments, the second temperature is about 60° C. to about 80° C. In some embodiments, the second temperature is about 65° C. to about 75° C.

In some embodiments, the first temperature is at about 20° C. to about 30° C. and the second temperature is about 65° C. to about 75° C.

In some embodiments the process further comprises the step of maintaining the first temperature until a loss on drying (LOD) for a representative sample from the process is at a level of about 30% or less. In some embodiments the process further comprises the step of maintaining the first temperature until a loss on drying (LOD) for a representative sample from the process is at a level of about 20% or less. In some embodiments the process further comprises the step of maintaining the first temperature until a loss on drying (LOD) for a representative sample from the process is at a level of about 15% or less. In some embodiments the process further comprises the step of maintaining the first temperature until a loss on drying (LOD) for a representative sample from the process is at a level of about 10% or less.

In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a first temperature of about 0° C. to about 45° C. until a loss on drying (LOD) for a representative sample from the process is at a level of about 30% or less and thereafter raising to a second temperature of about 45° C. to about 90° C. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a first temperature of about 15° C. to about 40° C. until a loss on drying (LOD) for a representative sample from the process is at a level of about 20% or less and thereafter raising to a second temperature about 60° C. to about 80° C. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a first temperature of about 20° C. to about 30° C. until a loss on drying (LOD) for a representative sample from the process is at a level of about 15% or less and thereafter raising to a second temperature of about 60° C. to about 80° C. In some embodiments, converting the second solvate to provide Form I of 1-[3-(4-bromo-2-methyl-2H-pyrazol-3-yl)-4-methoxy-phenyl]-3-(2,4-difluoro-phenyl)-urea is conducted at a first temperature of about 20° C. to about 30° C. until a loss on drying (LOD) for a representative sample from the process is at a level of about 10% or less and thereafter raising to a second temperature of about 65° C. to about 75° C.

In some embodiments, converting the acetonitrile solvate of 1-[3-(4-bromo-2-methyl-2H-pyrazol-3-yl)-4-methoxy-phenyl]-3-(2,4-difluoro-phenyl)-urea is conducted at a reduced pressure of about 35 mm Hg or less at a first temperature of about 20° C. to about 30° C. until a loss on drying (LOD) for a representative sample from the process is at a level of about 10% or less; and thereafter raising the first temperature to a second temperature of about 65° C. to about 75° C. while maintaining the reduced pressure of about 35 mm Hg or less.

7. Compositions and Processes of Preparing Compositions Comprising 1-[3-(4-bromo-2-methyl-2H-pyrazol-3-yl)-4-methoxy-phenyl]-3-(2,4-difluoro-phenyl)-urea One aspect of the present invention relates to compositions comprising Form I of 1-[3-(4-bromo-2-methyl-2H-pyrazol-3-yl)-4-methoxy-phenyl]-3-(2,4-difluoro-phenyl)-urea prepared according to any of the processes described herein, wherein the composition comprises less than 0.9 mole % of 1-(2,4-difluorophenyl)-3-(4-methoxy-3-(1-methyl-1H-pyrazol-5-yl)phenyl)urea.

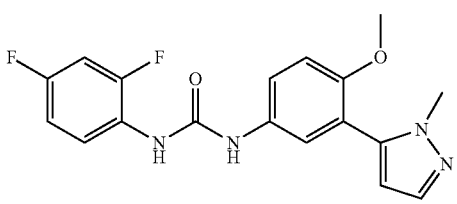 [SMILES: COc1ccc(NC(=O)Nc2ccc(F)cc2F)cc1-c1ccnn1C]

1-(2,4-difluorophenyl)-3-(4-methoxy-3-(1-methyl-1H-pyrazol-5-yl)phenyl)urea

Another aspect of the present invention relates to processes for preparing a pharmaceutical composition comprising admixing:

a composition comprising Form I of 1-[3-(4-bromo-2-methyl-2H-pyrazol-3-yl)-4-methoxy-phenyl]-3-(2,4-difluoro-phenyl)-urea prepared according to any one of the processes described herein, wherein the composition comprises less than 0.9 mole % of 1-(2,4-difluorophenyl)-3-(4-methoxy-3-(1-methyl-1H-pyrazol-5-yl)phenyl)urea; and a pharmaceutically acceptable carrier.

In some embodiments, compositions comprising Form I of 1-[3-(4-bromo-2-methyl-2H-pyrazol-3-yl)-4-methoxy-phenyl]-3-(2,4-difluoro-phenyl)-urea contain less than 0.8 mole % of 1-(2,4-difluorophenyl)-3-(4-methoxy-3-(1-methyl-1H-pyrazol-5-yl)phenyl)urea. In some embodiments, compositions contain less than 0.7 mole % of 1-(2,4-difluorophenyl)-3-(4-methoxy-3-(1-methyl-1H-pyrazol-5-yl)phenyl)urea. In some embodiments, compositions contain less than 0.6 mole % of 1-(2,4-difluorophenyl)-3-(4-methoxy-3-(1-methyl-1H-pyrazol-5-yl)phenyl)urea. In some embodiments, compositions contain less than 0.5 mole % of 1-(2,4-difluorophenyl)-3-(4-methoxy-3-(1-methyl-1H-pyrazol-5-yl)phenyl)urea. In some embodiments, compositions contain less than 0.4 mole % of 1-(2,4-difluorophenyl)-3-(4-methoxy-3-(1-methyl-1H-pyrazol-5-yl)phenyl)urea. In some embodiments, compositions contain less than 0.3 mole % of 1-(2,4-difluorophenyl)-3-(4-methoxy-3-(1-methyl-1H-pyrazol-5-yl)phenyl)urea. In some embodiments, compositions contain less than 0.2 mole % of 1-(2,4-difluorophenyl)-3-(4-methoxy-3-(1-methyl-1H-pyrazol-5-yl)phenyl)urea. In some embodiments, compositions contain less than 0.1 mole % of 1-(2,4-difluorophenyl)-3-(4-methoxy-3-(1-methyl-1H-pyrazol-5-yl)phenyl)urea.

Any suitable method can be used to determine the mol % of 1-(2,4-difluorophenyl)-3-(4-methoxy-3-(1-methyl-1H-pyrazol-5-yl)phenyl)urea, for example, $^1$H NMR, HPLC, and the like. The HPLC method described above along with the relative response factor (or by running standard concentration curves) is particularly useful for determining the mol % of 1-(2,4-difluorophenyl)-3-(4-methoxy-3-(1-methyl-1H-pyrazol-5-yl)phenyl)urea.

Another aspect of the present invention relates to processes for preparing a pharmaceutical composition comprising admixing:

a composition comprising 1-[3-(4-bromo-2-methyl-2H-pyrazol-3-yl)-4-methoxy-phenyl]-3-(2,4-difluoro-phenyl)-urea prepared according to any of the processes described herein, wherein the composition comprises less than 0.9 mole % of 1-(2,4-difluorophenyl)-3-(4-methoxy-3-(1-methyl-1H-pyrazol-5-yl)phenyl)urea; and a pharmaceutically acceptable carrier.

Another aspect of the present invention relates to compositions comprising an acetonitrile solvate of 1-[3-(4-bromo-2-methyl-2H-pyrazol-3-yl)-4-methoxy-phenyl]-3-(2,4-difluoro-phenyl)-urea prepared according to any of the processes described herein.

In some embodiments, the acetonitrile solvate of 1-[3-(4-bromo-2-methyl-2H-pyrazol-3-yl)-4-methoxy-phenyl]-3-(2,4-difluoro-phenyl)-urea has a molecular ratio of acetonitrile to 1-[3-(4-bromo-2-methyl-2H-pyrazol-3-yl)-4-methoxy-phenyl]-3-(2,4-difluoro-phenyl)-urea of about 1:2.

Another aspect of the present invention relates to compositions comprising an acetonitrile solvate of 1-[3-(4-bromo-2-methyl-2H-pyrazol-3-yl)-4-methoxy-phenyl]-3-(2,4-difluoro-phenyl)-urea. In some embodiments, the acetonitrile solvate of 1-[3-(4-bromo-2-methyl-2H-pyrazol-3-yl)-4-methoxy-phenyl]-3-(2,4-difluoro-phenyl)-urea has a molecular ratio of acetonitrile to 1-[3-(4-bromo-2-methyl-2H-pyrazol-3-yl)-4-methoxy-phenyl]-3-(2,4-difluoro-phenyl)-urea of about 1:2.

Pharmaceutical compositions may be prepared by any suitable method, typically by uniformly mixing Form I of 1-[3-(4-bromo-2-methyl-2H-pyrazol-3-yl)-4-methoxy-phenyl]-3-(2,4-difluoro-phenyl)-urea with liquids or finely divided solid carriers, or both, in the required proportions, and then, if necessary, forming the resulting mixture into a desired shape.

Accordingly, another aspect of the present invention provide processes for preparing pharmaceutical compositions comprising admixing Form I of 1-[3-(4-bromo-2-methyl-2H-pyrazol-3-yl)-4-methoxy-phenyl]-3-(2,4-difluoro-phenyl)-urea prepared by any of the methods described herein, and a pharmaceutically acceptable carrier.

Conventional excipients, such as binding agents, fillers, acceptable wetting agents, tableting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of a dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

Form I of 1-[3-(4-bromo-2-methyl-2H-pyrazol-3-yl)-4-methoxy-phenyl]-3-(2,4-difluoro-phenyl)-urea (Form I hereafter) of the present invention can be formulated into pharmaceutical compositions using techniques well known to those in the art and as described herein. Suitable pharmaceutically-acceptable carriers, outside those mentioned herein, are known in the art; for example, see Remington, *The Science and Practice of Pharmacy*, 20$^{th}$ Ed., 2000, Lippincott Williams & Wilkins, (Editors: Gennaro, A. R., et al.).

While it is possible that Form I of 1-[3-(4-bromo-2-methyl-2H-pyrazol-3-yl)-4-methoxy-phenyl]-3-(2,4-difluoro-phenyl)-urea (i.e., active ingredient) as described herein may, in an alternative use, be administered as a raw or pure chemical, it is preferable however to present the active ingredient as a pharmaceutical formulation or composition further comprising a pharmaceutically acceptable carrier. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The Form I of the present invention, together with a conventional adjuvant, carrier, or diluent, may be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient may also be administered by injection as a composition wherein, for example, saline, dextrose or water may be used as a suitable pharmaceutically acceptable carrier.

The dose when using the compounds of the present invention can vary within wide limits, as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to Form I of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or caregiver it may be necessary to deviate upward or downward from the doses described herein.

The amount of Form I of the present invention, required for use in treatment will vary with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, whether the disease state is chronic or acute, whether treatment or prophylaxis is conducted, or on whether further active compounds are administered in addition to Form I of the present invention and as part of a drug combination. The dosage regimen for treating a disease condition with Form I of the present invention and/or compositions of this invention is selected in accordance with a variety of factors as cited above. Thus, the actual dosage regimen employed may vary widely and therefore may deviate from a preferred dosage regimen and one skilled in the art will recognize that dosages and dosage regimens outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

Form I of the present invention can be administered in a wide variety of oral and parenteral dosage forms.

For preparing pharmaceutical compositions of Form I of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may contain from 0.5 to about 90 percent of Form I of the present invention; however, an artisan of ordinary skill would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as solvents or suspending media. For this purpose, any bland fixed oil may be employed including synthetic mono- or diglycerides. In addition, fatty acids such as oleic acid find use in the preparation of injectables.

Form I of the present invention, may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis, Form I of the present invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will generally also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. Administration to the respiratory tract include, for example, nasal aerosols or by inhalation, this can be carried out, for example, by using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the active ingredient in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example, carbon dioxide, CFCs, such as, dichlorodifluoromethane, trichlorofluoromethane, and dichlorotetrafluoroethane, HFAs, such as, 1,1,1,2,3,3,3-heptaflurorpropane and 1,1,1,2-tetrafluoroethane, and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively, the active ingredients may be provided in the form of a dry powder, for example, a powder mix of the compound in a suitable powder base such as lactose, starch, starch derivatives such as hydroxypropylmethylcellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Some embodiments of the present invention include a method of producing a pharmaceutical composition for "combination-therapy" comprising admixing at least one compound or crystalline form thereof as disclosed herein, together with at least one known pharmaceutical agent as described herein and a pharmaceutically acceptable carrier.

It is noted that when the serotonin 5-HT$_{2A}$-receptor modulators are utilized as active ingredients in a pharmaceutical composition, these are not intended for use only in humans, but in other non-human mammals as well. Indeed, recent advances in the area of animal health-care suggest that consideration be given for the use of active agents, such as serotonin 5-HT$_{2A}$-receptor modulators, for the treatment of an serotonin 5-HT$_{2A}$-receptor associated disease or disorder in companion animals (e.g., cats and dogs) and in livestock animals (e.g., such as cows, chickens, fish, etc). Those of ordinary skill in the art are readily credited with understanding the utility of such compounds in such settings.

The formulations prepared by the methods described herein are useful for the synthesis of any disease or condition for which the administration of a serotonin 5-HT$_{2A}$-receptor modulator is indicated.

Pharmacodynamic Effects of the Selective 5-HT$_{2A}$ Inverse Agonist 1-[3-(4-Bromo-2-methyl-2H-pyrazol-3-yl)-4-methoxy-phenyl]-3-(2,4-difluoro-phenyl)-urea (APD125) in Healthy Adults APD125, a potent and selective 5-HT$_{2A}$ serotonin receptor inverse agonist is a member of the genus disclosed in the European Patent EP1558582. In Phase 1 trials, APD125 showed vigilance-lowering effects on waking EEG, with maximal effects at 40-80 mg; peak effects were observed at 2-4 h after dosing. In the afternoon nap model of insomnia in normal volunteers, APD125 increased slow wave sleep and associated parameters in a dose-dependent manner, primarily during the early part of sleep. These effects occurred at the expense of REM sleep. Sleep onset latency was not decreased by APD125. In the afternoon nap model, APD125 decreased microarousals, the number of sleep stage shifts and number of awakenings after sleep onset.

In a Phase 2 trial, when compared to placebo, patients treated with APD125 experienced statistically significant improvements in measurements of sleep maintenance, or the ability to maintain sleep during the night after falling asleep. The improvements in measurements of sleep maintenance were achieved without any limiting next day cognitive effects. The data from the APD125 Phase 2 study are consistent with Phase 1 data and support further development of APD125 for the treatment of insomnia patients who have difficulty maintaining sleep.

In conclusion, APD125, a 5-HT$_{2A}$ serotonin receptor inverse agonist, improved parameters of sleep consolidation and maintenance in humans.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1: Pharmacokinetic Experiments

General Experimental Descriptions:

Male cynomolgus monkeys were administered an oral dose of APD125 in combination with excipients delivered as either a liquid in SGC (composition: 10 mg APD125 in Cremophor®:Labrasol® [1:1]), as wet-granulated tablets (see Example 2) or as dry-granulated tablets (see Example 7). APD125 dose levels were 10 mg, 30 mg, or 40 mg and the monkeys received approximately 10 mL of tap water after dose administration. Animals were fasted prior to dosing. Three to six monkeys were dosed per treatment group. In two cases, a 2×6 crossover study design was employed. Blood samples were collected via venous puncture at pre-dose (t=0) and 0.25 h, 0.5 h, 1 h, 2 h, 4 h, 6 h, 8 h, 12 h, 24 h and 48 h post-dose. Blood was treated with an anticoagulant and plasma was separated by centrifugation. Plasma samples were frozen and stored at or below −20° C. prior to analysis.

Pharmacokinetic Data Analysis:

Noncompartmental PK analysis was performed with a commercial software package (WinNonlin® Professional, version 5.2., Pharsight, Mountain View, Calif.; Computer System Validation report CSV-004-SM-R1), with calculation of the following parameters:

| Parameter | Definition |
|---|---|
| $t_{max}$ | Time of maximum observed plasma concentration |
| $C_{max}$ | Plasma concentration corresponding to $t_{max}$ |
| $AUC_{0-\infty}$ | Area under the plasma concentration versus time curve from the time of dosing to extrapolated to infinity |

Bioanalytical Method:

Anticoagulated male cynomolgus monkey plasma samples were analyzed for APD125 and the internal standard using a selective liquid chromatography-tandem mass spectrometry (LC/MS/MS) method. Plasma proteins were removed with the addition of acetonitrile at two-fold the tissue volume, followed by centrifugation. The supernatant was injected onto an HPLC system equipped with a SCIEX API 3000 mass spectrometer. Peak areas were measured against the internal standard in the positive ion MRM mode. Quantitation was performed with regression analyses of the external calibration standards.

Example 1.1: Preliminary Wet Granulation-Based Tablet Formulation: Monkey APD125 Plasma Exposure Monkey APD125 plasma exposure after oral administration of SGCs or wet granulation tablets are shown in FIG. 1. PK parameters are presented in Table 1. APD125 absorption into the systemic circulation occurred over a 2-h to 4-h period followed by a mono-exponential terminal phase. The time to maximal plasma concentration (tax) was most rapid for the liquid filled SGCs at 2 h. The $t_{max}$ increased with tablet administration to 2.7 h and 4 h, for APD125 Form II and APD125 Form I, respectively. The SGC $C_{max}$ (0.953 µg/mL±0.180 µg/mL; dose adjusted to 30 mg) was 19-fold and 2-fold greater than the $C_{max}$ for APD125 Form II (0.051 µg/mL±0.007 µg/mL) and APD125 Form I (0.504 µg/mL±0.109 µg/mL). The integrated plasma exposures ($AUC_{0-\infty}$) were highest for SGC (4.540 h·µg/mL±1.394 h·µg/mL; dose adjusted to 30 mg) and APD125 Form I tablets (4.998 h·µg/mL±1.739 h·µg/mL). APD125 Form II tablet exposure (0.727 h·µg/mL±0.362 h·µg/mL) was at least 6-fold lower compared to SGC and APD125 Form I tablets.

TABLE 1

| Formulation | Dose (mg) | N | Cmax (µg/mL) Mean | SD | $AUC_{0-\infty}$ (h · µg/mL) Mean | SD |
|---|---|---|---|---|---|---|
| APD125 Form I:PVP (1:8) | 10 | 6 | 0.227 | 0.153 | 1.507 | 1.218 |
| APD125 Form I:PVP (1:8) | 30 | 3 | 0.504 | 0.109 | 4.998 | 1.739 |
| APD125 Form II:PVP (1:8) | 30 | 3 | 0.051 | 0.007 | 0.727 | 0.362 |
| SGC: | 10 | 6 | 0.942 | 0.303 | 3.192 | 1.291 |
| APD125 in [1:1] | 30[a] | 2 | 0.953 | 0.180 | 4.540 | 1.394 |
| Cremophor ®:Labrasol ® | 40 | 2 | 1.270 | 0.240 | 6.054 | 1.859 |

[a]40-mg SGC dose adjusted to 30 mg for comparison purposes.

Figure 2:
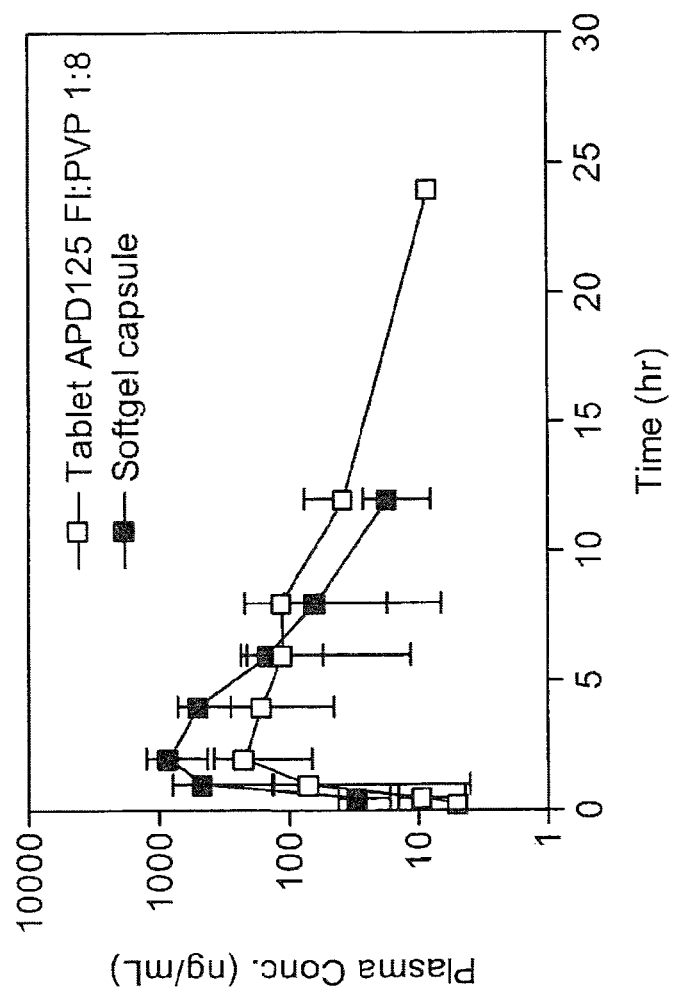
FIG. 2 depicts APD125 plasma exposure in monkeys after oral administration of wet-granulation tablets (composition: 10 mg APD125 Form I:PVP [1:8]) or SGC (composition: 10 mg APD125 in Cremophor®:Labrasol® [1:1]).
Figure 3:
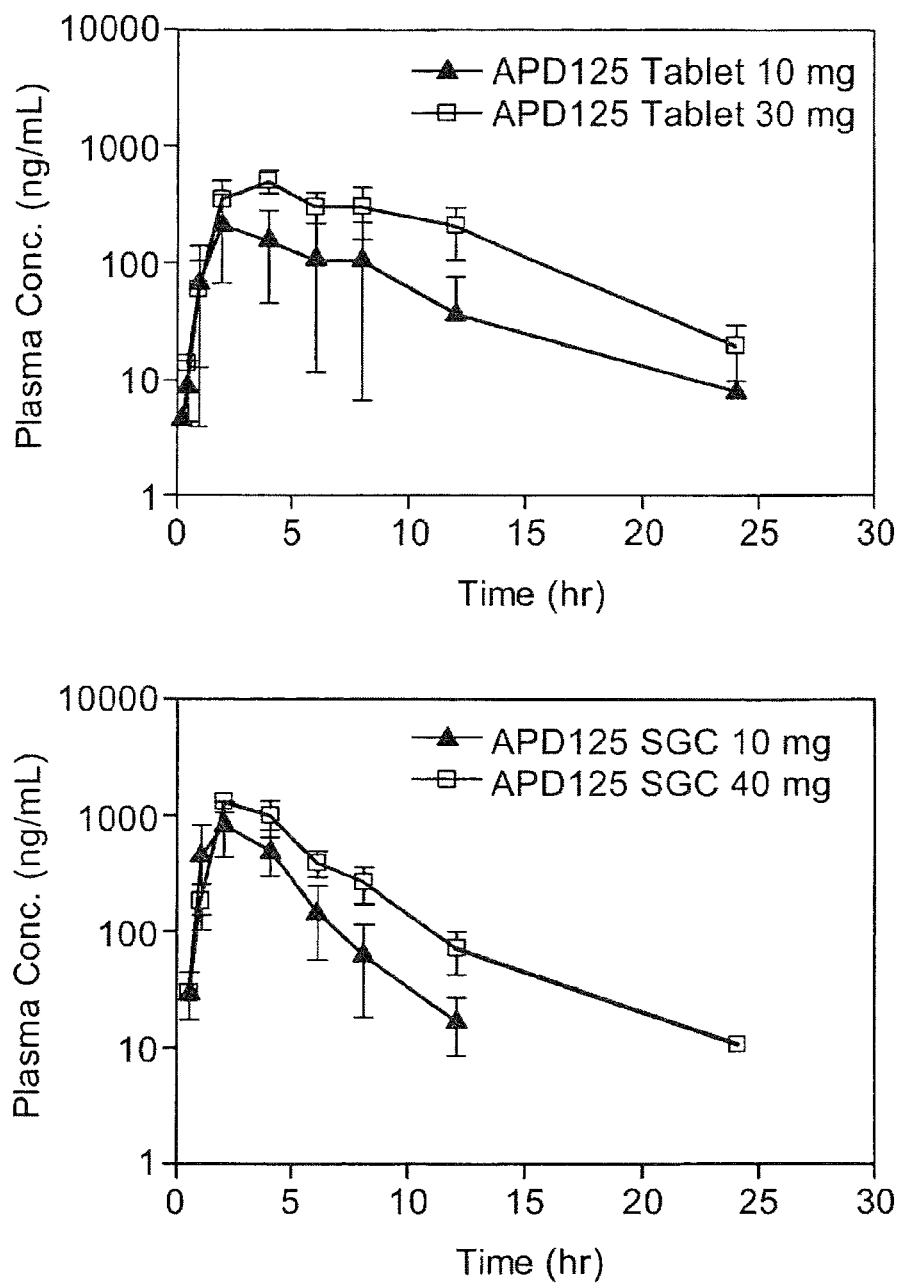
FIG. 3: depicts monkey PK exposure results for 10-mg and 30-mg APD125 Form I wet-granulation tablets versus 10-mg and 40-mg SGCs.

APD125 Form II-based tablets exhibited poor exposure ($C_{max}$ and $AUC_{0-\infty}$) relative to SGCs and therefore, were removed from further consideration. In contrast, APD125 Form I-based tablets exhibited similar integrated exposures ($AUC_{0-\infty}$) to SGCs, with approximately half the $C_{max}$ of the SGCs, a not uncommon finding when comparing liquid and solid-based formulations. It should be noted, however, that at a lower dose there was disparity between all exposure parameters. At a 10-mg dose, SGC $C_{max}$ and $AUC_{0-\infty}$ values were four-fold and two-fold higher, respectively, compared to the wet granulation tablet exposure parameters suggesting tablets and SGC become dissimilar with decreasing dose (FIG. 2, FIG. 3, Table 2).

TABLE 2

| Formulation | Dose (mg) | Cmax (µg/mL) Mean | SD | $AUC_{0-\infty}$ (h · µg/mL) Mean | SD |
|---|---|---|---|---|---|
| Form I tablet | 10 | 0.227 | 0.153 | 1.507 | 1.218 |
|  | 30 | 0.504 | 0.109 | 4.998 | 1.739 |
| SGC | 10 | 0.942 | 0.303 | 3.192 | 1.291 |
|  | 40 | 1.270 | 0.240 | 6.054 | 1.859 |

Example 2: Wet-Granulation Tablet

Example 2.1: Tablet Manufacturing

Using a 1-L bowl of high-shear granulator, PVP, APD125, mannitol, methyl cellulose, half of the xPVP, and half of the SLS were added to the key high shear granulator. The resulting mixture was dry-mixed for 5 minutes with impeller and chopper running. After which, water was added slowly using a transfer pipette through the addition port on the lid of the granulator bowl, while the impeller and chopper were still running. The process was stopped once power consumption started to rise quickly. The lid was then opened, and the granulation visually and texturally inspected to ensure proper moisture content had been achieved. The wet granulation was spread evenly over tray paper and dried in an oven at 55° C., until a loss on drying (LOD) of less than 5% w/w was achieved. Next, the dried granulation was passed through a mill with round-hole screen size of 0.063". A 1-qt. blender was charged with this screened material, and the other half of the SLS and xPVP was added, followed by blending for 5 minutes. Finally, magnesium stearate was added and the mixture was blended for 1 minute. Tableting was performed as follows: For each tablet (30 mg), 600 mg final blend was dispensed onto weigh paper and filled into dies (0.730"×0.365"). The granulation was then pressed into tablets using a carver press to achieve a hardness of about 11 kp. General tablet composition is provided in Table 3.

TABLE 3

| Ingredient | % (w/w) |
|---|---|
| APD125 Form I or Form II (micronized)[a] | 5.0 |
| PVP K-29/32 | 40.0 |
| Mannitol powdered | 22.0 |
| xPVP | 30.0 |
| Methyl cellulose | 0.5 |
| SLS | 2.0 |
| Magnesium stearate | 0.5 |
| Total | 100.0 |

[a]For placebo APD125 was replaced with mannitol

Example 2.2: Stability Testing

Figure 4:
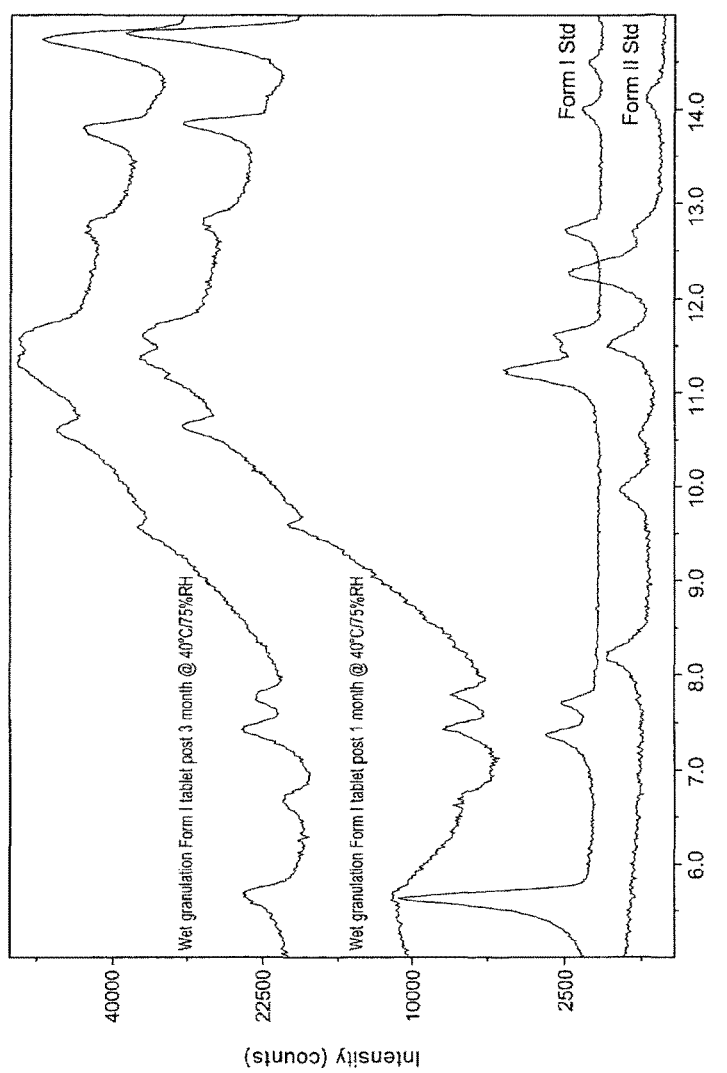
FIG. 4 depicts the 1-month and 3-month PXRD results for the wet-granulation Form I based tablet. The PXRD patterns show that the samples substantially comprise Form I at both time points.
Figure 5:
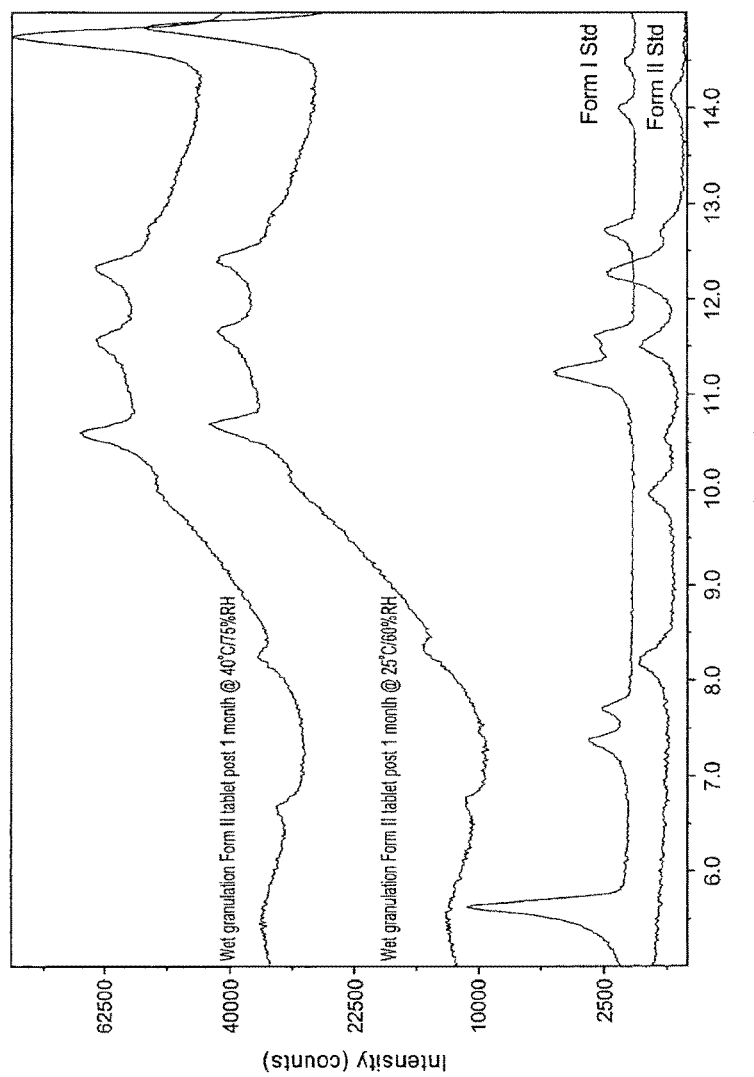
FIG. 5 depicts the 1-month and 3-month PXRD results for the wet-granulation Form II based tablet. The PXRD patterns show that the samples substantially comprise Form II at both time points.

Wet-granulation based placebo, 30-mg Form I, and 30-mg Form II tablets were placed on stability at 25° C./60% RH and 40° C./75% RH, using 60-mL HDPE bottles (non-induction sealed). Appearance, Assay, DFA, Dissolution, Water Content by Karl Fischer (except at Initial), Tablet Hardness, Related Substances, and Powder X-ray Diffraction (PXRD) testing were performed at initial (t=0), and at 1-month, 3-month and 6-month time points. Results for the wet-granulation Form I and Form II based tablets are provided in Table 4. Form I and Form II based tablet initial, 1-month, 3-month and 6-month dissolution results are provided in Table 5. Three-month and 6-month DFA results are provided in Table 6. Results of the water content determination by Karl Fischer at 1-month, 3-month and 6-month time points are provided in Table 7. Initial (t=0), 1-month, 3-month and 6-month tablet hardness results are provided in Table 8, while initial (t=0), 1-month, 3-month and 6-month PXRD results are provided in Table 9. PXRD results obtained at the 3-month time point are provided in FIG. 4 and FIG. 5.

TABLE 4

| | | % Assay (% RSD) n = 2 | | | |
|---|---|---|---|---|---|
| Formulation | Conditions | t = 0 | 1 month | 3 month | 6 month |
| Form I tablet | 25° C./ 60% RH | 100.3 (0.4) | 108.2 (2.4) | 101.8 (1.8) | 89.8 (0.2) |
| | 40° C./ 75% RH | | 106.9 (5.4) | 99.1 (0.5) | 84.3 (2.6) |

TABLE 4-continued

| | | % Assay (% RSD) n = 2 | | | |
|---|---|---|---|---|---|
| Formulation | Conditions | t = 0 | 1 month | 3 month | 6 month |
| Form II tablet | 25° C./ 60% RH | 97.7 (3.4) | 96.8 (0.1) | 101.3 (2.5) | 91.1 (2.3) |
| | 40° C./ 75% RH | | 96.9 (0.7) | 99.3 (1.2) | 84.3 (3.0) |

TABLE 5

| | | Dissolution % Released (% RSD) | | | |
|---|---|---|---|---|---|
| Formulation | Storage Conditions | 15 min | 30 min | 45 min | 60 min |
| Form I tablet | Initial | 68.3 (3.7) | 79.7 (0.8) | 81.6 (0.7) | 82.9 (0.4) |
| | 1 month at 25° C./60% RH | 73.9 (3.8) | 85.9 (0.2) | 88.4 (0.8) | 89.9 (0.6) |
| | 1 month at 40° C./75% RH | 70.3 (11.8) | 84.9 (3.1) | 88.1 (1.7) | 89.6 (1.8) |
| | 3 months at 25° C./60% RH | 76.8 (3.2) | 87.6 (1.1) | 90.2 (1.3) | 91.3 (1.3) |
| | 3 months at 40° C./75% RH | 71.1 (8.2) | 85.8 (0.8) | 89.1 (0.4) | 90.6 (0.7) |
| | 6 months at 25° C./60% RH | 77.0 (3.8) | 82.2 (0.7) | 86.1 (0.3) | 85.1 (1.5) |
| | 6 months at 40° C./75% RH | 65.7 (3.1) | 73.5 (1.2) | 74.4 (3.7) | 75.0 (2.7) |
| Form II tablet | Initial | 47.5 (4.9) | 55.9 (0.5) | 57.8 (0.7) | 58.4 (0.5) |
| | 1 month at 25° C./60% RH | 48.1 (12.5) | 58.3 (1.5) | 60.7 (1.3) | 61.8 (0.6) |
| | 1 month at 40° C./75% RH | 49.1 (5.9) | 57.5 (1.3) | 60.0 (1.0) | 61.0 (0.4) |
| | 3 months at 25° C./60% RH | 54.1 (4.5) | 60.4 (0.4) | 62.3 (0.3) | 63.4 (0.3) |
| | 3 months at 40° C./75% RH | 54.5 (2.9) | 59.8 (1.1) | 61.7 (0.7) | 63.8 (4.3) |
| | 6 months at 25° C./60% RH | 41.4 (3.3) | 48.1 (3.6) | 48.1 (1.1) | 48.0 (0.8) |
| | 6 months at 40° C./75% RH | 46.4 (0.0) | 48.7 (2.2) | 49.7 (0.8) | 50.9 (0.8) |

TABLE 6

| Formulation | DFA (ppm) post 3 months at 25°/ 60% RH n = 2 (rep1/rep2) | DFA (ppm) post 3 months at 40°/ 75% RH n = 2 (rep1/rep2) | DFA (ppm) 6 months at 25° C./ 60% RH n = 2 (rep1/rep2) | DFA (ppm) 6 months at 40° C./ 75% RH n = 2 (rep1/rep2) |
|---|---|---|---|---|
| Form I tablet | ND | 165/166 | <35 | 833/834 |
| Form II tablet | ND | 253/245 | <35 | 1400/1414 |
| SGC | 542 (est)[a] | 4387(est.)[a] | ND | ND |

[a]The 3-month SGC results estimated using three times mean 28 day data (APD125 5-mg and 40-mgSGC capsule results 189.3 ppm and 172.3 ppm at 25° C./60% RH, respectively, and 1658.2 ppm and 1266.5 ppm at 40° C./75% RH, respectively).
ND = not determined

TABLE 7

| | | % H$_2$O (rep1/rep2)[a] | | |
|---|---|---|---|---|
| Formulation | Storage Conditions | 1 month n = 1 | 3 months n = 2 | 6 months n = 2 |
| Placebo | 25° C./60% RH | 7.59 | 9.55/9.43 | 9.36/9.18 |
| | 40° C./75% RH | 8.96 | 10.50/10.53 | 10.51/11.15 |
| Form I tablet | 25° C./60% RH | 8.68 | 8.32/8.55 | 8.92/9.24 |
| | 40° C./75% RH | 9.56 | 10.05/9.82 | 11.93/12.04 |
| Form II tablet | 25° C./60% RH | 8.75 | 8.67/8.77 | 9.40/9.22 |
| | 40° C./75% RH | 8.86 | 10.91/10.69 | 13.35/13.46 |

[a]Water Content by Karl Fischer was not performed at t = 0

TABLE 8

| Condition | Material | Target Hardness (kp) t = 0 | Average Hardness and Range (kp) n = 4 | | |
|---|---|---|---|---|---|
| | | | 1 month | 3 months | 6 months |
| 25° C. 60% RH | Form I/PVP (1:8) Wet granulation | 11.0 | 7.2 (4.6-10.1) | 7.8 (3.9-10.1) | 4.8 (3.8-7.0) |
| | Form II/PVP (1:8) Wet granulation | 11.0 | 6.4 (4.5-9.4) | 7.8 (5.6-12.4) | 9.4 (8.2-12.1) |

TABLE 8-continued

| Condition | Material | Target Hardness (kp) t = 0 | Average Hardness and Range (kp) n = 4 | | |
|---|---|---|---|---|---|
| | | | 1 month | 3 months | 6 months |
| | Placebo | 10.0 | 12.9 (9.0-21.2) | 11.0 (7.7-14.4) | 11.5 (7.6-16.2) |
| 40° C. 75% RH | Form I/PVP (1:8) Wet granulation | 11.0 | 5.5 (3.5-7.3) | 5.9 (3.9-9.9) | 9.3 (7.8-11.1) |
| | Form II/PVP (1:8) Wet granulation | 11.0 | 7.6 (6.0-10.0) | 6.8 (4.3-8.0) | 22.2 (23.1-23.6) |
| | Placebo | 10.0 | 8.7 (7.4-10.6) | 9.9 (6.5-14.8) | 14.9 (12.6-13.5) |

TABLE 9

| | | APD125 Polymorphic Form(s) Detected | | | |
|---|---|---|---|---|---|
| Condition | Material | t = 0 | 1 month | 3 months | 6 months |
| 25° C. 60% RH | Form I/PVP (1:8) Wet granulation | Form I | Form I | Form I | Form I |
| | Form II/PVP (1:8) Wet granulation | Form II | Form II | Form II | —[b] |
| | Placebo | NA | NA | NA | NA |
| 40° C. 75% RH | Form I/PVP (1:8) Wet granulation | Form I | Form I | Form I | Form I[a] |
| | Form II/PVP (1:8) Wet granulation | Form II | Form II | Form II | —[b] |
| | Placebo | NA | NA | NA | NA |

[a]Some reduction in Form I peak intensity was observed, but no Form II was detected.
[b]PXRD measurements were not collected for the Form II tablets at 6 months. NA = not applicable The Form I and Form II based wet-granulation tablets exhibited similar chemical stability (Table 4), although it was not possible to accurately determine if a significant drop in assay was occurring for either tablet formulation, due, in part, to the significant assay variation observed. For example, both formulations showed near 100% assay at t=0, but the Form I tablets showed 106.9% assay and 108.2% assay at 1 month, at 40° C./75% RH and 25° C./60% RH, respectively. In addition, since water content determination was not added to the stability testing protocol until the 1-month time point, none of the assay results were corrected for water content. This is a significant point, since water contents increased from 9.56% w/w to 11.99% w/w at 40° C./75% RH for the Form I based tablets (Table 7). Therefore, assay results were only used to consider the relative stability of Form I and Form II based tablets. Chemical stability of the tablet, relative to SGCs, was evaluated on the basis of DFA formation rates. For both tablet formulations, low DFA formation rates (Table 6) were observed over the course of the R&D stability study, far superior to SGCs. Dissolution (Table 5) results showed no significant changes as a function of time, with Form II tablets exhibiting consistently slower dissolution relative to Form I tablets, in agreement with monkey plasma exposure results, supra. Tablet hardness measurements (Table 8), on the other hand, showed significant variability. However, since the tablets were hand pressed rather than pressed using automated equipment, the wet granulation based tablet R&D stability hardness results might not be indicative of long-term tablet hardness stability. Water content determination by Karl Fischer at 1-month and 3-months (Table 7) suggests a possible water uptake of about 3% w/w to about 5% w/w between 1 month and 6 months at 40° C./75% RH, suggesting some level of moisture control would be advisable for future tablet development. PXRD results (Table 9, FIG. 4 and FIG. 5) showed good solid-state form control, supporting the potential use of metastable Form I for further tablet development. However, the Form I tablet 6-month PXRD results at 40° C./75% RH showed some loss in Form I peak intensity. The water content of the Form I tablets at 6 months and 40° C./75% RH was 11.99% w/w (Table 7), as compared to 9.94% w/w water at 3 months and 40° C./75% RH and 9.08% w/w water at 6 months and 25° C./60% RH, both of which did not show a loss in Form I content, suggesting water contents of 12% w/w or higher might result in Form I content reduction. Therefore, these results suggest future Form I tablet development should focus upon dry rather than wet-based formulations, and efforts to minimize water uptake, such as utilizing a water barrier tablet coating, should be considered. In addition, the 0.5% w/w methyl cellulose loading used in the wet-granulation tablets was based upon Form I API stabilization results (see Example 5).

Example 3: Thermal Activity Monitoring MicroWatt Excipient Compatibility Screening Test Blend Preparation:

Materials for each of the nine formulations shown in Tables 10 through 18 were dispensed into separately labeled 60 mL glass jars and manually blended (tumbled) for about 5 min.

TABLE 10

Blend 1: APD125/PVP (1:8)

| Ingredient | % (w/w) | Amount (g) |
|---|---|---|
| APD125 | 5.0 | 0.50 |
| Mannitol (powdered) | 21.5 | 2.15 |
| PVP | 40.0 | 4.00 |
| xPVP | 30.0 | 3.00 |
| Methyl cellulose | 0.5 | 0.05 |
| SLS | 2.0 | 0.20 |
| Magnesium stearate | 1.0 | 0.10 |
| Total | 100.0 | 10.00 |

TABLE 11

Blend 2: APD125/PVP (1:5)

| Ingredient | % (w/w) | Amount (g) |
|---|---|---|
| APD125 | 5.0 | 0.50 |
| Mannitol (powdered) | 55.0 | 5.50 |
| PVP | 25.0 | 2.50 |
| xPVP | 12.0 | 1.20 |
| SLS | 2.0 | 0.20 |
| Magnesium stearate | 1.0 | 0.10 |
| Total | 100.0 | 10.00 |

TABLE 12

Blend 3: APD125/PVP (1:8) Dical phosphate/MCC

| Ingredient | % (w/w) | Amount (g) |
|---|---|---|
| APD125 | 5.0 | 0.50 |
| Dical phosphate | 20.0 | 2.00 |
| MCC | 20.0 | 2.00 |
| PVP | 40.0 | 4.00 |
| xPVP | 11.5 | 1.15 |
| Methyl cellulose | 0.5 | 0.05 |
| SLS | 2.0 | 0.20 |
| Magnesium stearate | 1.0 | 0.10 |
| Total | 100.0 | 10.00 |

TABLE 13

Blend 4: APD125/PVP (1:8) Mannitol/MCC

| Ingredient | % (w/w) | Amount (g) |
|---|---|---|
| APD125 | 5.0 | 0.50 |
| Mannitol (powdered) | 20.0 | 2.00 |
| MCC | 20.0 | 2.00 |
| PVP | 40.0 | 4.00 |
| xPVP | 11.5 | 1.15 |
| Methyl cellulose | 0.5 | 0.05 |
| SLS | 2.0 | 0.20 |
| Magnesium stearate | 1.0 | 0.10 |
| Total | 100.0 | 10.00 |

TABLE 14

Blend 5: APD125/coPVP (1:8)

| Ingredient | % (w/w) | Amount (g) |
|---|---|---|
| APD125 | 5.0 | 0.50 |
| Mannitol (powdered) | 21.5 | 2.15 |
| coPVP | 40.0 | 4.00 |
| xPVP | 30.0 | 3.00 |
| Methyl cellulose | 0.5 | 0.05 |
| SLS | 2.0 | 0.20 |
| Magnesium stearate | 1.0 | 0.10 |
| Total | 100.0 | 10.00 |

TABLE 15

Blend 6: APD125/coPVP (1:8) xCMC

| Ingredient | % (w/w) | Amount (g) |
|---|---|---|
| APD125 | 5.0 | 0.50 |
| Mannitol (powdered) | 21.5 | 2.15 |
| coPVP | 40.0 | 4.00 |
| xCMC | 30.0 | 3.00 |
| Methyl cellulose | 0.5 | 0.05 |
| SLS | 2.0 | 0.20 |
| Magnesium stearate | 1.0 | 0.10 |
| Total | 100.0 | 10.00 |

TABLE 16

Blend 7: APD125/PVP (1:8) Dical phosphate/MCC, xCMC

| Ingredient | % (w/w) | Amount (g) |
|---|---|---|
| APD125 | 5.0 | 0.50 |
| Dical phosphate | 20.0 | 2.00 |
| MCC | 20.0 | 2.00 |
| PVP | 40.0 | 4.00 |
| xCMC | 11.5 | 1.15 |
| Methyl cellulose | 0.5 | 0.05 |
| SLS | 2.0 | 0.20 |
| Magnesium stearate | 1.0 | 0.10 |
| Total | 100.0 | 10.00 |

TABLE 17

Blend 8: APD125/PVP (1:5) Dical phosphate/MCC without methyl cellulose

| Ingredient | % (w/w) | Amount (g) |
|---|---|---|
| APD125 | 5.0 | 0.50 |
| Dical phosphate | 27.5 | 2.75 |
| MCC | 27.5 | 2.75 |
| PVP | 25.0 | 2.50 |
| xPVP | 12.0 | 1.20 |
| SLS | 2.0 | 0.20 |
| Magnesium stearate | 1.0 | 0.10 |
| Total | 100.0 | 10.00 |

TABLE 18

Blend 9: APD125/PVP (1:8) Poloxamer

| Ingredient | % (w/w) | Amount (g) |
|---|---|---|
| APD125 | 5.0 | 0.50 |
| Mannitol (powdered) | 21.5 | 2.15 |
| PVP | 40.0 | 4.00 |
| xPVP | 30.0 | 3.00 |
| Methyl cellulose | 0.5 | 0.05 |
| Poloxamer | 2.0 | 0.20 |
| Magnesium stearate | 1.0 | 0.10 |
| Total | 100.0 | 10.00 |

Experimental Method

The formulation screening studies were performed at Aptuit Inc., Kansas City, Mo. 64137. Measurements were performed at 40° C. using a thermal activity monitoring (TAM) model 2277 consisting of four calorimetric units (2277-201) and standard amplifiers. All data were collected using Digitam® for Windows, version 4.1, software. Prior to initiating the series of experiments, each calorimeter unit was calibrated at 100 µW using a static electrical calibration procedure. Samples of APD125, APD125 formulation blend, or formulation blend placebo were weighed into separate 5-mL stainless steel ampoules. Approximately 100 mg of each material was used. The reference ampoules were loaded with approximately 150 mg of 4-mm borosilicate glass balls. Each ampoule was loaded onto an ampoule lifter and placed into the equilibrium position. After an initial pause, a baseline heat flow was recorded prior to lowering the samples into the measurement position. After sufficient data had been collected, the ampoules were returned to the equilibrium position and a final baseline heat flow was collected. The raw heat flow data were baseline corrected and exported for further data analysis.

Results:

The results for the nine APD125 formulation blends are provided in Table 19. The desired result is zero net heat flow, with results within about 2 µW/g of zero being indistinguishable from baseline noise. With these facts in mind, it can be seen that formulation blends 1, 4, 8 and 9 are the most compatible blends, while blend 7 is the least compatible.

TABLE 19

| Formulation Blend | Net Heat Flow Output (µW/g) |
| --- | --- |
| 1[a] | 0.87 |
| 2 | −13.63 |
| 3 | 8.88 |
| 4[a] | −0.23 |
| 5 | −13.10 |
| 6 | −8.92 |
| 7 | −62.36 |
| 8[a] | −0.78 |
| 9[a] | −1.19 |

[a]Most stable formulation blends

These results suggest that mannitol (diluent/filler), PVP (dispersing agent), xPVP (dispersing agent), methyl cellulose (APD125 Form I stabilizer), poloxamer (wetting agent), magnesium stearate (lubricant), dical phosphate (diluent/filler), MCC (diluent/filler) and SLS (wetting agent), the excipients used in one or more of the four most stable blends (i.e., blends 1, 4, 8 and 9), are suitable for further consideration as excipients. The remaining two excipients used in the study, xCMC and coPVP, were not in any of the most stable formulations, and therefore, should be considered to be potentially problematic.

Example 4: Effect of Milling and Compression Upon APD125 Form I

Sample Preparation:

Micronized APD125 Form I, was ground using a mortar and pestle, with samples withdrawn at 1-min, 5-min and 10-min time points for PXRD analyses to evaluate the impact of grinding upon the solid-state form of APD125 Form I. PXRD patterns were obtained pre- and post-milling. Additionally, micronized APD125 Form I, was compressed at 2 kp, 5 kp and 10 kp for 1 min per sample using a Carver press. The samples were then removed from the Carver press and lightly broken up using a mortar and pestle, prior to PXRD analysis to evaluate the impact of compression upon the solid-state form of APD125 Form I. PXRD patterns were obtained pre- and post-compression.

Powder X-ray Diffraction:

PXRD measurements were obtained using a Philips (PANalytical) X'Pert PRO theta/theta diffractometer (EQ 0233) equipped with an X'Celerator RTMS detector and utilizing copper Kα radiation, operating at 45 kV and 40 mA. The instrument radius was 239.5 mm, the mask filter was 20 mm, the soller slit was 0.04 radians, and a nickel filter and sample spinning were used during data acquisition. The application and instrument control software used were X'Pert Data Collector®, version 2.0c and XPERT-PRO®, version 1.6, respectively. The samples were scanned from 5° to 40°2θ in continuous mode, using a step size of 0.0167°2θ.

Figure 6:
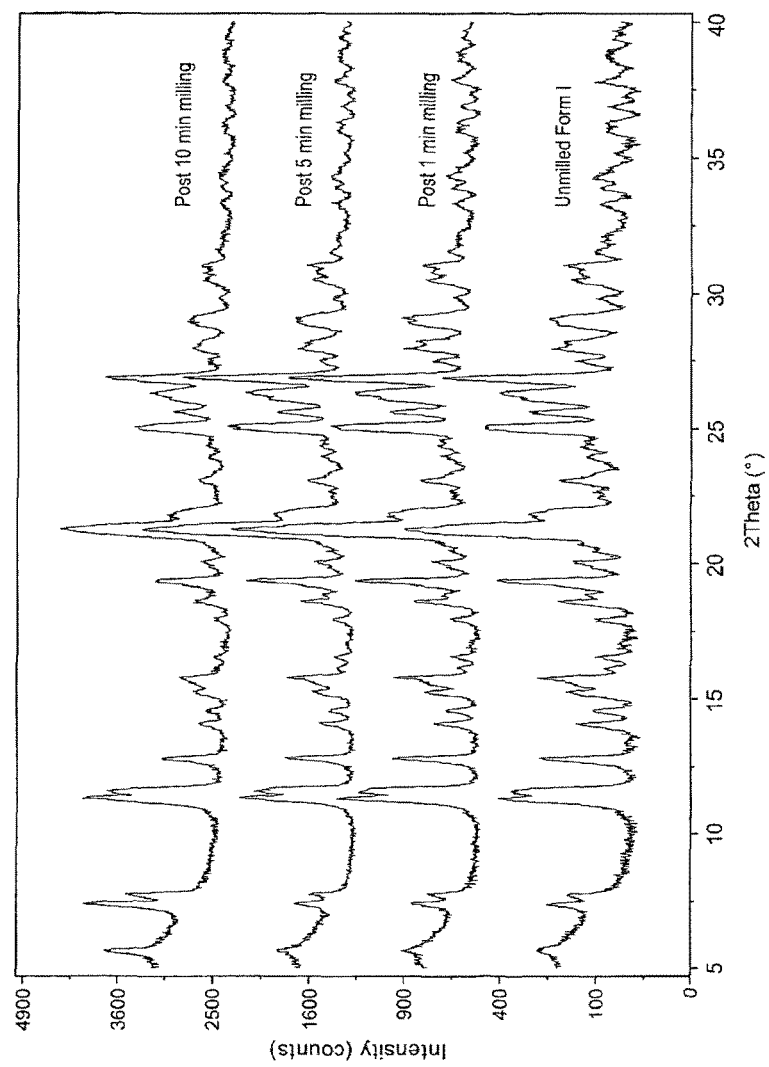
FIG. 6 depicts PXRD patterns for micronized APD125 Form I, before and after grinding with a mortar and pestle for 1 minute, 5 minutes and 10 minutes. The PXRD patterns show that the samples all substantially comprise Form I.
Figure 7:
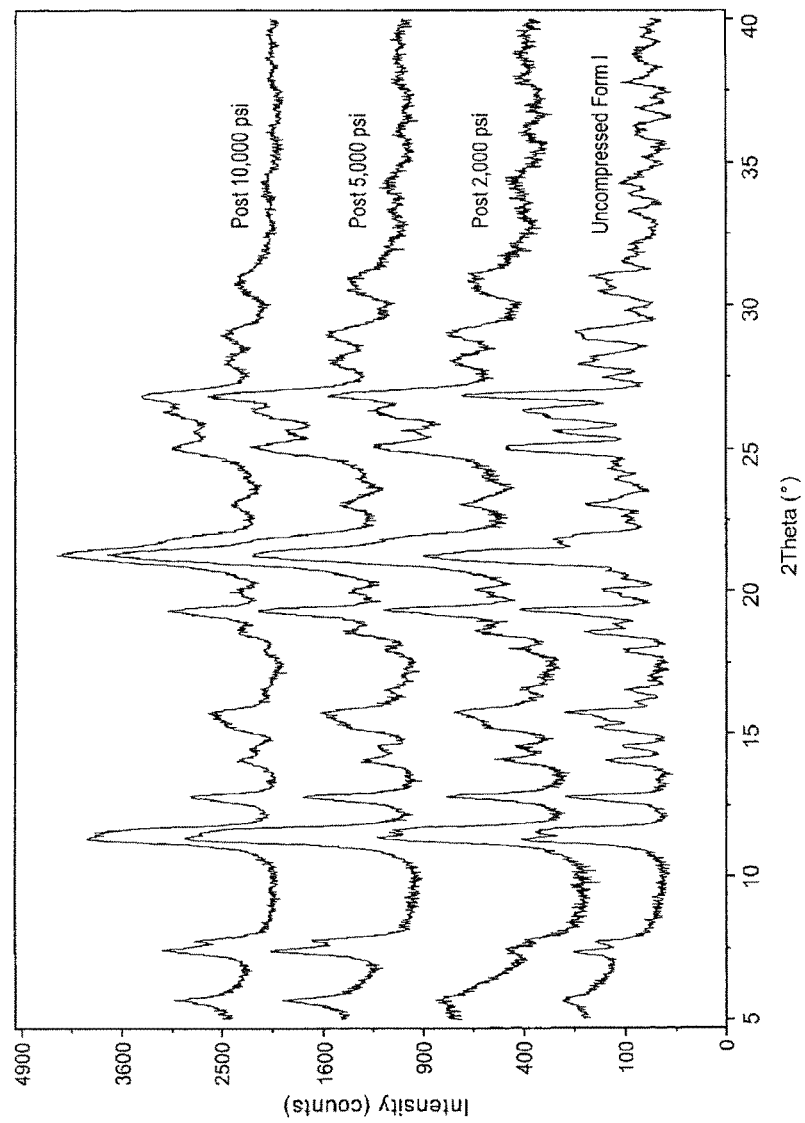
FIG. 7 depicts PXRD patterns of APD125 Form I compressed at 2 kp, 5 kp and 10 kp compared with uncompressed Form I. The PXRD patterns show that the samples all substantially comprise Form I.

Results:

In FIG. 6, an overlay of PXRD patterns for micronized APD125 Form I, before and after grinding with a mortar and pestle for 1 minute, 5 minutes and 10 minutes are compared. No significant changes in the PXRD patterns were observed, suggesting that Form I is stable to grinding/milling forces. In FIG. 7, PXRD patterns of APD125 Form I compressed at 2 kp, 5 kp and 10 kp are compared, with uncompressed Form I. All of the PXRD patterns are consistent with APD125 Form I, although with the possibility of a slight reduction in crystallinity, as suggested by peak broadening and a loss of peak resolution/intensity for the compressed samples, relative to the uncompressed control sample.

Example 5: Methyl Cellulose Optimization

Example 5.1: Test Blend Preparation

Example 5.1.1: Form I API Slurries in Water

In a small scintillation vial, 152.13 mg of micronized APD125 Form I, was spiked with sufficient deionized water to make a paste; the weight of the water added, 844.60 mg, was recorded, and the resulting mixture was stirred using a spatula to obtain a paste. The resulting sample, post-collection of an initial PXRD pattern, was capped, wrapped in tinfoil and stored at 40° C. until the next day, when a second PXRD pattern was obtained.

Using another small scintillation vial, 2.1183 g of micronized APD125 Form I, was mixed with 3.3619 g of a 0.5% w/v methyl cellulose to obtain a paste, which was immediately sampled for PXRD analysis to verify starting APD125 solid-state form, post-methyl cellulose addition. The remaining sample in the scintillation vial was split into two portions, placed in capped, parafilm-wrapped scintillation vials, which were then wrapped in tinfoil and stored at 40° C. and room temperature, respectively. PXRD patterns were collected at initial (t=0), 2-day and 16-day time points for each sample.

Example 5.1.2: Tablet Granulation Slurries in Water

APD125 micronized Form I/PVP (1:8) blend, weighing 3.0081 g and containing 0.5% w/w methyl cellulose, was mixed with 3.71277 g of water to form a paste. After sampling the paste for an initial PXRD pattern, the remaining paste was split into two portions, placed in capped, parafilm-wrapped scintillation vials, which were then wrapped in tinfoil and stored at 40° C. and room temperature, respectively. PXRD patterns were collected at initial (t=0), 1-day, 7-day and 21-day time points.

Example 5.1.3: Tablets (10 mg) Prepared Using 0% w/w, 2% w/w, 5% w/w and 8% w/w Methyl Cellulose For each blend, materials were dispensed (minus magnesium stearate) into a glass vial and blended for about 5 minutes. Magnesium stearate was added and the mixture was blended an additional 2 minutes. The final blend was compacted into standard round concave tablets (5/16" diameter) with a total tablet weight of 200 mg and hardness of 10 kp using a Carver press. For each batch of tablets, several were crushed using a mortar and pestle to obtain a fine powder, from which a small sample was taken for PXRD analysis to confirm the initial APD125 polymorphic form. The remaining powder was weighed into a Qorpak® bottle, and ca. 50% w/w deionized water was added. The resulting mixture was stirred using a micro-spatula to wet the powder and form a paste. A Teflon® lid was screwed on tightly, and the prepared samples were stored in a 40° C. oven. Ground tablet and water weights for each methyl cellulose loading are provided in Table 20. PXRD patterns were collected for the five tablet granulation/water blends, according to the schedule provided in Table 21.

TABLE 20

| Formulation Used | Weight of Powder (g) | Weight of Water (g) |
|---|---|---|
| APD125:PVP (1:8) 2% methyl cellulose | 1.4767 | 1.4802 |
| APD125:PVP (1:8) 5% methyl cellulose | 1.3173 | 1.5822 |
| APD125:CoPVP (1:8) 5% methyl cellulose | 1.5436 | 1.5172 |
| APD125:PVP (1:8) 8% methyl cellulose | 1.5355 | 1.5049 |
| APD125:PVP (1:8) | 1.64810 | 1.63835 |

TABLE 21

| Formulation Used | Time Point | XRD Results Suggest Major Presence of: |
|---|---|---|
| 2% methyl cellulose | Initial (no water) | Form I |
| | 1 day | Form I |
| | 1 week | Form II |
| | 4 weeks | — |
| 5% methyl cellulose, PVP | Initial (no water) | Form I |
| | 1 day | Form I |
| | 1 week | Form I |
| | 4 weeks | Form I |
| 5% methyl cellulose, coPVP | Initial (no water) | Form I |
| | 1 day | Form I |
| | 1 week | Form I |
| | 4 weeks | Form II |
| 8% methyl cellulose | Initial (no water) | Form I |
| | 1 day | Form I |
| | 1 week | Form I |
| | 4 weeks | Form I and Form II |
| 0% methyl cellulose | Initial (no water) | Form I |
| | 1 day | Form II |
| | 1 week | — |
| | 4 weeks | — |

Example 5.2: Powder X-Ray Diffraction

PXRD measurements were obtained using a Philips (PANalytical) X'Pert PRO theta/theta diffractometer (EQ 0233) equipped with an X'Celerator RTMS detector and utilizing copper Kα radiation, operating at 45 kV and 40 mA. The instrument radius was 239.5 mm, the mask filter was 20 mm, the soller slit was 0.04 radians, and a nickel filter and sample spinning were used during data acquisition. The application and instrument control software used were X'Pert Data Collector®, version 2.0c and XPERT-PRO®, version 1.6, respectively. The API-based paste samples were scanned from 5° to 40°2θ in continuous mode, using a step size of 0.0167°2θ and a counting time of 40.005 seconds. The tablet granulation samples were scanned from 2° to 15°2θ in continuous mode, using a step size of 0.0167°2θ and a counting time of 1063.625 s.

Figure 8:
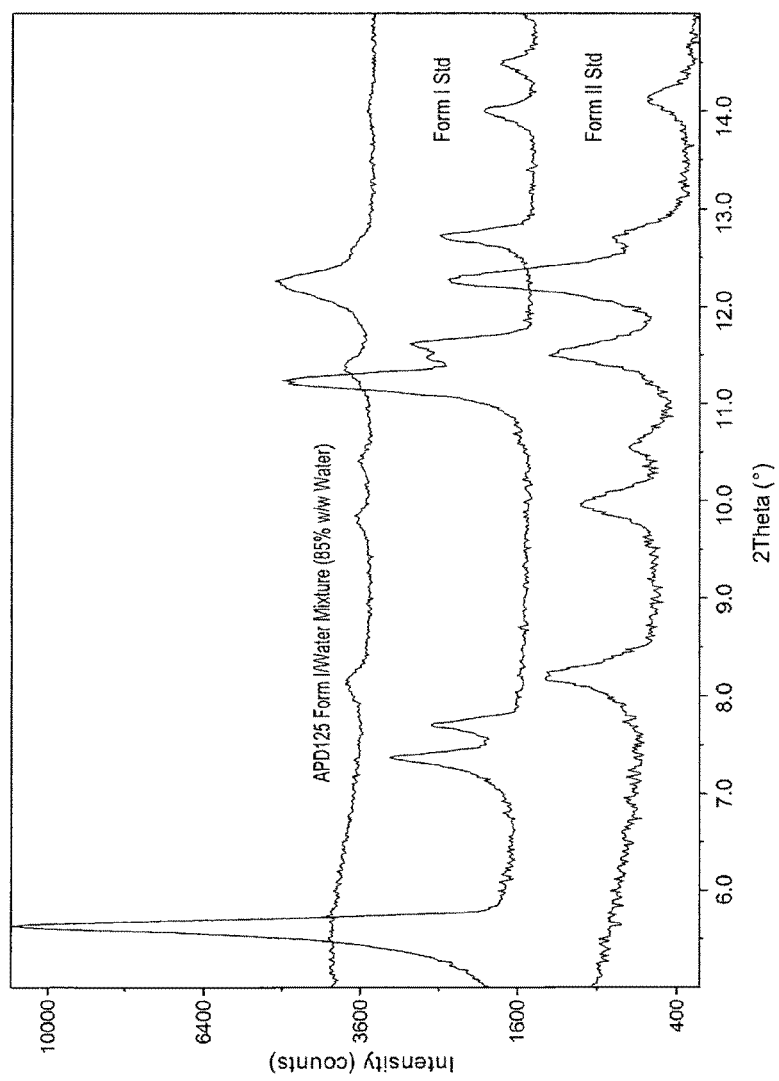
FIG. 8 depicts a PXRD pattern of an aqueous 0.5% w/w methyl cellulose solution of Form I at room temperature and 40° C. after 16 days. The PXRD pattern shows that the sample has substantially converted to Form II.
Figure 9:
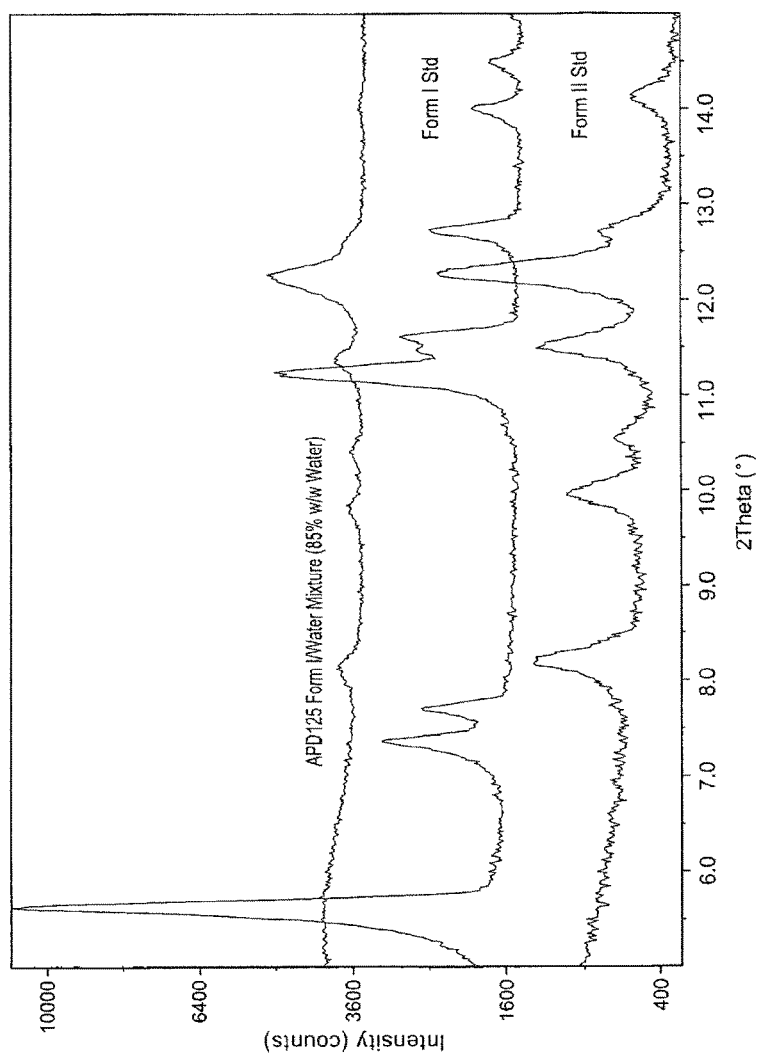
FIG. 9 depicts PXRD patterns of a Form I paste in water alone at room temperature and 40° C. after 24 h. The PXRD pattern shows that the sample has substantially converted to Form II.
Figure 10:
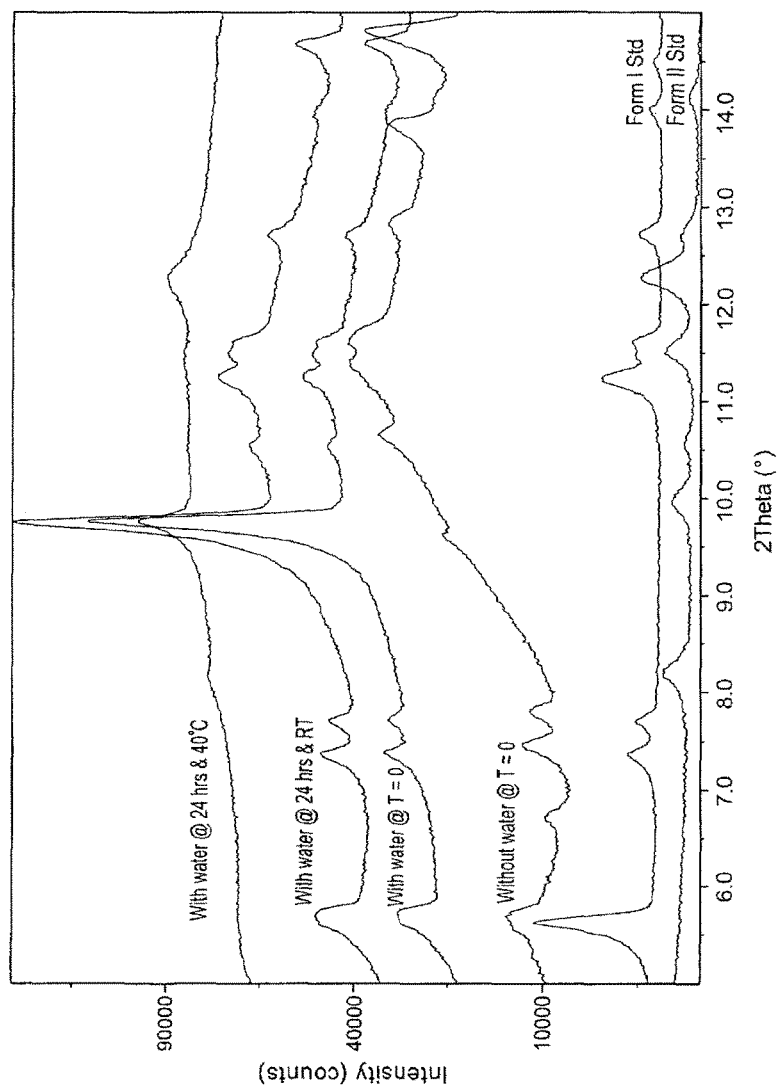
FIG. 10 depicts PXRD patterns for the wet-granulation Form I tablet blend post-mixing without water at t=0, and with 50% w/w water at t=0 and 24-h storage at room temperature and 40° C. The PXRD patterns show that each sample substantially comprises Form I.
Figure 11:
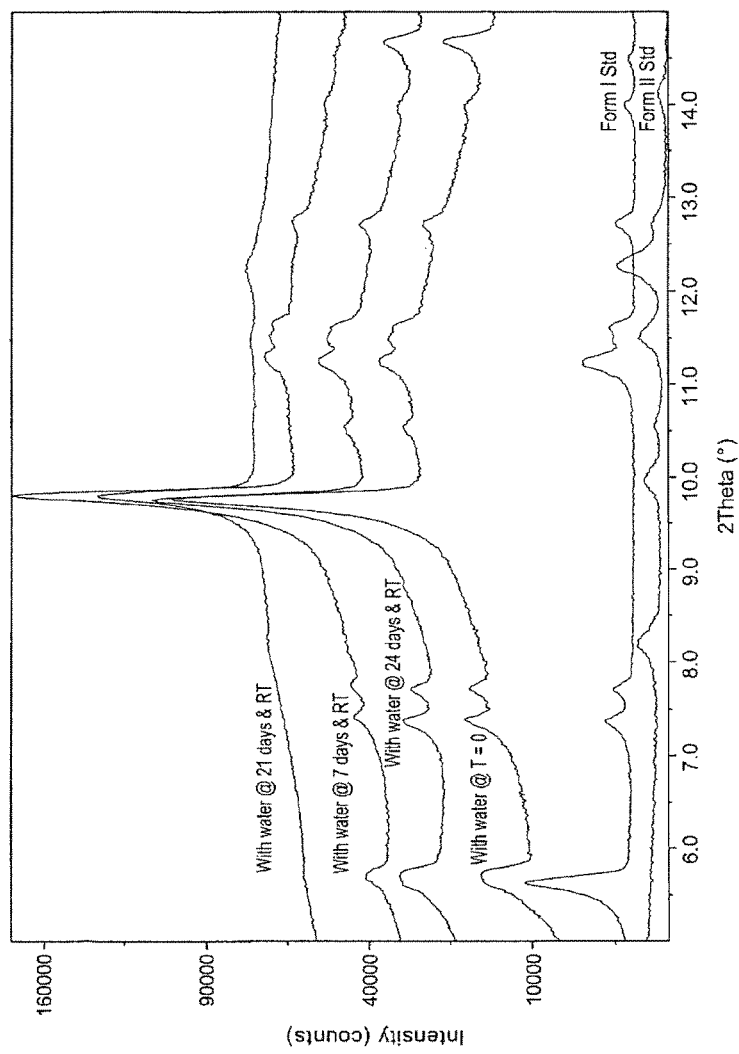
FIG. 11 depicts PXRD patterns for the Form I wet-granulation tablet blend post-mixing with 50% w/w water at t=0, 24-h, 7-days and 21-days storage at room temperature. The PXRD patterns show that at t=0, 24-h and 7-days the samples substantially comprise Form I, and at t=21 days the sample has substantially converted to Form II.

An aqueous 0.5% w/w methyl cellulose solution of Form I at 40° C. showed no evidence of conversion to Form II after 16 days (FIG. 8), in sharp contract to a Form I paste in water alone at 40° C., which converted to Form II within 24 hours (FIG. 9). As a result, 0.5% w/w methyl cellulose was added to the first APD125 wet-granulation tablet to hinder the conversion of Form I to Form II. However, the effectiveness of methyl cellulose in a tablet matrix has not been previously investigated. Therefore, as a first step, the wet-granulation tablet blend, containing 0.5% w/w methyl cellulose, was mixed with 50% w/w water to form a paste and stored at room temperature and 40° C. to determine if conversion to Form II was inhibited. Initial (t=0) and 24 hour PXRD patterns for the wet samples are shown in FIG. 10. After 24 hours, the sample stored at 40° C. showed conversion to Form II; while the room-temperature sample was still Form I. As shown in FIG. 11, the room-temperature sample remains Form I at 7 days, finally converting to Form II at 21 days.

Figure 12:
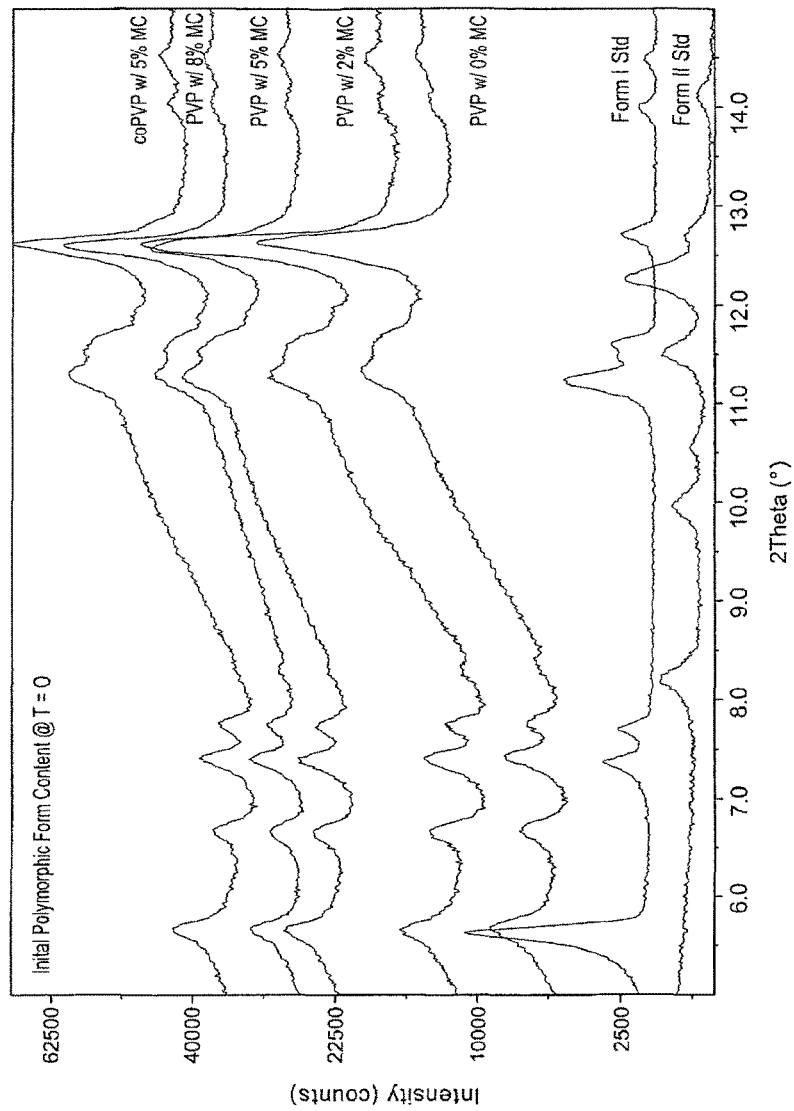
FIG. 12 depicts PXRD patterns for PVP-based direct-compression Form I tablets, containing 0% w/w, 2% w/w, 5% w/w and 8% w/w methyl cellulose and a coPVP-based direct-compression Form I tablet, containing 5% w/w methyl cellulose, post-mixing with 50% w/w water at t=0. The PXRD patterns show that each sample substantially comprises Form I.
Figure 13:
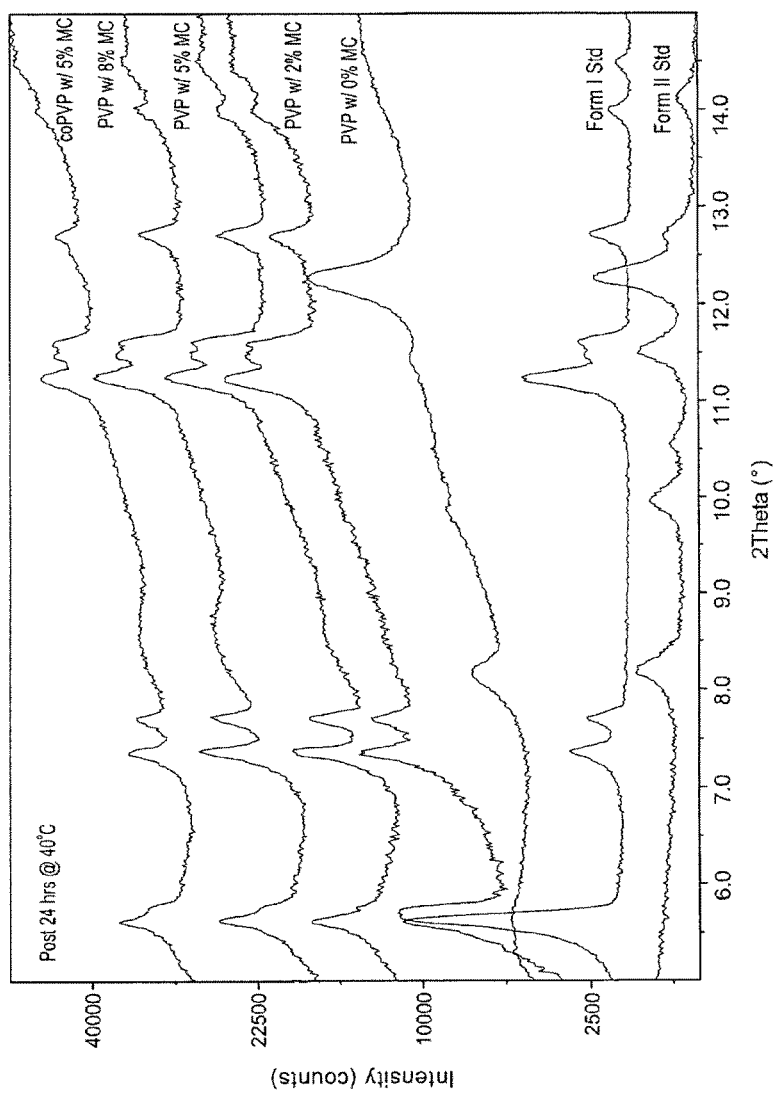
FIG. 13 depicts PXRD patterns for PVP-based direct-compression Form I tablets, containing 0% w/w, 2% w/w, 5% w/w and 8% w/w methyl cellulose, and a coPVP-based direct-compression tablet, containing 5% w/w methyl cellulose, post-mixing with 50% w/w water after 24 h at 40° C. The PXRD patterns show that the sample containing 0% methyl cellulose has substantially converted to Form II and all other samples substantially comprise Form I.

In contrast to pure APD125 Form I suspended in aqueous 0.5% w/w methyl cellulose, which did not convert to Form II in 21 days at room temperature, the tablet did show conversion to Form II. Therefore, it was decided to evaluate higher methyl cellulose concentrations to determine if conversion to Form II could be more effectively inhibited. PVP-based direct compression tablets were prepared containing 0% w/w, 2% w/w, 5% w/w and 8% w/w methyl cellulose. In addition, coPVP-based direct compression tablets were prepared containing 5% w/w methyl cellulose. In each case, the tablets were ground, mixed with 50% w/w water and stored at 40° C., with PXRD patterns collected at t=0, 24 h, 1 week and 4 weeks (1 month). As shown in FIG. 12, all samples contained Form I initially, but by 24 hours (FIG. 13), the sample without methyl cellulose showed conversion to Form II, as was previously observed for the 0.5% w/w methyl cellulose tablet blend.

Figure 14:
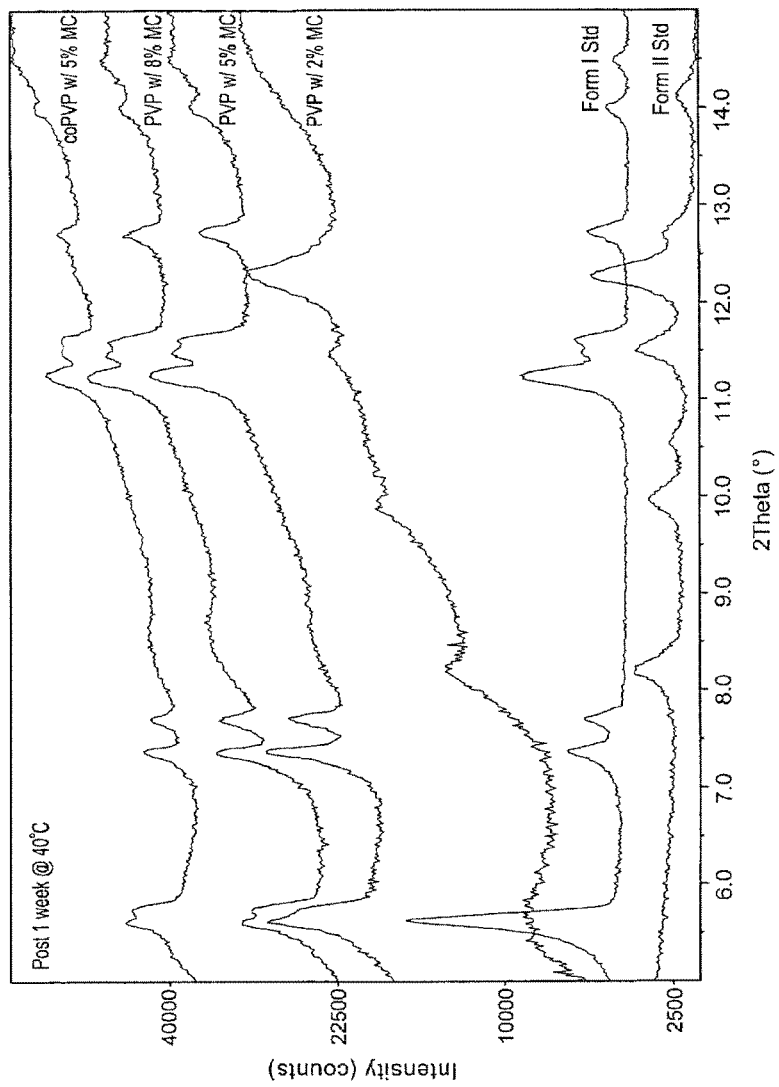
FIG. 14 depicts PXRD patterns for PVP-based direct-compression Form I tablets, containing 0% w/w, 2% w/w, 5% w/w and 8% w/w methyl cellulose, and a coPVP-based direct-compression Form I tablet, containing 5% w/w methyl cellulose, post-mixing with 50% w/w water after 1 week at 40° C. The PXRD patterns show that the sample containing 2% methyl cellulose has substantially converted to Form II and all other samples substantially comprise Form I.
Figure 15:
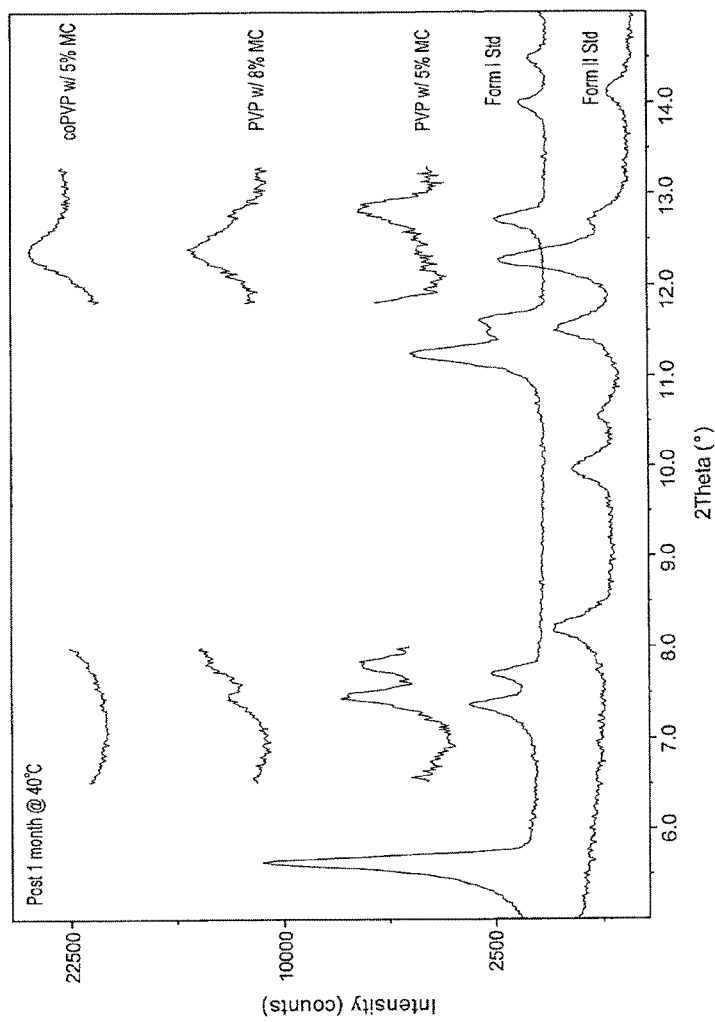
FIG. 15 depicts PXRD patterns for PVP-based direct-compression Form I tablets, containing 5% w/w and 8% w/w methyl cellulose, and a coPVP-based direct-compression From I tablet, containing 5% w/w methyl cellulose, post-mixing with 50% w/w water after 1 month at 40° C. The PXRD patterns show that the sample containing PVP and 5% methyl cellulose substantially comprises Form I, the sample containing PVP and 8% methyl cellulose has partially converted to Form II, and the sample containing coPVP has substantially converted to Form II. Note that the tablet PXRD data acquisition scan window was reduced to two smaller regions of 6.5° to 8°2θ and 11.8° to 13.3°2θ to reduce the overall sample analysis time, while maintaining the ability to discriminate Form I from Form II.

After 1 week at 40° C., the 2% w/w methyl cellulose sample showed conversion to Form II (FIG. 14), while the remaining samples, containing 5% w/w and 8% w/w methyl cellulose, started to show conversion to Form II at 1 month (FIG. 15). Thus, 2% w/w, 5% w/w and 8% w/w methyl cellulose containing tablets showed retarded conversion to Form II relative to the 0% w/w methyl cellulose control and the previously studied 0.5% w/w methyl cellulose containing tablet.

In addition to maintaining Form I, a primary goal of APD125 tablet formulation development is to minimize DFA formation. As can be seen in Table 25, although methyl cellulose loadings of 5% w/w and 8% w/w exhibited the best inhibition of Form II, they also resulted in increased DFA formation, relative to the 0% w/w methyl cellulose control. In addition, at the 5% w/w methyl cellulose loading, the coPVP-based tablets showed over three times the DFA formation of the PVP-based tablets, suggesting, as in the case of the TAM results, that coPVP might be less desirable as an excipient than PVP. The 2% w/w methyl cellulose loading provided the best overall balance of optimal chemical stability, while retaining a reasonable ability to inhibit the formation of Form II (FIG. 13, Table 25), and therefore, was used as the basis of further tablet development.

Example 5.3: DFA Assay

In addition to maintaining Form I, a primary goal of APD125 tablet formulation development was to minimize DFA formation. The 4-week 40° C./75% RH samples were pulled from their stability chambers and allowed to dry over the course of a couple of days under nitrogen. The material was then broken up using a micro-spatula until enough material was available for the DFA HPLC analysis. The samples were allowed to sit in solution for 4 hours before being filtered by centrifugation and transferred into an HPLC vial for analysis. Manual integration was used for all chromatograms.

As can be seen in Table 22, although methyl cellulose loadings of 5% w/w and 8% w/w exhibited the best inhibition of Form II, they also resulted in increased DFA formation, relative to the 0% w/w methyl cellulose control. In addition, at the 5% w/w methyl cellulose loading, the coPVP-based tablets showed over three times the DFA formation of the PVP-based tablets, suggesting, as in the case of the TAM results, that coPVP might be less desirable as an excipient than PVP. The 2% w/w methyl cellulose loading provided the best overall balance of optimal chemical stability, while retaining a reasonable ability to inhibit the formation of Form II (FIG. 13, Table 22), and therefore, was used as the basis of further tablet development.

adhesive on a disposable scanning electron microscopy (SEM) stage at a height no greater than 0.5 cm. The SEM stage was lightly tapped to remove any loose material that did not adhere to the adhesive, and the prepared sample was placed in the SEM chamber. Images were collected using a FEI Quanta 200 (S/N D7554-R).

The 1:1 blend showed significant amounts of residual APD125 not coated onto the PVP particles, whereas the 1:3, 1:5 and 1:8 SEM images showed similar and significantly less residual APD125, not coated onto PVP, suggesting an API:PVP ratio of greater than 1:1, but no more than 1:3 is required to disperse most of the APD125 onto the PVP. APD125 does not uniformly coat the PVP particles, but tends to adhere more thickly to some areas than others, possibly due to variations in electrostatics.

Similar SEM results were obtained for API/coPVP blends. Once again, based upon the SEM images, it would appear that the least residual APD125 was observed at API:coPVP ratios of 1:3 or greater.

TABLE 22

| Formulation | Form Detected | | | DFA (n = 1) |
| --- | --- | --- | --- | --- |
| | (1 day) | (1 week) | (4 weeks) | (4 weeks) |
| APD125 Form I/PVP (1:8) No methyl cellulose | Form II | Not applicable | Not applicable | 37 ppm |
| APD125 Form I/PVP (1:8) 2% w/w methyl cellulose | Form I | Form II | Not applicable | 34 ppm |
| APD125 Form I/PVP (1:8) 5% w/w methyl cellulose | Form I | Form I | Form I | 80 ppm |
| APD125 Form I/coPVP (1:8) 5% w/w methyl cellulose | Form I | Form I | Form II | 292 ppm |
| APD125 Form I/PVP (1:8) 8% w/w methyl cellulose | Form I | Form I | Form I/Form II mixture | 105 ppm |

Example 6: PVP/API and coPVP/API Ratio Optimization

Example 6.1: Sample Preparation

APD125 Form I and either PVP or coPVP were weighed out and mixed to obtain API/PVP or API/coPVP ratios of 1:1, 1:3, 1:5 and 1:8. The resulting mixtures were blended for ca. 5 min, screened through a #40 screen, and blended for an additional ca. 5 minutes.

Example 6.2: Scanning Electron Microscopy Analysis

Figure 16:
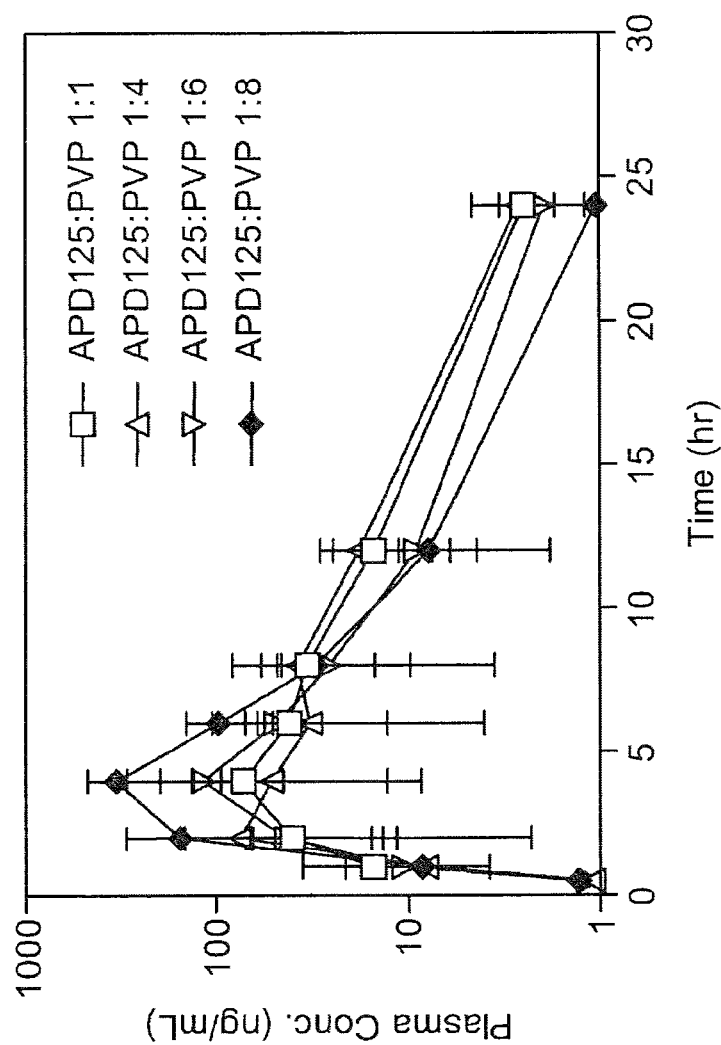
FIG. 16 depicts the effect of APD125/Pvp ratio on the APD125 plasma exposure in monkeys after oral administration of 10-mg direct-compression (dry) tablets.
Figure 17:
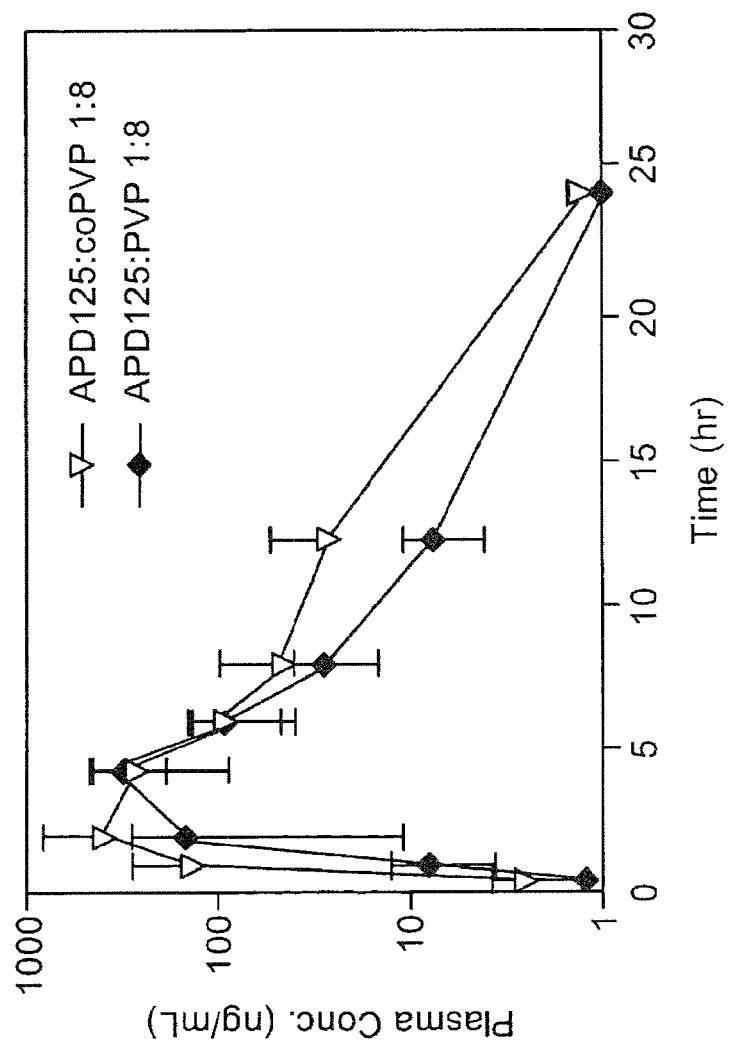
FIG. 17 depicts the effect of PVP and coPVP on the APD125 plasma exposure in monkeys after oral administration of 10-mg direct-compression (dry) tablets, containing either APD125:PVP (1:8) or APD125:coPVP (1:8).
Figure 20:
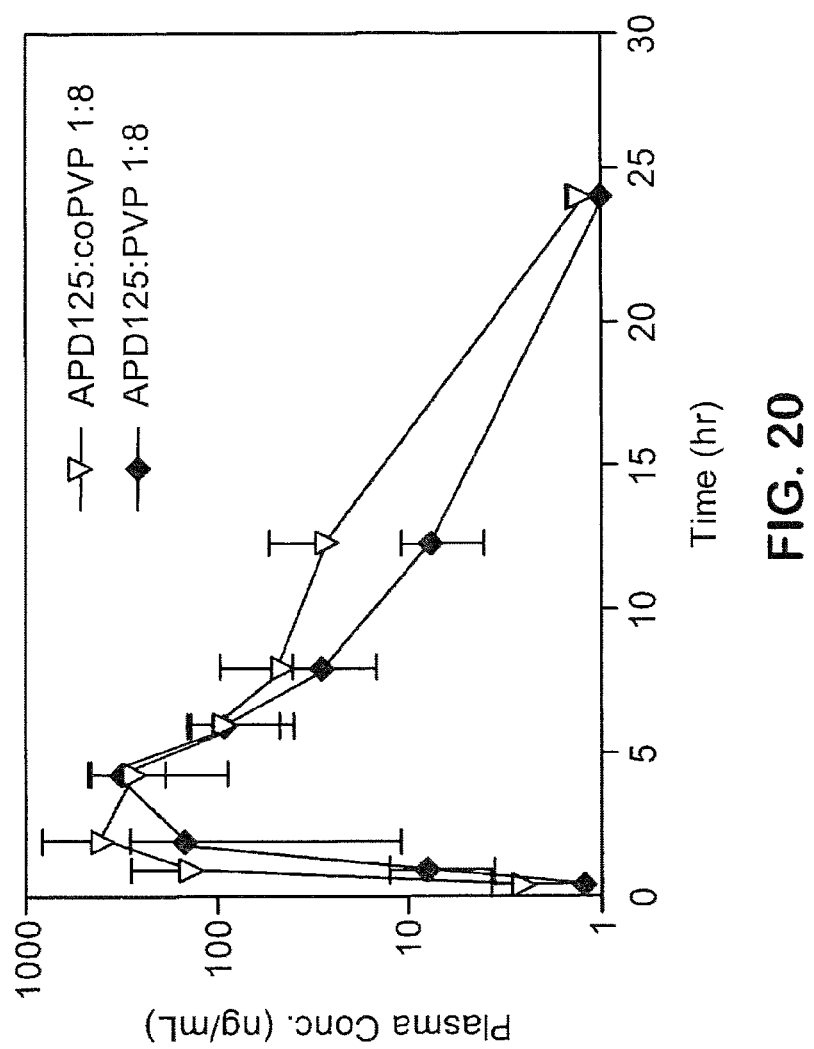
FIG. 20 depicts APD125 plasma exposure in monkeys after oral administration of direct-compression tablets (10 mg) containing either APD125:PVP (1:8) or APD125:coPVP (1:8).

Each sample was lightly stirred with a micro-spatula and a small portion of the material was tapped onto double-sided Example 6.3: Monkey APD125 Plasma Exposure—APD125 Form I:PVP and APD125 Form I:coPVP Tablet Formulations The effects of PVP and coPVP in various ratios with APD125 on APD125 plasma exposure in monkeys after oral administration of direct (dry) compression tablets containing 10 mg of APD125 were examined. APD125 plasma exposure ($AUC_{0-\infty}$) at APD125:PVP ratios of 1:1, 1:4 and 1:6 were similar at 0.548±0.321 h·µg/mL, 0.575±0.379 h·µg/mL and 0.572±0.556 h·µg/mL, respectively. At an APD125:PVP ratio of 1:8, however, plasma exposure (1.262±0.660 h·µg/mL) increased twofold compared to the 1:1, 1:4 and 1:6 ratios (FIG. 16, Table 23). The replacement of PVP with coPVP in the direct compression tablet at a ratio of 1:8 did not affect APD125 exposure: APD125:PVP, 1.262±0.660 h·µg/mL; APD125:coPVP, 1.889±1.162 h·µg/mL (FIG. 20, Table 23). Therefore, the final prototype tablets were 1:8 APD125:PVP or 1:8 APD125:coPVP ratio based formulations.

TABLE 23

| Formulation | Dose (mg) | N | $C_{max}$ (µg/mL) | | $AUC_{0-\infty}$ (h·µg/mL) | | $t_{max}$ (h) | |
| --- | --- | --- | --- | --- | --- | --- | --- | --- |
| | | | Mean | SD | Mean | SD | Mean | SD |
| APD125 Form I:PVP (1:1) DC | 10 | 6 | 0.077 | 0.057 | 0.548 | 0.321 | 4.7 | 2.1 |
| APD125 Form I:PVP (1:4) DC | 10 | 6 | 0.085 | 0.071 | 0.575 | 0.379 | 4.7 | 4.3 |
| APD125 Form I:PVP (1:6) DC | 10 | 6 | 0.125 | 0.174 | 0.572 | 0.556 | 4.3 | 2.3 |

TABLE 23-continued

| Formulation | Dose (mg) | N | $C_{max}$ (µg/mL) Mean | SD | $AUC_{0-\infty}$ (h·µg/mL) Mean | SD | $t_{max}$ (h) Mean | SD |
|---|---|---|---|---|---|---|---|---|
| APD125 Form I:PVP (1:8) DC | 10 | 3 | 0.335 | 0.138 | 1.262 | 0.660 | 2.7 | 0.8 |
| APD125 Form I:coPVP (1:8) DC | 10 | 5 | 0.471 | 0.413 | 1.889 | 1.162 | 2.4 | 0.9 |
| APD125 Form I:PVP (1:8) WET | 10 | 6 | 0.227 | 0.153 | 1.507 | 1.218 | 2.2 | 1.0 |
| Soft gelatin capsule | 10 | 6 | 0.942 | 0.303 | 3.192 | 1.291 | 2.2 | 1.0 |

Example 7: Direct Compression Tablet

Example 7.1: Micronization of APD125 Form I

APD125 Form I (12.5 kg, particle size $d_{10}$ of 1.75 µm, $d_{50}$ of 6.98 µm, $d_{90}$ of 38.45 µm) (Sympatec Helos wet dispersion laser diffraction particle size analyzer) was micronized in a 300 mm spiral jet mill at a solid feed rate of 20.0 kg/h with a grinding pressure of 6.5±0.5 bar and a filtered nitrogen gas feed pressure of 10±0.5 bar to produce APD125 Form I (11.55 kg, 92.4% yield) of 99.93% purity by HPLC peak area. The micronized product was found to have a particle size $d_{90}$ of 6.16 µm with a Sympatec Helos wet dispersion laser diffraction particle size analyzer.

Example 7.2: Tablet Manufacturing for 5% w/w Methyl Cellulose-Loaded Tablets Materials were dispensed according to the target tablet quantitative composition. Micronized APD125, PVP and methyl cellulose were preblended in a bag, and then hand-screened through a #40-mesh sieve. A 2-qt. blender was charged with the preblend, and all other remaining materials were added, minus the magnesium stearate, followed by blending for 300 rotations (12 min at 25 rpm). Finally, the magnesium stearate was added, and the resulting mixture was blended for an additional 100 rotations (4 minutes at 25 rpm). This material was compressed into 200-mg tablets using a Piccola PLC tablet press equipped with two stations of 5/16" standard round concave tooling to achieve a target 5-kp to 8-kp tablet hardness.

Example 7.3: Tablet Manufacturing for 2% w/w Methyl Cellulose-Loaded Tablets Materials were dispensed according to the target tablet quantitative composition. A blender was charged with all of the tablet components, minus magnesium stearate, and blended for 300 rotations (12 min at 25 rpm). The resulting blend was delumped using a Comill (equipped with an R045 screen and round-arm impeller), transferred into a blender, and blended for 300 rotations (12 min at 25 rpm). The magnesium stearate was added, followed by blending for an additional 100 rotations (4 min at 25 rpm). The resulting final blend was compressed into 200-mg tablets (containing 10 mg of micronized APD125 Form I API) to a target hardness of 5 kp to 8 kp, using a Piccola PLC tablet press, equipped with 5/16" standard round concave tooling. For the 40-mg active tablets, the final blend was compressed into 800-mg tablets to a target hardness of 12 kp to 16 kp, using 0.730"×0.365" plain oval tooling. Finally, all tablet cores were film coated with Opadry® II Blue 85F90996 to a 5% weight gain, using a fully perforated 11.5" pan. Final tablet composition is provided in Table 24.

TABLE 24

| Ingredient | % (w/w) | Amount (g) |
|---|---|---|
| Core tablet | | |
| APD125 (Micronized) | 5.00 | 50.0 |
| PVP, Plasdone ™ K-29/32 or coPVP, Kollidon ™ VA 64 | 40.00 | 400.0 |
| Lactose monohydrate, 316 | 21.25 | 212.5 |
| Microcrystalline cellulose, PH102 | 25.00 | 250.0 |
| Crospovidone, Kollidon ™ CL | 4.00 | 40.0 |
| Methyl cellulose | 2.00 | 20.0 |
| Sodium lauryl sulfate | 2.00 | 20.0 |
| Magnesium stearate | 0.50 | 5.0 |
| Silicon dioxide | 0.25 | 2.5 |
| Total | 100.00 | 1000.0 |
| Film coat | | |
| Opadry ® II Blue 85F90996 | 5 | NA |

NA = not applicable

Example 7.4: Monkey APD125 Plasma Exposure

Monkey APD125 exposure studies conducted with wet granulation based APD125 Form I 10-mg tablets, containing 0.5% w/w methyl cellulose, were shown to exhibit roughly one-half the $AUC_{0-\infty}$ and one-fourth the $C_{max}$ of SGCs (Example 1.1). Additionally, monkey studies using uncoated direct compression APD125 Form I 10-mg tablets, containing 5% w/w methyl cellulose found the direct compression tablets to exhibit essentially the same exposure as previously observed for the wet-granulation tablets (Example 6.3). Based on the PK data and the methyl cellulose formulation stability results (Table 22), a decision was made to prepare two final, separate R&D batches of coated direct-compression tablets with 40 mg APD125 Form I, containing methyl cellulose at 2% w/w, and either PVP or coPVP.

Figure 18:
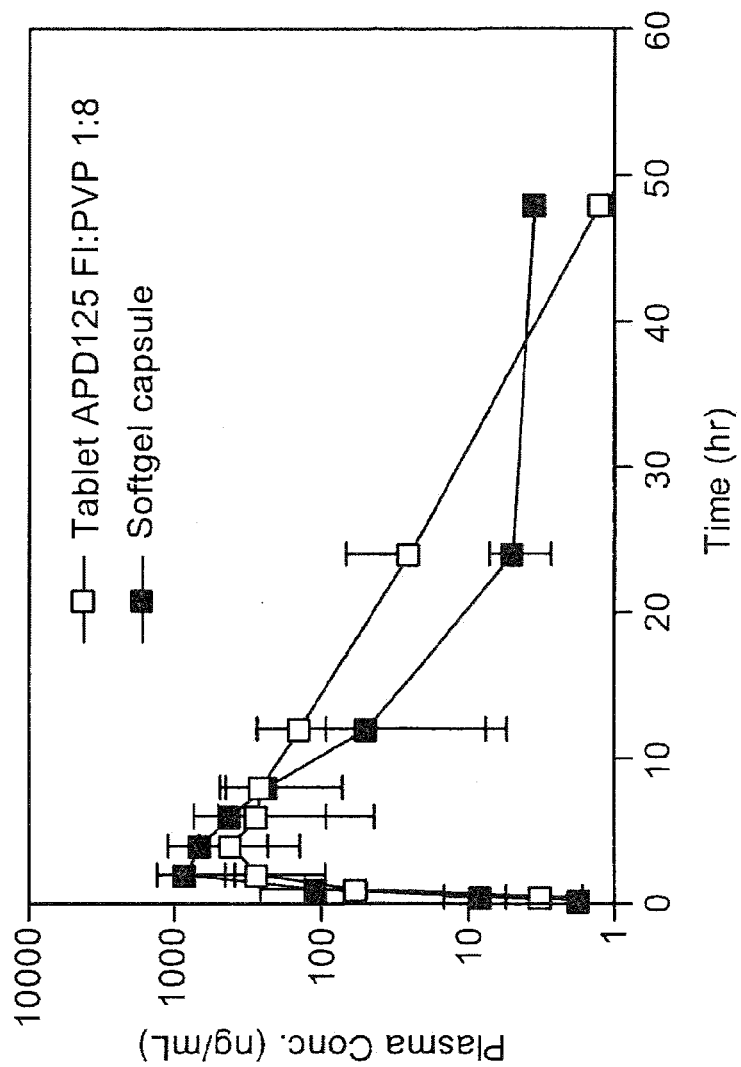
FIG. 18 depicts APD125 plasma exposure in monkeys after oral administration of direct-compression tablets (composition: 40 mg APD125 Form I:PVP [1:8], containing 2% w/w methyl cellulose) or SGCs (composition: 40 mg APD125 in Cremophor®:Labrasol® [1:1]).

Six monkeys were dosed in a 2×6 crossover design. APD125 plasma exposure after oral administration of 40 mg APD125 in SGC or dry compression tablets are shown in FIG. 18. Pharmacokinetic parameters are presented in Table 25. APD125 absorption into the systemic circulation occurred over a 3-h period followed by a mono-exponential terminal phase. The time to maximal plasma concentration ($t_{max}$) was most rapid for the liquid filled SGC at 2.2 h. The $t_{max}$ increased with tablet administration to 3.3 h. The SGC $C_{max}$ (0.850±0.462 µg/mL) was approximately twofold greater than the $C_{max}$ for APD125 Form I tablet (0.464±0.236 µg/mL). The integrated plasma exposures ($AUC_{0-\infty}$) for SGC and APD125 Form I tablet were similar (4.395±3.122 h·µg/mL) and APD125 Form I (4.223±2.660 h·µg/mL). The extended $t_{max}$, reduced Cmax and similar overall exposures ($AUC_{0-\infty}$) of the tablet formulation compared to the SGC formulation corroborate the exploratory formulations discussed in Example 1.1 (Table 1).

TABLE 25

| Formulation | Dose (mg) | N | $C_{max}$ (μg/mL) Mean | SD | $AUC_{0-\infty}$ (h·μg/mL) Mean | SD | $t_{max}$ (h) Mean | SD |
|---|---|---|---|---|---|---|---|---|
| Tablet APD125 Form I:PVP (1:8) coated direct-compression, 2% w/w methyl cellulose | 40 | 6 | 0.46 | 0.236 | 4.223 | 2.660 | 3.3 | 1.0 |
| Soft gelatin capsule | 40 | 6 | 0.850 | 0.462 | 4.395 | 3.122 | 2.2 | 1.0 |

As can be seen in Table 25, APD125 Form I:PVP (1:8) coated direct-compression tablets exhibit essentially identical $AUC_{0-\infty}$ results to the SGC at a 40-mg dose, as was expected on the basis of the previous wet-granulation tablet monkey PK results. Additionally, the 40-mg tablets exhibited roughly one-half the $C_{max}$ of the SGCs and a slightly longer $t_{max}$, which is also consistent with previous wet granulation tablet PK results.

Example 7.5: R&D Stability Testing 10-mg and 40-mg, PVP and coPVP-based prototype APD125 tablets were placed on stability at 25° C./60% RH and 40° C./75% RH, contained in HDPE bottles with induction seal and desiccant. Appearance, dissolution, water content by Karl Fischer, PXRD, related substances and tablet hardness tests were performed at initial and 8-week time points only. Compound II, DFA and related substances were assayed at initial, 2-week and 4-week time points. Additional tablets were also stored in open containers at 40° C./75% RH, pulled and analyzed at the 4-week time point for DFA and compound II.

PVP-based and coPVP-based tablet formulations showed comparable overall chemical stability during the 8-week study, with no significant loss in APD125 observed, as demonstrated by the assay results shown in Table 26. The DFA results for the final two R&D formulations are provided in Table 27.

TABLE 26

| | | | APD125 % Assay (% RSD) | | | |
|---|---|---|---|---|---|---|
| Formulation | Conditions | Dose (mg) | Initial n = 3 | 2 weeks n = 3 | 4 weeks n = 3 | 8 weeks 0 = 3 |
| APD125 Form I:PVP (1:8) 2% w/w methyl cellulose, direct-compression (coated) | 40° C. 75% RH | 10 | 90.5 (0.5) | 93.0 (0.6) | 102.3 (4.9) | 93.7 (2.4) |
| | 75% RH | 40 | 93.1 (0.5) | 91.3 (0.7) | 102.3 (3.6) | 97.7 (2.1) |
| | 25° C. | 10 | 90.5 (0.5) | NT | NT | 95.4 (2.1) |
| | 60% RH | 40 | 93.1 (0.5) | NT | NT | 96.9 (2.0) |
| APD125 Form I:coPVP (1:8) 2% w/w methyl cellulose, direct-compression (coated) | 40° C. | 10 | 90.4 (0.5) | 91.8 (1.8) | 92.6 (0.9) | 95.1 (1.5) |
| | 75% RH | 40 | 92.5 (1.5) | 97.5 (5.9) | 93.1 (0.9) | 97.0 (0.9) |
| | 25° C. | 10 | 90.4 (0.5) | NT | NT | 93.3 (1.1) |
| | 60% RH | 40 | 92.5 (1.5) | NT | NT | 96.7 (2.7) |

NT = not tested

TABLE 27

| | | | DFA Concentration as ppm (% RSD) | | | |
|---|---|---|---|---|---|---|
| Formulation | Conditions | Dose (mg) | Initial n = 2 | 2 weeks n = 2 | 4 weeks n = 2 | 8 weeks n = 2 |
| APD125 Form I:PVP (1:8) 2% w/w methyl cellulose, direct-compression (coated), HDPE bottle with desiccant | 40° C. | 10 | ND[a] | <35 | <35 | <35 |
| | 75% RH | 40 | ND[a] | <35 | <35 | <35 |
| | 25° C. | 10 | ND[a] | NA | NA | ND[a] |
| | 60% RH | 40 | ND[a] | NA | NA | ND[a] |
| APD125 Form I:coPVP (1:8) 2% w/w methyl cellulose, direct-compression (coated), HDPE bottle with desiccant | 40° C. | 10 | ND[a] | 69 (1.8) | 114 (1.7) | 142 (2.4) |
| | 75% RH | 40 | ND[a] | 67 (1.2) | 145 (0.6) | 161 (1.1) |
| | 25° C. | 10 | ND[a] | NA | NA | ND[a] |
| | 60% RH | 40 | ND[a] | NA | NA | ND[a] |
| APD125 Form I:PVP (1:8) 2% w/w methyl cellulose, direct-compression (coated), open container | 40° C. | 10 | ND[a] | NA | 645 (0.2) | NA |
| | 75% RH | 40 | ND[a] | NA | 918 (0.5 | NA |
| APD125 Form I:coPVP (1:8) 2% w/w methyl cellulose, direct-compression (coated), open container | 40° C. | 10 | ND[a] | NA | 648 (1.7) | NA |
| | 75% RH | 40 | ND[a] | NA | 788 (1.4) | NA |

[a]DFA limit of detection and limit of quantitation are 10 ppm and 35 ppm respectively
NA = not applicable
ND = Not detected As was previously observed during the methyl cellulose optimization studies (Table 22), the coPVP-based tablets were found to exhibit faster DFA formation rates than the corresponding PVP-based tablets, which is also consistent with TAM results (Example 3), suggesting potential compatibility issues with coPVP. Interestingly, the open-container results (Table 27) show similar DFA formation rates for both PVP-based and coPVP-based tablets, in contrast with HDPE bottle stability and methyl cellulose optimization results, which suggested tablets containing coPVP exhibit faster DFA formation than PVP-based tablets. This apparent discrepancy might be due to water content differences. In the cases of the HDPE bottle stability and methyl cellulose optimization studies, the amount of water present in the samples is very similar, which allows one to better assess the impact of changing from PVP to coPVP. However, in the case of the open-container stability study results, each sample would equilibrate to quite different water contents, as shown in FIG. 20. At a relative humidity of 75%, the PVP-based tablets could be expected to absorb significantly more water than the coPVP-based tablets, and since hydrolysis is a major pathway for DFA formation, it is not unreasonable that the open container PVP-based tablets would begin to show faster DFA formation, becoming nearly identical to the open container coPVP-based tablets. It is therefore possible that the observed increased DFA formation rate in the presence of coPVP, relative to PVP, is not the result of chemical incompatibility with coPVP. Instead, at a fixed water content in a closed system, the more hygroscopic PVP, relative to coPVP, might reduce the amount of free water available for hydrolysis of APD125.

Figure 19:
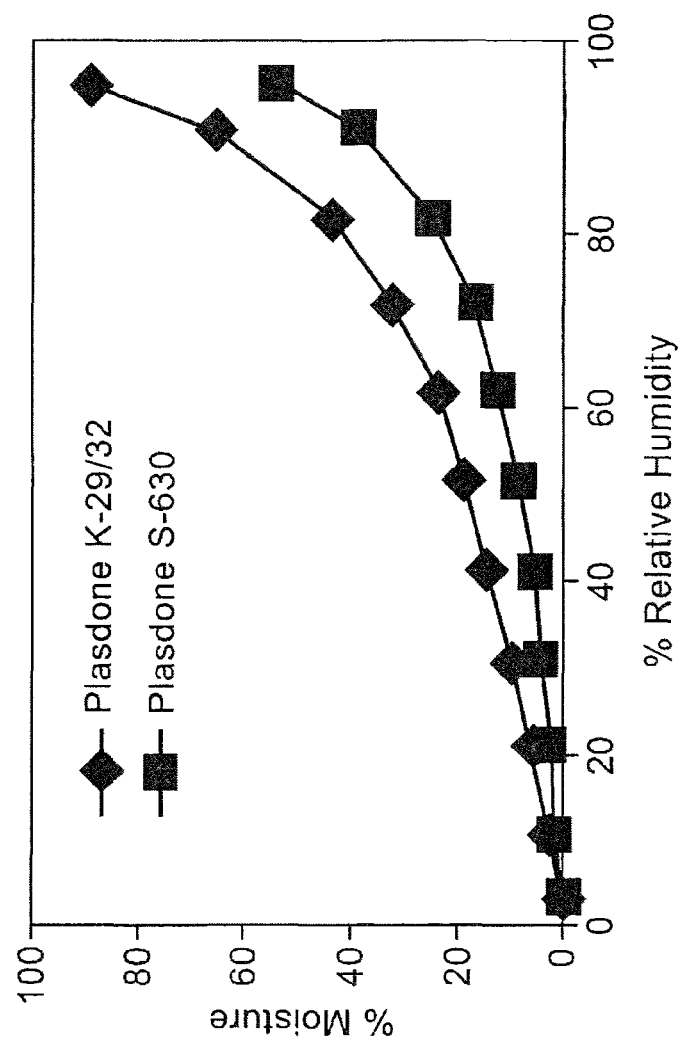
FIG. 19 depicts a hygroscopicity plot for Plasdone™ S-630 (coPVP) copolymer versus Plasdoner™ K-29/32 (PVP) homopolymer.

As shown in Table 28 and Table 29, both PVP-based and coPVP-based tablets exhibited no evidence of significant Compound II assay and dissolution rate changes post-8 weeks at 40° C./75% RH, with the exception of the open container results, consistent with the DFA results, shown in Table 27. The PXRD results show that all samples tested contain Form I, indicating good solid-state form stability for both PVP-based and coPVP-based tablets (Table 30). The water content determination by Karl Fischer showed essentially no change in water content over the 8-week study (Table 31). There was, however, a slightly higher water content observed for the PVP-based tablets, relative to the coPVP-based tablets, which is consistent with the fact that PVP is somewhat more hygroscopic than coPVP (FIG. 19).

TABLE 28

| Formulation | Conditions | Dose (mg) | Compound II Concentration as % area (% RSD) | | | |
|---|---|---|---|---|---|---|
| | | | Initial n = 2 | 2 weeks n = 2 | 4 weeks n = 2 | 8 weeks n = 2 |
| APD125 Form I:PVP (1:8) 2% w/w methyl cellulose, direct-compression (coated), HDPE bottle with desiccant | 40° C. 75% RH 25° C. 60% RH | 10 40 10 40 | ND$^a$ ND$^a$ ND$^a$ ND$^a$ | ND$^a$ ND$^a$ NA NA | ND$^a$ ND$^a$ NA NA | <0.05 <0.05 <0.05 <0.05 |
| APD125 Form I:coPVP (1:8) 2% w/w methyl cellulose, direct-compression (coated), HDPE bottle with desiccant | 40° C. 75% RH 25° C. 60% RH | 10 40 10 40 | ND$^a$ ND$^a$ ND$^a$ ND$^a$ | ND$^a$ ND$^a$ NA NA | ND$^a$ ND$^a$ NA NA | <0.05 <0.05 <0.05 <0.05 |
| APD125 Form I:PVP (1:8) 2% w/w methyl cellulose, direct-compression (coated), open container | 40° C. 75% RH | 10 40 | ND$^a$ ND$^a$ | NA NA | 0.24 (5.89) 0.26 (2.77) | NA NA |
| APD125 Form I:coPVP (1:8) 2% w/w methyl cellulose, direct-compression (coated), open container | 40° C. 75% RH | 10 40 | ND$^a$ ND$^a$ | NA NA | 0.24 (5.89) 0.33 (15.23) | NA NA |

TABLE 29

| Formulation | Conditions | Dose (mg) | APD125 % Released at 60 min (% RSD) | |
|---|---|---|---|---|
| | | | Initial n = 4 | 8 weeks n = 4 |
| APD125 Form I:PVP (1:8) 2% w/w methyl cellulose, direct-compression (coated) | 40° C. 75% RH 25° C. 60% RH | 10 40 10 40 | 103.9 (3.4) 98.9 (2.5) 103.9 (3.4) 98.9 (2.5) | 97.0 (3.1) 95.9 (1.4) 101.0 (1.7) 100.4 (2.0) |
| APD125 Form I:coPVP (1:8) 2% w/w methyl cellulose, direct-compression (coated) | 40° C. 75% RH 25° C. 60% RH | 10 40 10 40 | 100.0 (0.7) 98.3 (1.3) 100.0 (0.7) 98.3 (1.3) | 95.6 (0.9) 94.5 (0.8) 99.0 (0.9) 98.9 (0.8) |

TABLE 30

| Formulation | Conditions | Dose (mg) | APD125 Polymorph(s) Detected | |
|---|---|---|---|---|
| | | | Initial | 8 weeks |
| APD125 Form I:PVP (1:8) 2% w/w methyl cellulose, direct-compression (coated) | 40° C. 75% RH 25° C. 60% RH | 10 40 10 40 | Form I Form I Form I Form I | Form I Form I Form I Form I |
| APD125 Form I:coPVP (1:8) 2% w/w methyl cellulose, direct-compression (coated) | 40° C. 75% RH 25° C. 60% RH | 10 40 10 40 | Form I Form I Form I Form I | Form I Form I Form I Form I |

TABLE 31

| Formulation | Conditions | Dose (mg) | % water Content (% RSD) | |
|---|---|---|---|---|
| | | | Initial n = 3 | 8 weeks n = 3 |
| APD125 Form I:PVP (1:8) 2% w/w methyl cellulose, direct-compression (coated) | 25° C. 60% RH 40° C. 75% RH | 10 40 10 40 | 6.7 (4.5) 5.7 (3.7) 6.7 (4.5) 5.7 (3.7) | 4.8 (0.9) 4.5 (1.1) 6.5 (0.0)$^a$ 5.7 (5.9)$^a$ |

TABLE 31-continued

| Formulation | Conditions | Dose (mg) | % water Content (% RSD) | |
|---|---|---|---|---|
| | | | Initial n = 3 | 8 weeks n = 3 |
| APD125 Form I:coPVP (1:8) 2% w/w methyl cellulose, direct-compression (coated) | 25° C. 60% RH | 10 40 | 4.7 (5.2) 4.3 (0.8) | 4.1 (19.2) 3.9 (0.7)[a] |
| | 40° C. 75% RH | 10 40 | 4.7 (5.2) 4.3 (0.8) | 4.9 (1.7)[a] 4.5 (0.8)[a] |

[a] n = 2

Example 7.6: Nine Months Stability Testing 10-mg and 40-mg, PVP and coPVP-based prototype APD125 tablets were placed on stability testing packaged in HDPE bottles 60 cc with and without desiccant. See Table 32.

TABLE 32

Batches Tested and Packaging

| Batch | Formulation | Strength | Packaging |
|---|---|---|---|
| 1 | APD125/PVP | 10 mg | HDPE bottles with desiccant |
| 2 | | 40 mg | |
| 3 | APD125/coPVP | 10 mg | |
| 4 | | 40 mg | |
| 5 | APD125/PVP | 10 mg | HDPE bottles without desiccant |
| 6 | | 40 mg | |
| 7 | APD125/coPVP | 10 mg | |
| 8 | | 40 mg | |
| 9 | Placebo/PVP | (10 mg) | HDPE bottles with desiccant |
| 10 | | (10 mg) | HDPE bottles without desiccant |
| 11 | | (40 mg) | HDPE bottles with desiccant |
| 12 | | (40 mg) | HDPE bottles without desiccant |

The stability samples were stored at 25° C./60% relative humidity, 30° C./65% relative humidity and 40° C./75% relative humidity to examine the effect of heat and humidity. The studies are conducted according to ICH Q1A® guidelines (stability testing of new drug substances and products).

After a storage duration of 6 months, the stability tests with tablets in bottles without desiccant were stopped and only the stability tests with tablets in bottles with desiccant were measured after a storage duration of 9 months.

After a storage duration of 9 months at 25° C./60% relative humidity in bottles with desiccant, the tablets show an increase of the water content compared with the initial values (PVP max.+2.4%, coPVP max.+4%, placebo tablets max.+1.6%). The tablets were tested again after 10.5 months and the water content was found to be lower than it had been at 9 months. The water content at 10.5 months compared with the initial values was: PVP max.+0.5%; coPVP max.+ 0.5%; placebo tablets max.+0.1%). The difference in water content at 9 months and 10.5 months is probably due to the testing protocols used. At 9 months the tablets were ground on one day but the water content was not measured until the following day. During this delay it is believed the ground tablets picked up moisture from the air. At 10.5 months however, the tablets were ground and tested for water content on the same day.

After a storage duration of 9 months at 25° C./60% relative humidity in bottles with desiccant, a decrease of the crushing strength of the tablets was observed compared with the initial values. The decrease of the 10 mg tablets was higher than the 40 mg tablets (10 mg max.=−24 N; 40 mg max.=−8 N). No significant differences were observed between the active and the placebo tablets and between the PVP and the coPVP formulation.

After a storage duration of 9 months at 25° C./60% relative humidity in bottles with desiccant, no significant decrease of the dissolution rate can be observed.

After a storage duration of 9 months at 25° C./60% relative humidity in bottles with desiccant, the assay results for APD125 were in the same range as the initial conditions. No significant trends of the assay results can be observed and all results are within the specification.

After a storage duration of 9 months at 25° C./60% relative humidity in bottles with desiccant, small amounts of DFA were detected but all results were below the quantitation limit of 75 ppm. For other impurities, no increase were observed and all results were ≤0.05%.

Example 8: Preparation of Intermediate N-[4-Methoxy-3-(2-methyl-2H-pyrazol-3-yl) phenyl]-acetamide

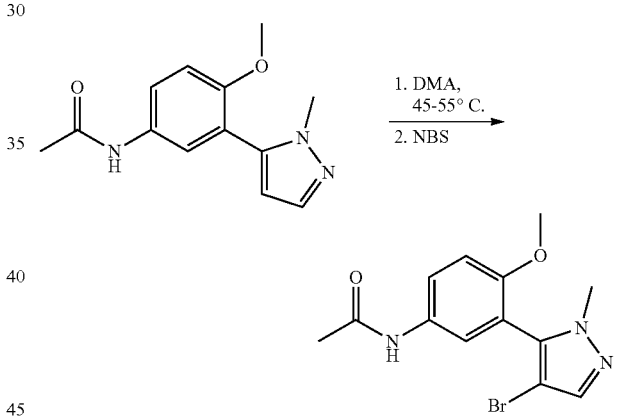

To a solution of N-[4-methoxy-3-(2-methyl-2H-pyrazol-3-yl) phenyl]-acetamide (25.0 kg) in N,N-dimethylacetamide (DMA, 140.5 kg) in a 400 L glass lined jacketed reactor with overhead stirring under nitrogen at 45 to 55° C. internal temperature N-bromosuccinimide (NBS, 19.0 kg) was charged in portions at such a rate as to maintain internal temperature to less than 55° C. The reaction mixture remained a solution at this dilution of DMA and internal temperature of 50.9° C. An "in process check" of the reaction mixture to determine reaction completion after at least 1 hr of stirring at 50° C. showed that the reaction mixture was substantially free of the starting material. Upon cooling of the reaction mixture to an internal temperature of 34° C. water (150 kg) was added in a controlled manner into the reactor to maintain an internal temperature between 40-55° C. A slight exotherm was observed during the reaction quench. The product slurry was then cooled to −5 to 5° C. and filtered through a corrosion resistant filter/dryer. The wetcake was re-slurried, washed with water (2×25 kg), and dried under full house vacuum (~30 in Hg) with a jacket temperature of 65° C. producing N-[3-(4 bromo-2-methyl-2H-pyrazol-3-yl)-4-methoxy phenyl]-acetamide (31.6 kg, 100% purity by HPLC, 96.1% yield).

Example 9: Preparation of Intermediate 3-(4-Bromo-2-methyl-2H-methyl-3-yl)-4-methoxy-phenylamine

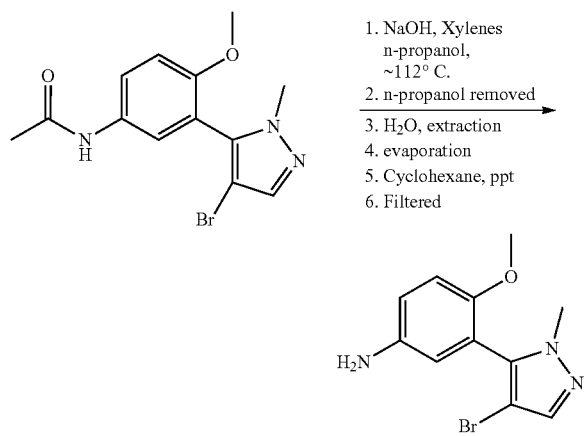

1. NaOH, Xylenes n-propanol, ~112° C.
2. n-propanol removed
3. H₂O, extraction
4. evaporation
5. Cyclohexane, ppt
6. Filtered N-[3-(4 Bromo-2-methyl-2H-pyrazol-3-yl)-4-methoxy phenyl]-acetamide (15.6 kg), xylenes (67.1 kg), n-propanol (12.5 kg), and sodium hydroxide pellets (4.1 kg) were charged into a 400 L Hastelloy jacketed reactor with overhead stirring and nitrogen blanket. The reaction mixture was heated and held at reflux for at least four hours with a peak internal temperature of 107° C. at which point the HPLC analysis of the reaction mixture indicated substantially complete deacetylation of the starting material to product. The reactor condenser was then switched from reflux to distillation configuration to remove most of the n-propanol solvent. This was accomplished by monitoring the temperature profile of the reactor contents and monitoring when the temperature stabilized (126-127° C. $T_{internal}$ with up to 145° C. $T_{jacket}$) indicating near-complete removal of n-propanol. The product mixture was cooled to 80° C. and water (15.6 L) was added to extract the inorganic material from the product dissolved in xylenes. The aqueous extraction was repeated by adding water (11.7 kg) at 70-80° C. and performing a second extraction to remove residual inorganics from the product solution. Upon cooling to 65° C. vacuum was applied to effect distillation of approximately 40% of initial xylenes charge at which point precipitation was observed. The reaction slurry was further cooled to 40° C. Cyclohexane (10.5 L) was charged in portions to control precipitation at an internal temperature 36.6 to 41.1° C. Upon completion of the cyclohexane anti-solvent addition, the reaction mixture was cooled to −11.9° C. (maximize the yield). The solid product was filtered using a filter/dryer, washed with cyclohexane (2×12.2 kg), and dried under full house vacuum (~30 in Hg) and with increasing internal temperature up to 40° C. isolating 3-(4-bromo-2-methyl-2H-methyl-3-yl)-4-methoxy-phenylamine (12.29 kg, 100% purity by HPLC, and 92% yield).

Example 10: Preparation of Form I of 1-[3-(4-Bromo-2-methyl-2H-pyrazol-3-yl)-4-methoxy-phenyl]-3-(2,4-difluoro-phenyl)-urea, Direct Method, (Compound I)

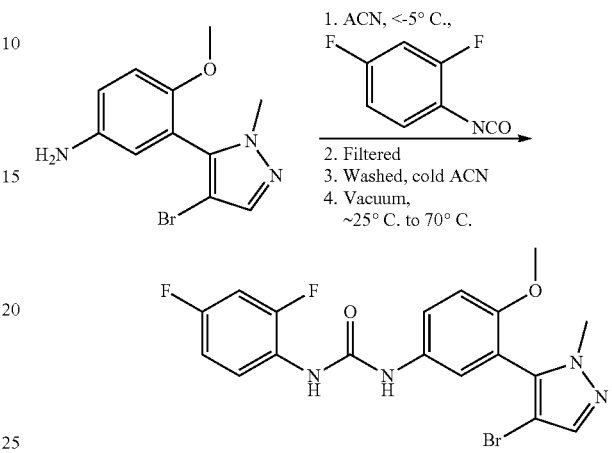

1. ACN, <−5° C.,
2. Filtered
3. Washed, cold ACN
4. Vacuum, ~25° C. to 70° C.

To a solution of 3-(4-bromo-2-methyl-2H-methyl-3-yl)-4-methoxy-phenylamine (16.7 kg) in acetonitrile (78.6 kg) in a 200 L glass jacketed reactor with overhead stirring and nitrogen blanket at an internal temperature of <−10° C. 2,4-difluorophenyl-isocyanate (9.68 kg) was controlled charged through a 1 micron line filter at a rate substantially slow enough to prevent co-precipitation of the starting material in the product. After continued stirring at <−10° C. for approximately 1 hour post completion of the 2,4-difluorophenyl-isocyanate addition, the conversion of starting material to product was substantially complete. The product slurry was filtered and washed with cold acetonitrile (26.3 kg) at <−5° C. producing the acetonitrile solvate of the product. Full house vacuum (~30 in Hg) was applied to the bottom outlet filter/dryer while nitrogen flowed through from the top enhancing the removal of volatile solvents without application of heat. Samples were removed from the bulk material and LOD was determined using an IR-200 Moisture Analyzer Instrument (Denver Instrument Company). The time course is shown below:

| Sample No. | LOD % | Time (h) |
|---|---|---|
| 1 | 38.48 | 0 |
| 2 | 29.63 | 7 |
| 3 | 20.96 | 13.5 |
| 4 | 7.28 | 19.5 |

Drying of the "wetcake" was maintained at ambient temperature under full house vacuum (~30 in Hg) for about 19.5 h at which time the LOD was 7.28%. At this point, the temperature was raised to 70° C. under full house vacuum (~30 in Hg) for 11 hrs to afford 1-[3-(4-bromo-2-methyl-2H-pyrazol-3-yl)-4-methoxy-phenyl]-3-(2,4-difluoro-phenyl)-urea (24.2 kg, 99.94% HPLC purity, form I determined by PXRD, and 92.9% yield).

Example 11: Conversion of Form II of 1-[3-(4-Bromo-2-methyl-2H-pyrazol-3-yl)-4-methoxy-phenyl]-3-(2,4-difluoro-phenyl)-urea to Form I of 1-[3-(4-Bromo-2-methyl-2H-pyrazol-3-yl)-4-methoxy-phenyl]-3-(2,4-difluoro-phenyl)-urea

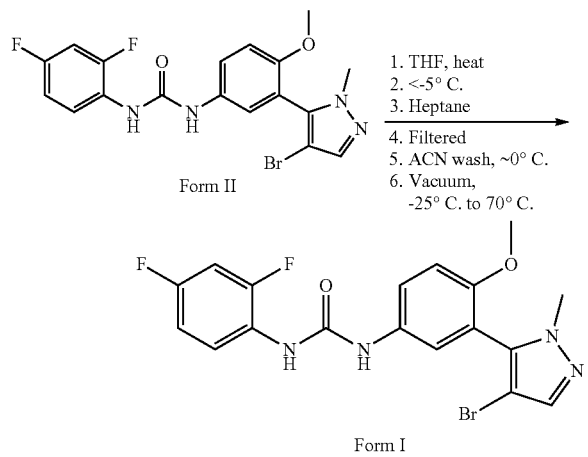

1-[3-(4-Bromo-2-methyl-2H-pyrazol-3-yl)-4-methoxy-phenyl]-3-(2,4-difluoro-phenyl)-urea (24.2 kg) was dissolved in tetrahydrofuran (85.6 kg) in a 200 L Hastelloy jacketed reactor with overhead stirring and nitrogen blanket at or near reflux (62.4° C.). Solids which had precipitated on the wall were washed down with THF (8.6 kg). The THF solution was transferred through a line filter into a 400 L glass lined reactor. At a reduced THF solution internal temperature of <−5° C., heptane (128.5 kg) was added into the reactor at a controlled rate such that internal temperature did not exceed −5° C. After having been stirred at <−5° C. for 17 min, the resulting slurry was filtered through a Hastelloy filter/dryer, and the solid product was washed with precooled acetonitrile (18.9 kg) at −11° C. (without the acetonitrile wash, the heptane level in the dried product would be about 10,000 ppm, which would exceed the ICH guideline of <5000 ppm). Full house vacuum (~30 in Hg) was applied to the bottom outlet filter/dryer while nitrogen flows through from the top enhancing the removal of volatile solvents without application of heat. The volatile solvent content of the wetcake was 4.85% prior to application of heat. Upon drying at 70° C. under full house vacuum (~30 in Hg), 1-[3-(4-bromo-2-methyl-2H-pyrazol-3-yl)-4-methoxy-phenyl]-3-(2,4-difluoro-phenyl)-urea (21.9 kg, Form I determined by PXRD, and 90.5% yield) was isolated.

Example 12: Powder X-Ray Diffraction of Form I of 1-[3-(4-Bromo-2-methyl-2H-pyrazol-3-yl)-4-methoxy-phenyl]-3-(2,4-difluoro-phenyl)-urea (Compound I)

Powder X-ray Diffraction (PXRD) data were collected on an X'Pert PRO MPD powder diffractometer (PANalytical, Inc.) with a Cu source set at 45 kV and 40 mA, a Ni-filter to remove Cu Kβ radiation, and an X'Celerator detector. The instrument was calibrated by the vendor using a silicon powder standard NIST #640c. The calibration was found to be correct when it was tested with NIST #675 low-angle diffraction standard. The sample was prepared for PXRD scanning by placing several milligrams of compound onto a sample holder and smoothing as flat as possible by pressing weigh paper down on the sample with a flat object. The sample was analyzed using a spinning-sample stage. Scans covered the range of 5 to 40°2θ. A continuous scan mode was used with a step size of 0.0170°2θ. Diffraction data were viewed and analyzed with the X'Pert Data Viewer Software, version 1.0a and X'Pert HighScore Software, version 1.0b.

The PXRD pattern for Form I of 1-[3-(4-bromo-2-methyl-2H-pyrazol-3-yl)-4-methoxy-phenyl]-3-(2,4-difluoro-phenyl)-urea (Compound I) is shown in FIG. 21.

TABLE 33

Observed Peaks for Form I of 1-[3-(4-Bromo-2-methyl-2H-pyrazol-3-yl)-4-methoxy- phenyl]-3-(2,4-difluoro-phenyl)-urea (Compound I) Ranging from 5 °2θ to 30 °2θ

| Pos. [°2θ] | Rel. Int. [%] |
| --- | --- |
| 5.6* | 100.0 |
| 7.4* | 23.4 |
| 7.7 | 9.5 |
| 9.2 | 0.1 |
| 9.7 | 0.3 |
| 11.2* | 25.7 |
| 11.6 | 7.6 |
| 12.8 | 4.9 |
| 12.8 | 4.9 |
| 14.0 | 2.8 |
| 14.5 | 1.4 |
| 15.2 | 4.3 |
| 15.5 | 3.5 |
| 15.7 | 5.5 |
| 16.1 | 2.2 |
| 16.5 | 1.5 |
| 17.9 | 1.9 |
| 18.5 | 5.1 |
| 19.3 | 3.2 |
| 20.3 | 3.5 |
| 20.4 | 4.4 |
| 21.1* | 49.3 |
| 22.0 | 2.0 |
| 22.5 | 1.9 |
| 23.1 | 1.7 |
| 23.9 | 1.3 |
| 24.3 | 2.3 |
| 24.5 | 2.9 |
| 25.0* | 17.4 |
| 25.6 | 4.2 |
| 26.0 | 4.8 |
| 26.3 | 5.8 |
| 26.8 | 9.5 |
| 26.9 | 8.3 |
| 27.4 | 4.0 |
| 28.0 | 8.1 |
| 28.1 | 7.9 |
| 28.8 | 4.8 |
| 29.1 | 3.9 |

*Peaks of about 17% or greater relative intensity.

The PXRD pattern for a tetrahydrofuran solvate of 1-[3-(4-bromo-2-methyl-2H-pyrazol-3-yl)-4-methoxy-phenyl]-3-(2,4-difluoro-phenyl)-urea (Compound I) is shown in FIG. 29.

The PXRD pattern for a heptane solvate of 1-[3-(4-bromo-2-methyl-2H-pyrazol-3-yl)-4-methoxy-phenyl]-3-(2,4-difluoro-phenyl)-urea (Compound 1) is shown in FIG. 30.

Example 13: Differential Scanning Calorimetry for Form I of 1-[3-(4-Bromo-2-methyl-2H-pyrazol-3-yl)-4-methoxy-phenyl]-3-(2,4-difluoro-phenyl)-urea (Compound I)

Differential Scanning Calorimetry (DSC) was performed on a TA instruments, Inc. DSC Q2000 at 10° C./min. The instrument was calibrated at this scan rate by the vendor for temperature and energy using the melting point and enthalpy of fusion of an indium standard. Samples were prepared by taring a sample-pan lid along with a sample-pan bottom on a Mettler Toldeo MX5 balance. Sample was placed in the bottom of the tared sample pan. The sample-pan lid fitted snuggly in the sample-pan bottom. The sample and pan were reweighed to get the sample weight. Thermal events (for example, onset temperature, enthalpy of fusion) are calculated using the Universal Analysis 2000 software, version 4.1D, Build 4.1.0.16.

Figure 22:
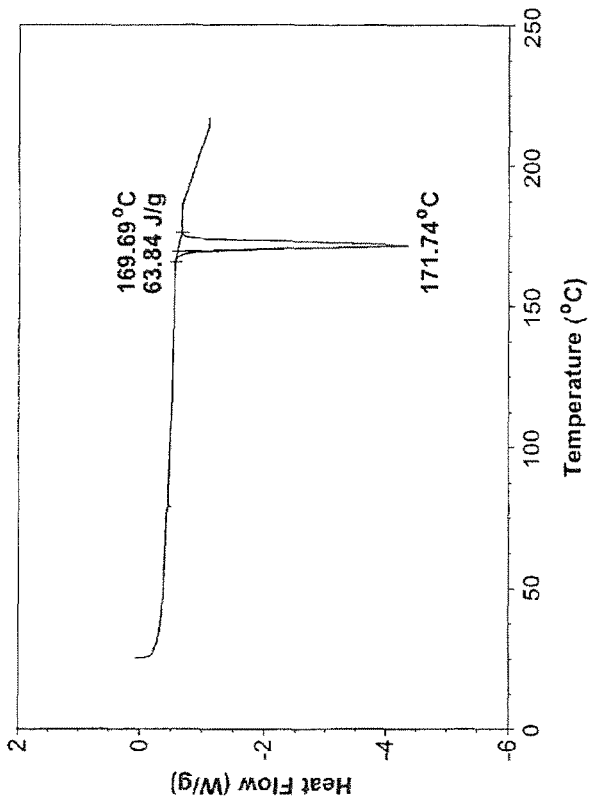
FIG. 22 depicts a differential scanning calorimetry (DSC) thermogram for Form I of 1-[3-(4-bromo-2-methyl-2H-pyrazol-3-yl)-4-methoxy-phenyl]-3-(2,4-difluoro-phenyl)-urea (Compound I), which was recorded using a TA Instruments DSC Q1000; at 10° C./min.

The DSC thermogram for Form I of 1-[3-(4-bromo-2-methyl-2H-pyrazol-3-yl)-4-methoxy-phenyl]-3-(2,4-difluoro-phenyl)-urea (Compound I) is shown in FIG. 22.

Example 14: FT-Raman Spectroscopy for Form I of 1-[3-(4-Bromo-2-methyl-2H-pyrazol-3-yl)-4-methoxy-phenyl]-3-(2,4-difluoro-phenyl)-urea (Compound I)

The Raman spectrum for Form I of 1-[3-(4-bromo-2-methyl-2H-pyrazol-3-yl)-4-methoxy-phenyl]-3-(2,4-difluoro-phenyl)-urea (Compound I) was recorded using the ThermoFisher NXR6700 FT-Raman Spectrometer (EQ1874), NXR6700 FT-Raman Spectrometer (Thermo-Fisher Scientific, Serial # AHR0700837), NXR FT-Raman Module (ThermoFisher Scientific AEU0700442) and using the FT-Raman Micro-Stage Accessory (ThermoFisher Scientific AIS0800151). The instrument comprises a NdYAg laser operating at a wavelength of 1064 nm, an interferometer with a calcium fluoride beam-splitter, and an InGaAs detector. No background spectrum was required, and the Raman spectra were recorded by placing approximately 1 mg of each sample directly into the powder cup on the sample stage.

In order to collect the spectra, 1024 transients of an interferogram containing 8192 points were acquired with 4 $cm^{-1}$ resolution. The spectrum was recorded from 100 $cm^{-1}$ to 3700 $cm^{-1}$. The interferogram was apodized with a Happ-Genzel function and the data was zero-filled once prior to the application of a power spectrum for phase correction.

Collection and Processing Information

Number of sample scans: 2048; Collection length: 4240.4 sec; Resolution: 4.000; Levels of zero filling: 1; Number of scan points: 16672; Number of FFT points: 32768; Laser frequency: 15798.3 $cm^{-1}$; Interferogram peak position: 8192; Apodization: Happ-Genzel; Phase correction: Power spectrum; Number of background scans: 0; and Background gain: 0.0.

Data Description:

Number of points: 3737, X-axis: Raman shift (cm-1), Y-axis: Raman intensity, First X value: 99.2486, Last X value: 3701.6821, Raman laser frequency: 9393.6416, Data spacing: 0.964249.

Spectrometer Description:

Spectrometer: Nicolet 6700, Source: Off, Detector: InGaAs, Smart Accessory ID: Unknown, Beamsplitter: CaF2, Sample spacing: 1.0000, Digitizer bits: 24, Mirror velocity: 0.3165, Aperture: 59.00, Sample gain: 64.0, High pass filter: 200.0000, Low pass filter: 11000.0000.

Data Processing:

Final format: Shifted spectrum, Resolution: 4.000 from 99.2486 to 3701.6821, Laser power at sample: 0.699 W.

Figure 23:
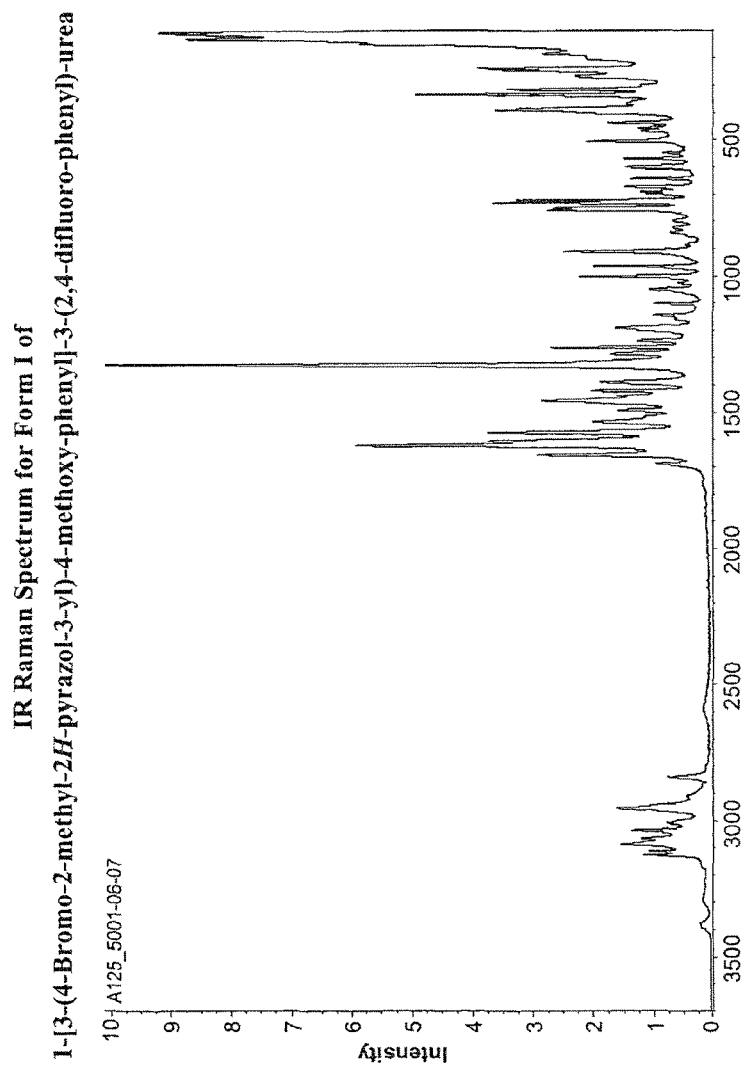
FIG. 23 depicts an FT Raman spectrum for Form I of 1-[3-(4-bromo-2-methyl-2H-pyrazol-3-yl)-4-methoxy-phenyl]-3-(2,4-difluoro-phenyl)-urea (Compound I), which was recorded using a ThermoFisher NXR6700 FT-Raman Spectrometer (EQ1874) using the FT-Raman Micro-Stage Accessory.

The FT-Raman Spectrum for Form I of 1-[3-(4-bromo-2-methyl-2H-pyrazol-3-yl)-4-methoxy-phenyl]-3-(2,4-difluoro-phenyl)-urea (Compound I) is shown in FIG. 23.

Example 15: Thermogravimetric Analysis (TGA) for Form I of 1-[3-(4-Bromo-2-methyl-2H-pyrazol-3-yl)-4-methoxy-phenyl]-3-(2,4-difluoro-phenyl)-urea (Compound I)

Thermal Gravimetric Analysis (TGA) was performed on the TA Instruments, Inc. TGA Q500. The instrument is calibrated by the vendor at 10° C./min. for temperature using the curie point of a ferromagnetic standard. The balance is calibrated with a standard weight. Sample scans are performed at 10° C./min. Sample was placed into an open sample pan, previously tared on the TGA balance. Thermal events such as weight-loss are calculated using the Universal Analysis 2000 software, version 4.1D, Build 4.1.0.16.

Figure 24:
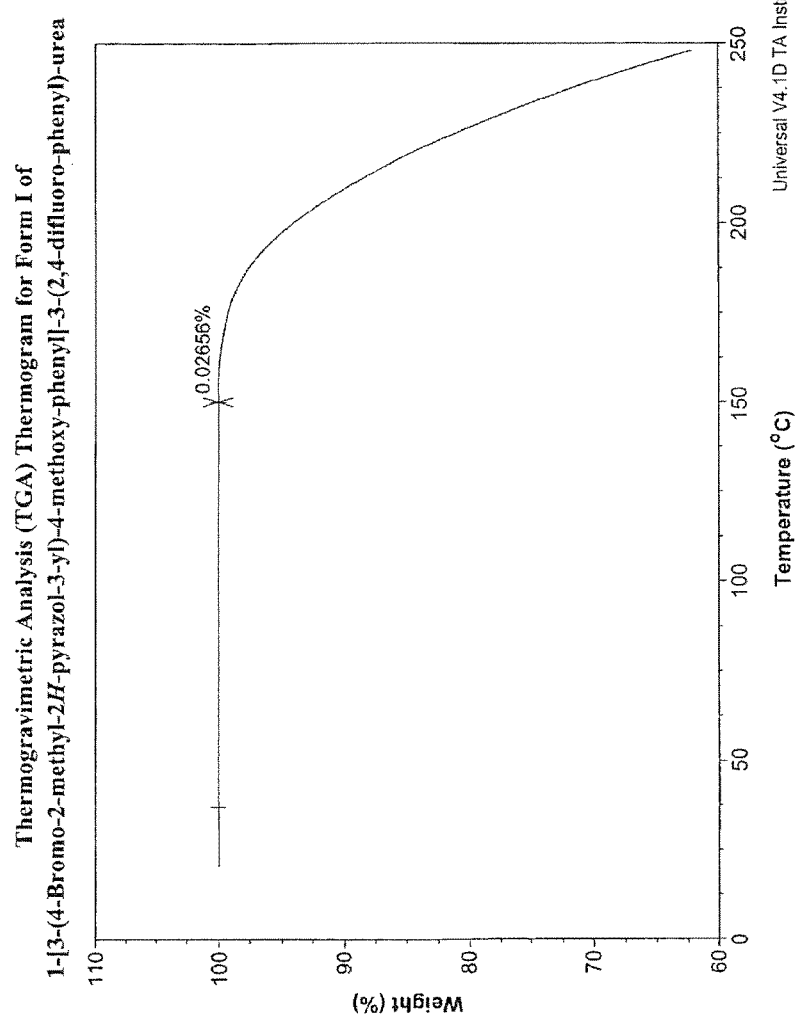
FIG. 24 depicts a thermogravimetric analysis (TGA) thermogram for Form I of 1-[3-(4-bromo-2-methyl-2H-pyrazol-3-yl)-4-methoxy-phenyl]-3-(2,4-difluoro-phenyl)-urea (Compound I), which was recorded using a TA Instruments TGA Q500 in a nitrogen atmosphere. The percent change in weight as a function of temperature was recorded.

The TGA thermogram for Form I of 1-[3-(4-bromo-2-methyl-2H-pyrazol-3-yl)-4-methoxy-phenyl]-3-(2,4-difluoro-phenyl)-urea (Compound I) is shown in FIG. 24.

Example 16: Single-Crystal X-Ray Structure of Hemi-Acetonitrile Solvate of 1-[3-(4-Bromo-2-methyl-2H-pyrazol-3-yl)-4-methoxy-phenyl]-3-(2,4-difluoro-phenyl)-urea Crystal structure determination was carried out under non-GMP conditions at Purdue Crystallography Laboratory, West Lafayette, Ind.

1. Data Collection

A colorless needle of $C_{18}H_{15}BrF_2N_4O_2$, $0.5(CH_3CN)$ having approximate dimensions of 0.47×0.13×0.11 mm was mounted on a glass fiber in a random orientation. Preliminary examination and data collection were performed Mo $K_\alpha$ radiation (A=0.71073 A) on a Nonius KappaCCD equipped with a graphite crystal, incident beam monochromator.

Cell constants for data collection were obtained from least-squares refinement, using the setting angles of 17249 reflections in the range 3<θ<25°. The refined mosaicity from DENZO/SCALEPACK (Otwinowski et al., *Methods Enzymology* 1997, 276, 307) was 0.51° indicating moderate crystal quality. The space group was determined by the program XPREP (Bruker, XPREP in SHELXTL version 6.12, Bruker AXS Inc., Madison, Wis., USA, (2002)). There were no systematic absences; the space group was determined to be P-1 (no 2).

The data were collected at a temperature of 150° K. Data were collected to a maximum 2θ of 51.2°.

2. Data Reduction

A total of 17249 reflections were collected, of which 6818 were unique. Frames were integrated with DENZO-SMN (Otwinowski et al., *Methods Enzymology* 1997, 276, 307).

Lorentz and polarization corrections were applied to the data. The linear absorption coefficient is 21.3/cm for Mo $K_\alpha$ radiation. An empirical absorption correction using SCALEPACK (Otwinowski et al., *Methods Enzymology* 1997, 276, 307) was applied.

Transmission coefficients ranged from 0.688 to 0.791. Intensities of equivalent reflections were averaged. The agreement factor for the averaging was 6.1% based on intensity.

3. Structure Solution and Refinement

The structure was solved by direct methods using SIR2004 (Burla et al., *J. Appl. Cryst.*, 2005, 38, 381). The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2-|F_c|^2)^2$$

The weight w is defined as:

$$1/[\sigma^2(F_o^2)+(0.0600P)^2+7.0096P] \text{ where } P=(F_o^2+2F_c^2)/3$$

Scattering factors were taken from the "International Tables for Crystallography" (International Tables for Crystallography, Vol. C, Kluwer Academic Publishers, Utrecht, The Netherlands, (1992), Tables 4.2.6.8 and 6.1.1.4.). Of the 6818 reflections were used in the refinements, only 5185 reflections with $F_o^2>2\sigma(F_o^2)$ were used in calculating R I. The final cycle of refinement included 575 variable parameters and converged (largest parameter shift was <0.01 times its estimated standard deviation) with unweighted and weighted agreement factors of:

$$R = \Sigma|F_o - F_c|/\Sigma F_o = 0.079$$

$$R_w = \sqrt{(\Sigma w(F_o^2 - F_c^2)^2/\Sigma w(F_o^2)^2)} = 0.161$$

The standard deviation of an observation of unit weight was 1.11. The highest peak in the final difference Fourier had a height of 0.62 e/A$^3$. The minimum negative peak had a height of −1.07 e/A$^3$.

Refinement was performed on a LINUX PC using SHELX-97 (Sheldrick, SHELXL97, A Program for Crystal Structure Refinement, Univ. of Gottingen, Germany, (1997)).

The crystallographic drawing in FIG. 25 was done using Mercury v. 1.4.2 (build 2).

Example 17: Powder X-Ray Diffraction of Form II of 1-[3-(4-Bromo-2-methyl-2H-pyrazol-3-yl)-4-methoxy-phenyl]-3-(2,4-difluoro-phenyl)-urea (Compound I)

Powder X-ray Diffraction (PXRD) data were collected on an X'Pert PRO MPD powder diffractometer (PANalytical, Inc.) with a Cu source set at 45 kV and 40 mA, a Ni-filter to remove Cu Kβ radiation, and an X'Celerator detector. The instrument was calibrated by the vendor using a silicon powder standard NIST #640c. The calibration was found to be correct when it was tested with NIST #675 low-angle diffraction standard. The sample was prepared for PXRD scanning by placing several milligrams of compound onto a sample holder and smoothing as flat as possible by pressing weigh paper down on the sample with a flat object. The sample was analyzed using a spinning-sample stage. Scans covered the range of 5 to 40°2θ. A continuous scan mode was used with a step size of 0.0170°2θ. Diffraction data were viewed and analyzed with the X'Pert Data Viewer Software, version 1.0a and X'Pert HighScore Software, version 1.0b.

Figure 31:
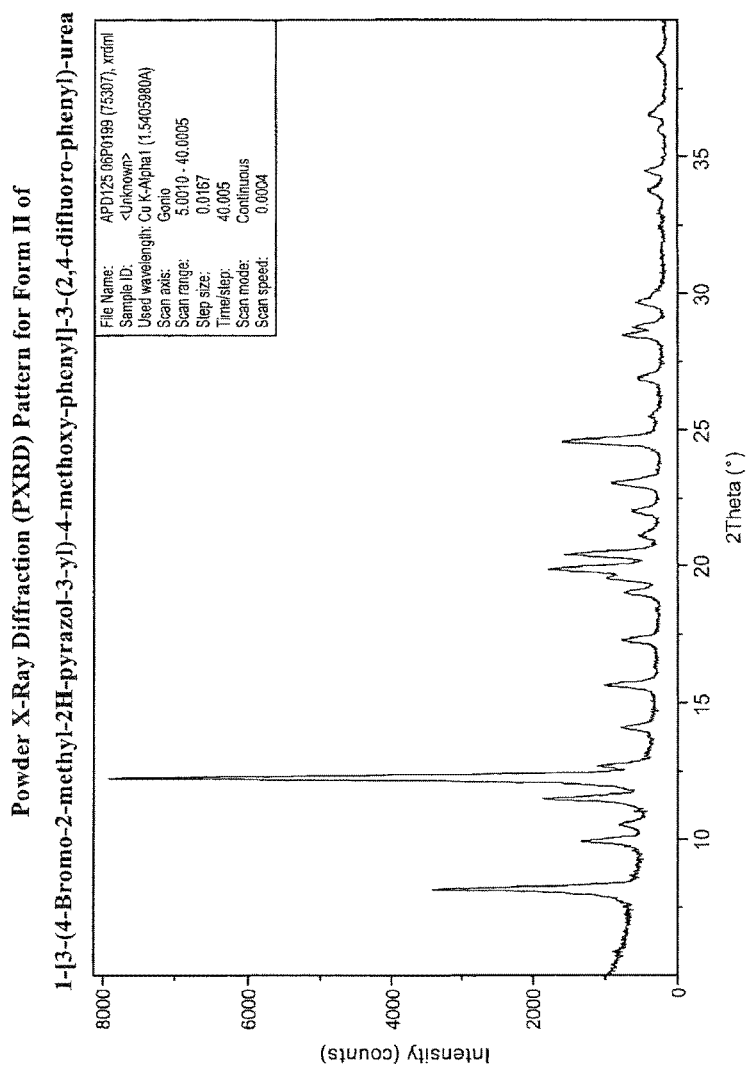
FIG. 31 depicts a powder X-ray diffraction (PXRD) pattern for Form II of 1-[3-(4-bromo-2-methyl-2H-pyrazol-3-yl)-4-methoxy-phenyl]-3-(2,4-difluoro-phenyl)-urea (Compound 1), which was recorded using a PANalytical X'Pert Plus Powder X-Ray Diffractometer in the theta/theta geometry; scanning angles 5.0°-40.0°2θ.

The PXRD pattern for Form II of 1-[3-(4-bromo-2-methyl-2H-pyrazol-3-yl)-4-methoxy-phenyl]-3-(2,4-difluoro-phenyl)-urea (Compound I) is shown in FIG. 31.

TABLE 34

Observed Peaks for Form II of 1-[3-(4-Bromo-2-methyl-2H-pyrazol-3-yl)-4-methoxy- phenyl]-3-(2,4-difluoro-phenyl)-urea (Compound I) Ranging from 5 °2θ to 30 °2θ

| Pos. [°2θ] | Rel. Int. [%] |
|---|---|
| 5.3 | 0.4 |
| 5.9 | 0.3 |
| 6.8 | 0.2 |
| 8.2* | 37.6 |
| 8.7 | 1.0 |
| 9.9 | 10.9 |
| 10.5 | 4.1 |
| 11.5* | 18.6 |
| 12.3* | 100.0 |
| 12.7 | 8.9 |
| 14.1 | 5.5 |
| 15.6 | 8.8 |
| 16.5 | 0.2 |
| 17.3 | 6.5 |
| 19.0 | 6.2 |
| 19.1 | 5.5 |
| 19.6 | 9.7 |
| 19.9* | 20.0 |
| 20.4* | 16.2 |
| 21.1 | 3.3 |
| 22.0 | 4.7 |
| 22.1 | 5.0 |
| 23.0 | 8.9 |
| 24.6* | 18.4 |
| 24.7* | 14.5 |
| 25.5 | 2.0 |
| 26.9 | 4.4 |
| 27.6 | 0.5 |
| 28.4 | 5.2 |
| 28.5 | 7.3 |
| 28.8 | 5.6 |
| 29.6 | 4.8 |
| 30.0 | 2.1 |
| 31.6 | 0.4 |
| 32.4 | 0.5 |
| 33.0 | 0.8 |
| 33.8 | 3.1 |
| 34.5 | 3.8 |
| 35.0 | 0.4 |
| 36.0 | 1.2 |
| 36.5 | 2.9 |
| 37.3 | 0.3 |
| 38.7 | 1.7 |
| 39.7 | 0.4 |

*Peaks of about 14% or greater relative intensity.

Those skilled in the art will recognize that various modifications, additions, substitutions and variations to the illustrative examples set forth herein can be made without departing from the spirit of the invention and are, therefore, considered within the scope of the invention. All documents referenced above, including, but are not limited to, printed publications and provisional and regular patent applications, are incorporated herein by reference in their entirety.

What is claimed is:

1. A process for preparing Form I of 1-[3-(4-bromo-2-methyl-2H-pyrazol-3-yl)-4-methoxy-phenyl]-3-(2,4-difluoro-phenyl)-urea, said process comprising:
   a. dissolving 1-[3-(4-bromo-2-methyl-2H-pyrazol-3-yl)-4-methoxy-phenyl]-3-(2,4-difluoro-phenyl)-urea in tetrahydrofuran to form a solution;
   b. adding heptane to said solution to form a mixture comprising a heptane solvate of 1-[3-(4-bromo-2-methyl-2H-pyrazol-3-yl)-4-methoxy-phenyl]-3-(2,4-difluoro-phenyl)-urea;
   c. isolating said heptane solvate of 1-[3-(4-bromo-2-methyl-2H-pyrazol-3-yl)-4-methoxy-phenyl]-3-(2,4-difluoro-phenyl)-urea from said mixture to provide an isolated heptane solvate of 1-[3-(4-bromo-2-methyl-2H-pyrazol-3-yl)-4-methoxy-phenyl]-3-(2,4-difluoro-phenyl)-urea;
d. washing said isolated heptane solvate of 1-[3-(4-bromo-2-methyl-2H-pyrazol-3-yl)-4-methoxy-phenyl]-3-(2,4-difluoro-1-phenyl)-urea with acetonitrile to form a second solvate of 1-[3-(4-bromo-2-methyl-2H-pyrazol-3-yl)-4-methoxy-phenyl]-3-(2,4-difluoro-phenyl)-urea; and
e. converting said second solvate to provide Form I of 1-[3-(4-bromo-2-methyl-2H-pyrazol-3-yl)-4-methoxy-phenyl]-3-(2,4-difluoro-phenyl)-urea;
f. wherein said heptane solvate has a powder X-ray diffraction pattern substantially as shown in FIG. 30.

2. The process according to claim 1, wherein adding the heptane to the solution in step b) is conducted at a temperature of about −35° C. to about 10° C.

3. The process according to claim 1, wherein adding the heptane to the solution in step b) is conducted at a temperature of about −25° C. to about −5° C.

4. The process according to claim 1, further comprising cooling the 1-[3-(4-bromo-2-methyl-2H-pyrazol-3-yl)-4-methoxy-phenyl]-3-(2,4-difluoro-1-phenyl)-urea in tetrahydrofuran in step a) to less than −5° C. prior to step b).

5. A process for preparing Form I of 1-[3-(4-bromo-2-methyl-2H-pyrazol-3-yl)-4-methoxy-phenyl]-3-(2,4-difluoro-phenyl)-urea, said process comprising:
a. dissolving 1-[3-(4-bromo-2-methyl-2H-pyrazol-3-yl)-4-methoxy-phenyl]-3-(2,4-difluoro-phenyl)-urea in tetrahydrofuran to form a solution;
b. adding heptane to said solution to form a mixture comprising a first solvate of 1-[3-(4-bromo-2-methyl-2H-pyrazol-3-yl)-4-methoxy-phenyl]-3-(2,4-difluoro-1-phenyl)-urea;
c. isolating said first solvate of 1-[3-(4-bromo-2-methyl-2H-pyrazol-3-yl)-4-methoxy-phenyl]-3-(2,4-difluoro-phenyl)-urea from said mixture to provide an isolated heptane solvate of 1-[3-(4-bromo-2-methyl-2H-pyrazol-3-yl)-4-methoxy-phenyl]-3-(2,4-difluoro-phenyl)-urea;
d. washing said isolated first solvate of 1-[3-(4-bromo-2-methyl-2H-pyrazol-3-yl)-4-methoxy-phenyl]-3-(2,4-difluoro-phenyl)-urea with acetonitrile to form a second solvate of 1-[3-(4-bromo-2-methyl-2H-pyrazol-3-yl)-4-methoxy-phenyl]-3-(2,4-difluoro-1-phenyl)-urea; and
e. converting said second solvate to provide Form I of 1-[3-(4-bromo-2-methyl-2H-pyrazol-3-yl)-4-methoxy-phenyl]-3-(2,4-difluoro-phenyl)-urea;
f. wherein said first solvate is a tetrahydrofuran solvate and wherein said tetrahydrofuran solvate has a powder X-ray diffraction pattern substantially as shown in FIG. 29.

6. A heptane solvate of 1-[3-(4-bromo-2-methyl-2H-pyrazol-3-yl)-4-methoxy-phenyl]-3-(2,4-difluoro-phenyl)-urea, wherein said heptane solvate has a powder X-ray diffraction pattern substantially as shown in FIG. 30.

7. A tetrahydrofuran solvate of 1-[3-(4-bromo-2-methyl-2H-pyrazol-3-yl)-4-methoxy-phenyl]-3-(2,4-difluoro-phenyl)-urea, wherein said tetrahydrofuran solvate has a powder X-ray diffraction pattern substantially as shown in FIG. 29.

8. An acetonitrile solvate of 1-[3-(4-bromo-2-methyl-2H-pyrazol-3-yl)-4-methoxy-phenyl]-3-(2,4-difluoro-phenyl)-urea, wherein said acetonitrile solvate has a powder X-ray diffraction pattern substantially as shown in FIG. 27.

\* \* \* \* \*